United States Patent
Taylor et al.

(10) Patent No.: US 7,241,310 B2
(45) Date of Patent: Jul. 10, 2007

(54) METHOD AND APPARATUS FOR REDUCING MITRAL REGURGITATION

(76) Inventors: Daniel C. Taylor, 35 Faneuil St., Brighton, MA (US) 02135; William E. Cohn, 104 Lagrange St., Chestnut Hill, MA (US) 02467; John R. Liddicoat, 68 Myrtle St., Apt. 4, Boston, MA (US) 02114; Steven B. Woolfson, Constitution Marina 28 Constitution Rd., P.O. Box 51837, Boston, MA (US) 02205; Todd F. Davenport, 48 Salem St., Andover, MA (US) 01810; Richard B. Streeter, 66 Brookside Ave., Winchester, MA (US) 01890; Thomas F. Kordis, 7112 Avalon Dr., Wilmington, MA (US) 01887; Jonathan Rourke, 23 Locust St., Belmont, MA (US) 02478

( * ) Notice: Subject to any disclaimer, the term of this patent is extended or adjusted under 35 U.S.C. 154(b) by 0 days.

(21) Appl. No.: 10/342,034

(22) Filed: Jan. 14, 2003

(65) Prior Publication Data

US 2004/0019377 A1   Jan. 29, 2004

Related U.S. Application Data

(63) Continuation-in-part of application No. 10/068,264, filed on Feb. 5, 2002, now Pat. No. 6,656,221, and a continuation-in-part of application No. 10/112,354, filed on Mar. 29, 2002, now Pat. No. 7,186,264, and a continuation-in-part of application No. 10/218,649, filed on Aug. 14, 2002.

(60) Provisional application No. 60/348,424, filed on Jan. 14, 2002.

(51) Int. Cl.
    *A61F 2/24* (2006.01)
(52) U.S. Cl. .................................. 623/2.36; 623/2.11
(58) Field of Classification Search ............... 623/2.11, 623/2.36
    See application file for complete search history.

(56) References Cited

U.S. PATENT DOCUMENTS 4,535,757 A   8/1985  Webster, Jr.

(Continued)

FOREIGN PATENT DOCUMENTS

DE        10161543 A1 *  6/2003

(Continued)

OTHER PUBLICATIONS

Glover, Robert P. et al., The Treatment of Mitral Valve Insufficiency By The Purse-String Technique, The Journal of Thoracic Surgery, Jan. 1957, 14 pages.

(Continued)

*Primary Examiner*—Corrine McDermott
*Assistant Examiner*—Thomas J. Sweet
(74) *Attorney, Agent, or Firm*—Pandiscio & Pandiscio

(57) ABSTRACT

A method and device for reducing mitral regurgitation. An elongated body is positioned in a coronary sinus of a patient in a vicinity of a heart mitral valve posterior leaflet. The body is adapted to straighten a natural curvature of at least a portion of the coronary sinus in the vicinity of the posterior leaflet to move a posterior annulus anteriorly, which in turn moves the posterior leaflet anteriorly, thereby to improve leaflet coaptation.

33 Claims, 87 Drawing Sheets

U.S. PATENT DOCUMENTS

| | | | |
|---|---|---|---|
| 4,669,473 A | 6/1987 | Richards et al. | |
| 4,917,698 A | 4/1990 | Carpentier et al. | |
| 4,944,745 A | 7/1990 | Sogard et al. | |
| 5,061,277 A | 10/1991 | Carpentier et al. | |
| 5,092,889 A | 3/1992 | Campbell, Jr. | |
| 5,269,809 A | 12/1993 | Hayhurst et al. | |
| 5,332,402 A | 7/1994 | Teitelbaum | |
| 5,383,892 A | 1/1995 | Cardon et al. | |
| 5,389,091 A | 2/1995 | Moorehead | |
| 5,443,481 A | 8/1995 | Lee | |
| 5,462,530 A * | 10/1995 | Jang | 604/160 |
| 5,476,506 A | 12/1995 | Lunn | |
| 5,527,292 A | 6/1996 | Adams et al. | |
| 5,545,209 A | 8/1996 | Roberts et al. | |
| 5,562,620 A | 10/1996 | Klein et al. | |
| 5,569,201 A | 10/1996 | Burns | |
| 5,575,799 A | 11/1996 | Bolanos et al. | |
| 5,681,345 A | 10/1997 | Euteneuer | |
| 5,720,726 A | 2/1998 | Marcadis et al. | |
| 5,755,778 A | 5/1998 | Kleshinski | |
| 5,755,781 A | 5/1998 | Jayaraman | |
| 5,800,495 A | 9/1998 | Machek et al. | |
| 5,800,526 A | 9/1998 | Anderson et al. | |
| 5,855,565 A | 1/1999 | Bar-Cohen et al. | |
| 5,911,732 A | 6/1999 | Hojeibane | |
| 5,957,949 A | 9/1999 | Leonhardt et al. | |
| 5,980,570 A | 11/1999 | Simpson | |
| 5,984,917 A | 11/1999 | Fleischman et al. | |
| 6,033,436 A | 3/2000 | Steinke et al. | |
| 6,051,020 A | 4/2000 | Goicoechea et al. | |
| 6,071,263 A | 6/2000 | Kirkman | |
| 6,086,599 A | 7/2000 | Lee et al. | |
| 6,090,136 A | 7/2000 | McDonald et al. | |
| 6,119,037 A | 9/2000 | Kellogg et al. | |
| 6,162,245 A | 12/2000 | Jayaraman | |
| 6,165,194 A | 12/2000 | Denardo | |
| 6,187,040 B1 | 2/2001 | Wright | |
| 6,210,432 B1 | 4/2001 | Solem et al. | |
| 6,241,746 B1 | 6/2001 | Bosma et al. | |
| 6,258,117 B1 | 7/2001 | Camrud et al. | |
| 6,277,107 B1 | 8/2001 | Lurie et al. | |
| 6,328,765 B1 | 12/2001 | Hardwick et al. | |
| 6,332,896 B1 | 12/2001 | Hubbard et al. | |
| 6,402,781 B1 | 6/2002 | Langberg et al. | |
| 6,419,696 B1 | 7/2002 | Ortiz et al. | |
| 6,537,314 B2 | 3/2003 | Langberg et al. | |
| 6,569,198 B1 | 5/2003 | Wilson et al. | |
| 6,585,716 B2 | 7/2003 | Altman | |
| 6,602,288 B1 | 8/2003 | Cosgrove et al. | |
| 6,648,874 B2 * | 11/2003 | Parisi et al. | 604/525 |
| 6,656,221 B2 | 12/2003 | Taylor et al. | |
| 6,827,731 B2 | 12/2004 | Armstrong et al. | |
| 2001/0018611 A1 | 8/2001 | Solem et al. | |
| 2001/0044568 A1 | 11/2001 | Langberg et al. | |
| 2001/0052345 A1 | 12/2001 | Niazi | |
| 2002/0016628 A1 | 2/2002 | Langberg et al. | |
| 2002/0087173 A1 * | 7/2002 | Alferness et al. | 606/151 |
| 2002/0103532 A1 | 8/2002 | Langberg et al. | |
| 2002/0103533 A1 | 8/2002 | Langberg et al. | |
| 2002/0151961 A1 | 10/2002 | Lashinshi et al. | |
| 2002/0169502 A1 | 11/2002 | Mathis | |
| 2002/0169504 A1 | 11/2002 | Alferness et al. | |
| 2003/0069636 A1 | 4/2003 | Solem et al. | |
| 2003/0083538 A1 | 5/2003 | Adams et al. | |
| 2003/0093148 A1 | 5/2003 | Bolling et al. | |
| 2003/0105520 A1 | 6/2003 | Alferness et al. | |

FOREIGN PATENT DOCUMENTS

| | | |
|---|---|---|
| EP | 0 756 853 A1 | 2/1997 |
| JP | 409322936 A | 12/1997 |
| WO | WO 98/22159 | 5/1998 |
| WO | WO 00/62708 A1 | 10/2000 |
| WO | WO 01/00111 A1 | 1/2001 |
| WO | WO 01/54618 A1 | 8/2001 |
| WO | WO 02/053206 A2 | 7/2002 |
| WO | WO 02/060352 A1 | 8/2002 |
| WO | WO 02/062270 A1 | 8/2002 |
| WO | WO02062263 A2 * | 8/2002 |
| WO | WO 02/091908 A2 | 11/2002 |
| WO | WO 02/100240 A2 | 12/2002 |
| WO | WO 03/037171 A2 | 5/2003 |

OTHER PUBLICATIONS

Davila, Julio C. et al., Circumferential Suture of The Mitral Valve for the Correction of Regurgitation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

Beardow, Andrew W. et al., Chronic Mitral Valve Disease in Cavalier King Charles Spaniels: 95 Cases (1987-1991), JAVMA, vol. 203, No. 7, Oct. 1, 1993, pp. 1023-1029.

Buchanan, James W., Circumferential Suture of the Mitral Annulus for Correction of Mitral Regurgitation in Dogs, Veterinary Surgery, 1998, pp. 182-193.

Kerstetter, Kyle K. et al., Short-Term Hemodynamic Evaluation of Circumferential Mitral Annuloplasty for Correction of Mitral Valve Regurgitation in Dogs, Veterinary Surgery, 1998, pp. 216-223.

Davila, Julio C. et al., Circumferential Suture of The Mitral Ring, 18 pages.

* cited by examiner

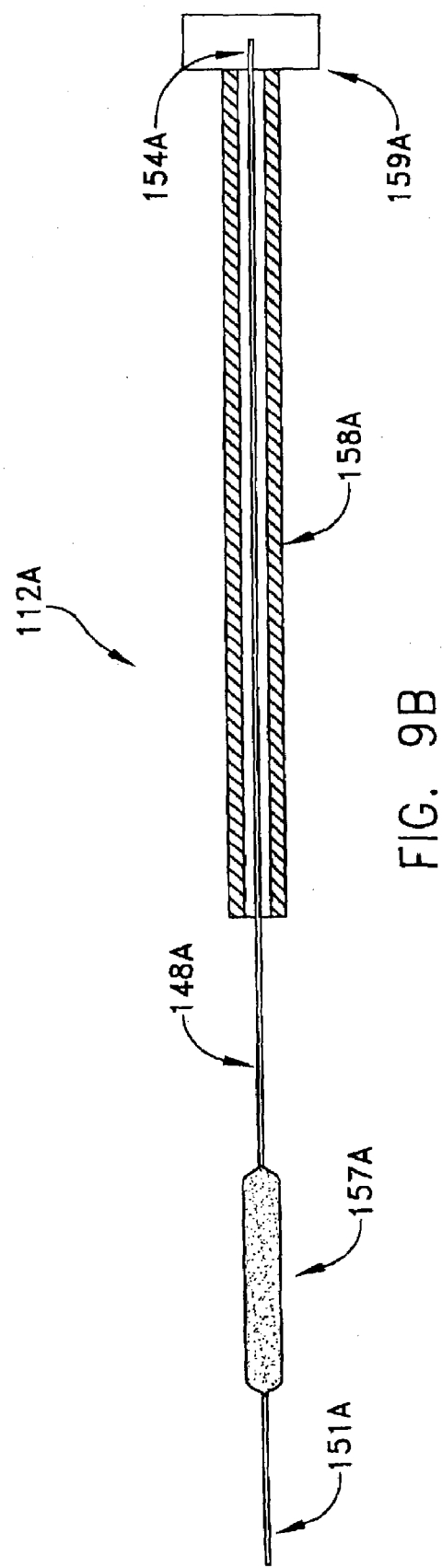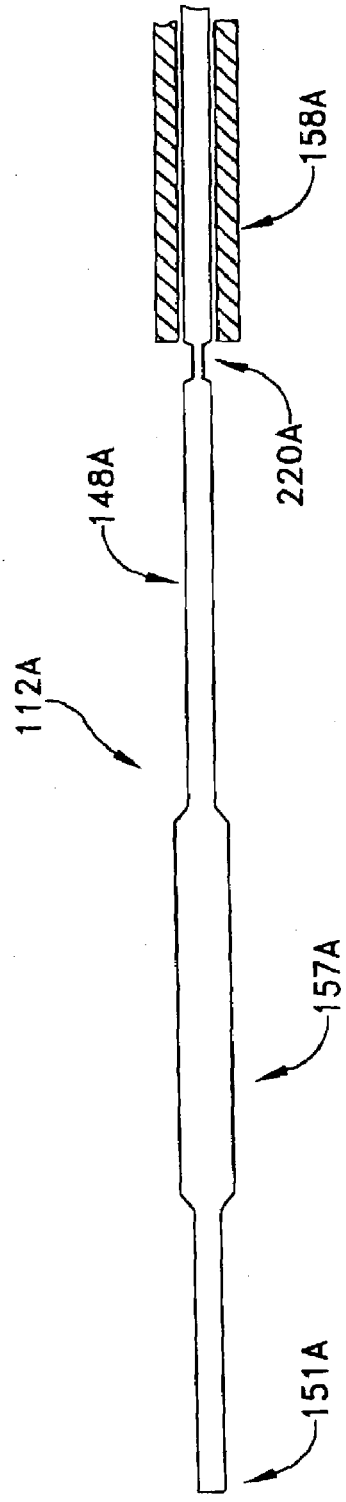
FIG. 9B
FIG. 9C

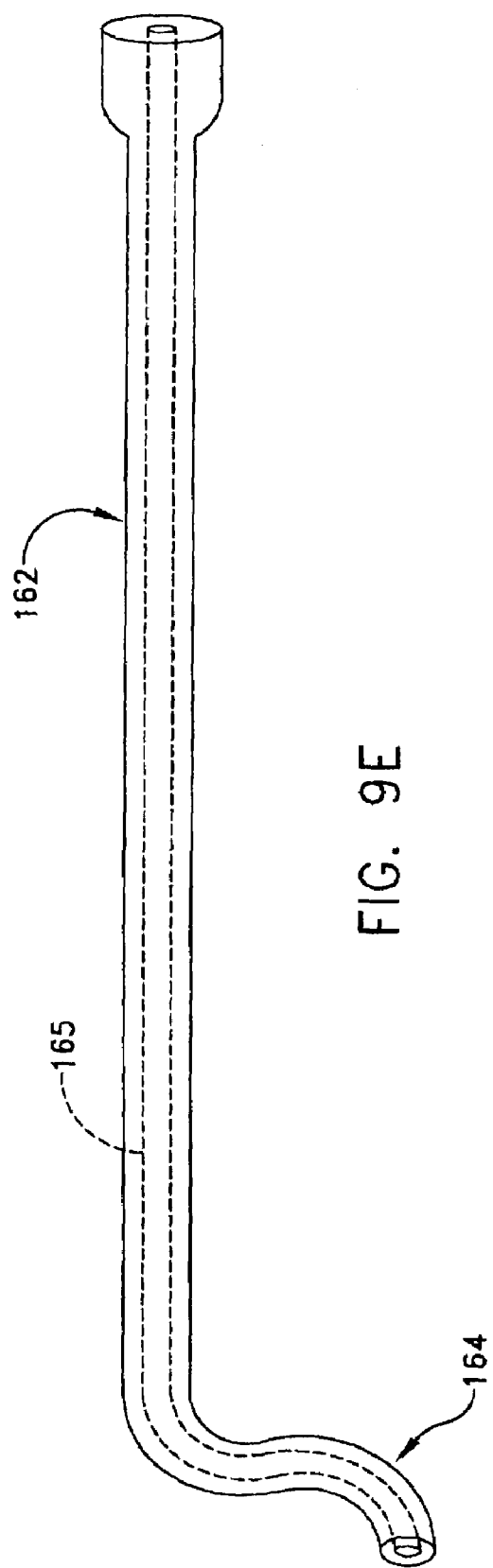

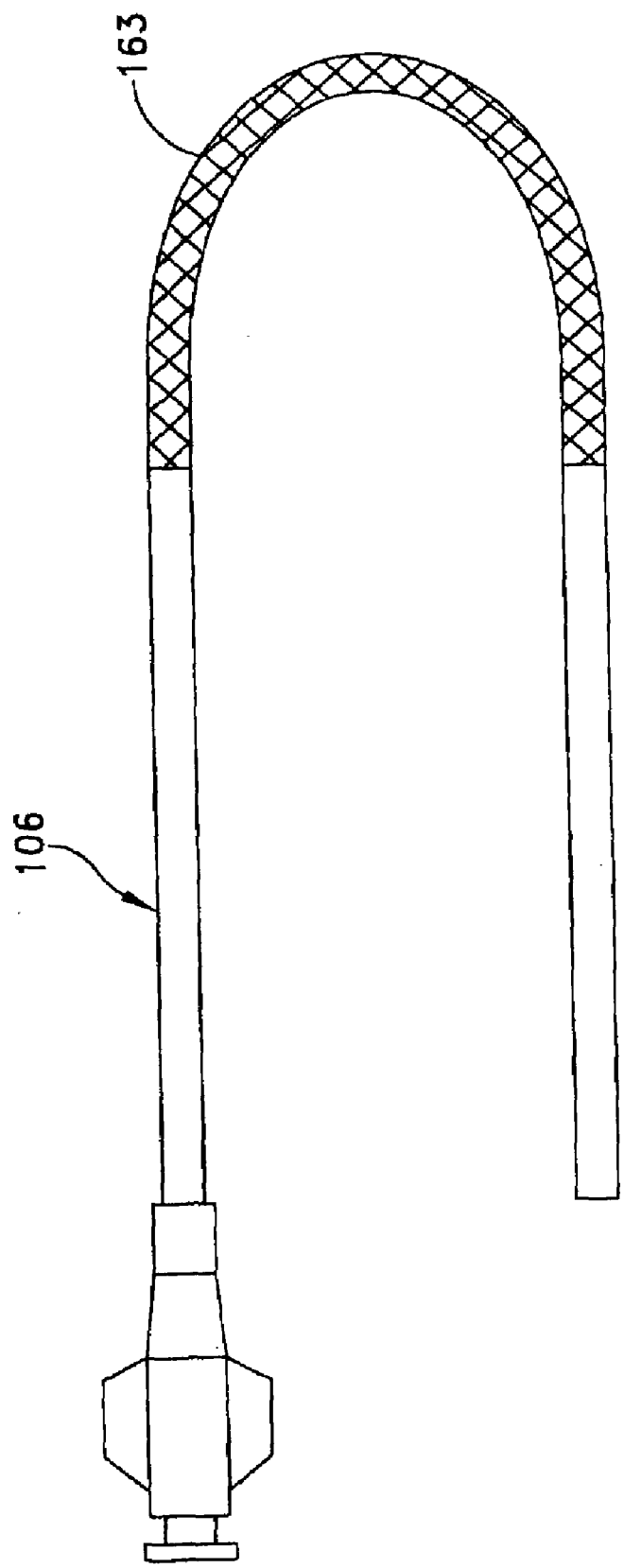

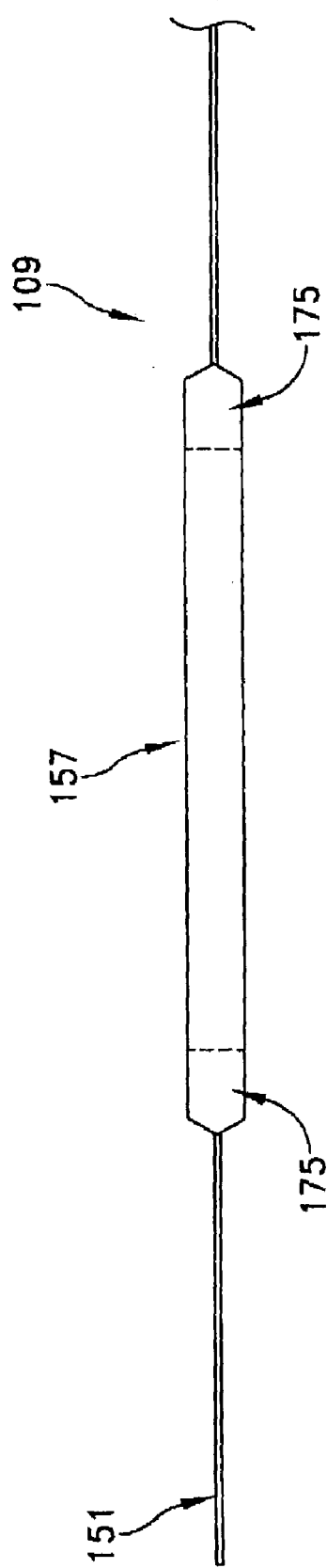
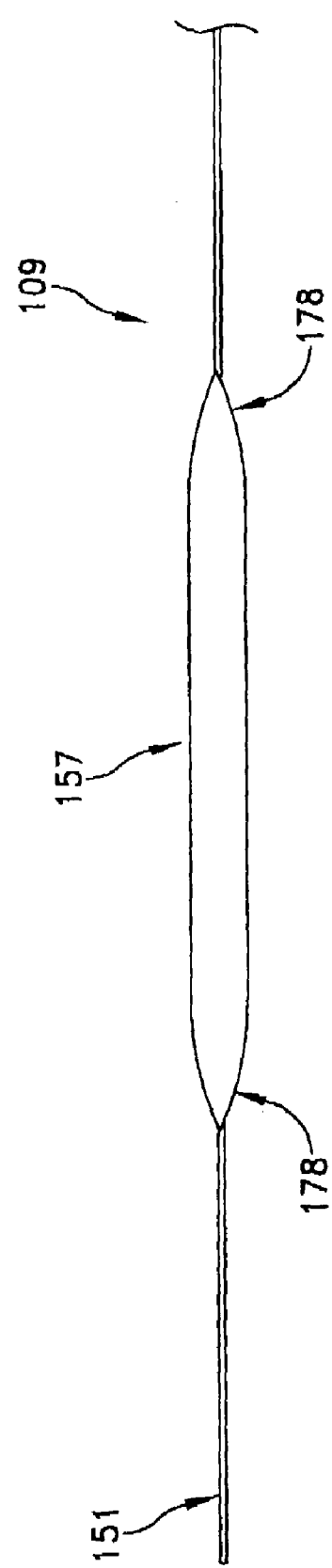

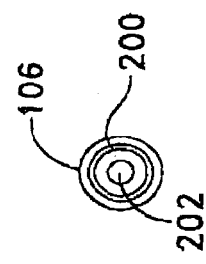
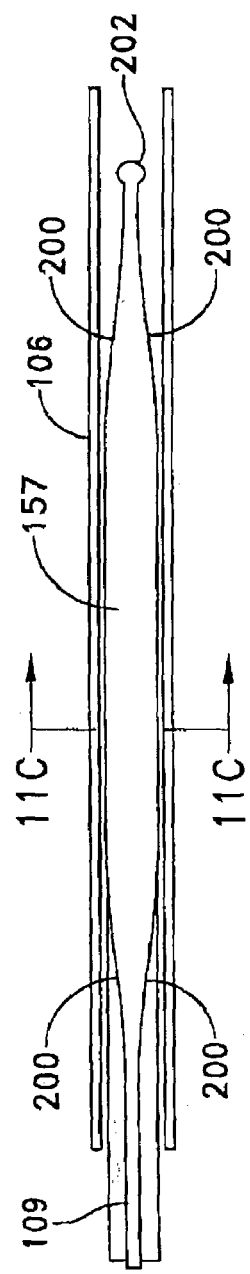

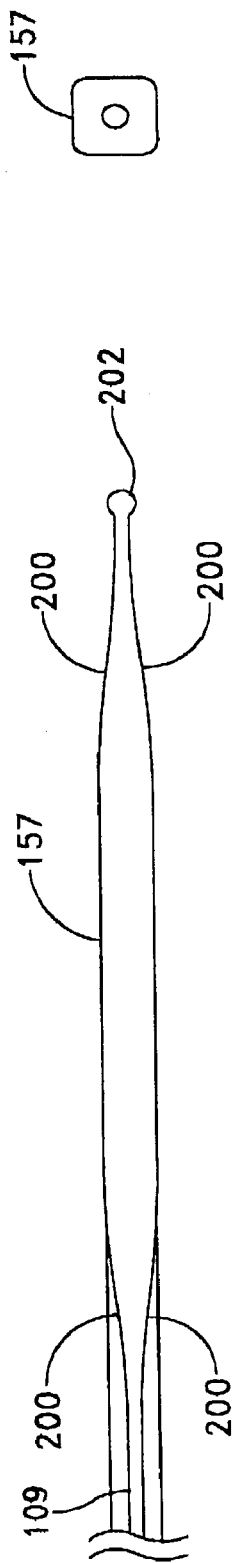

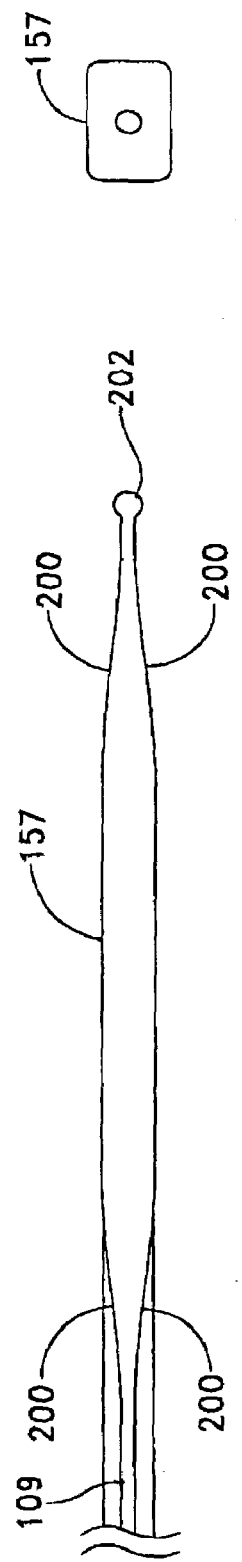

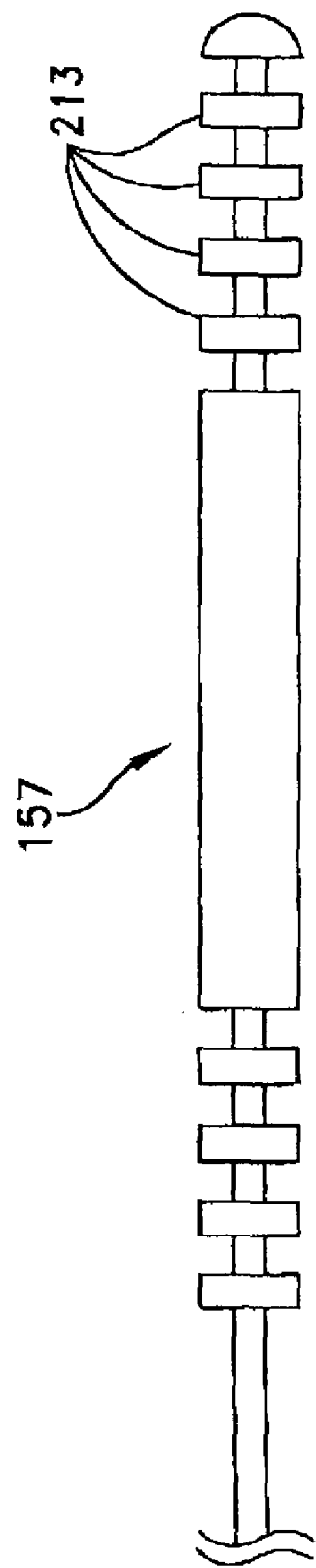

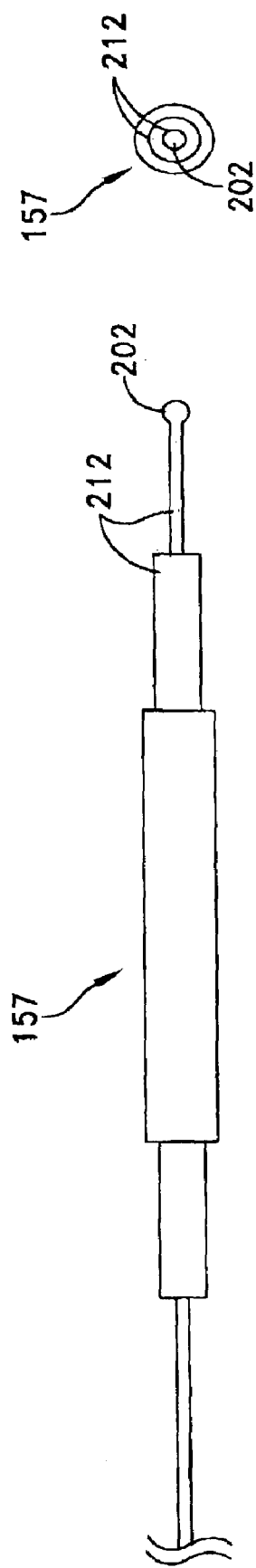

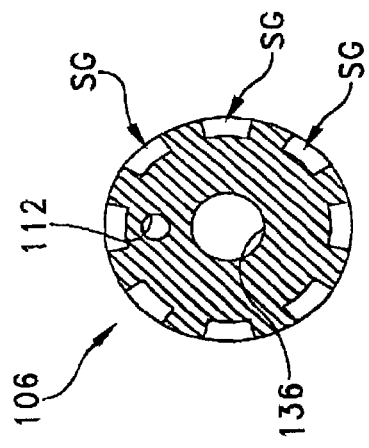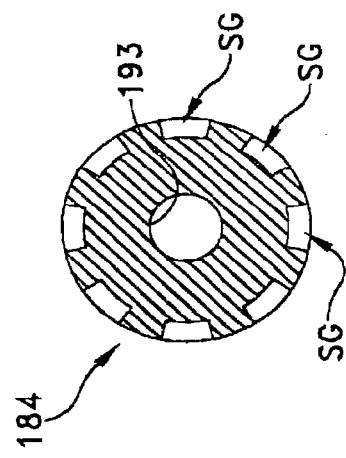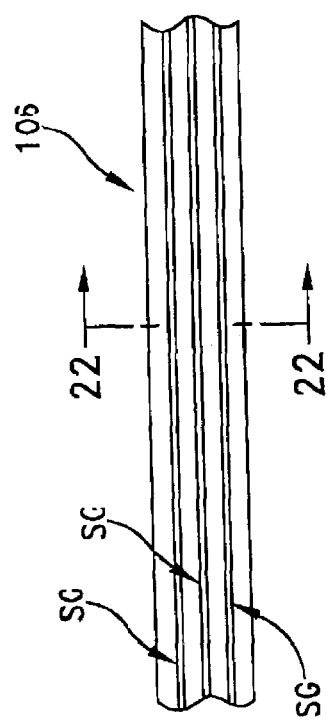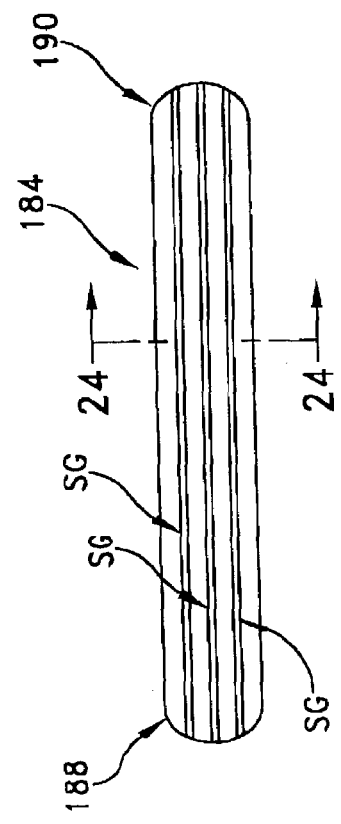

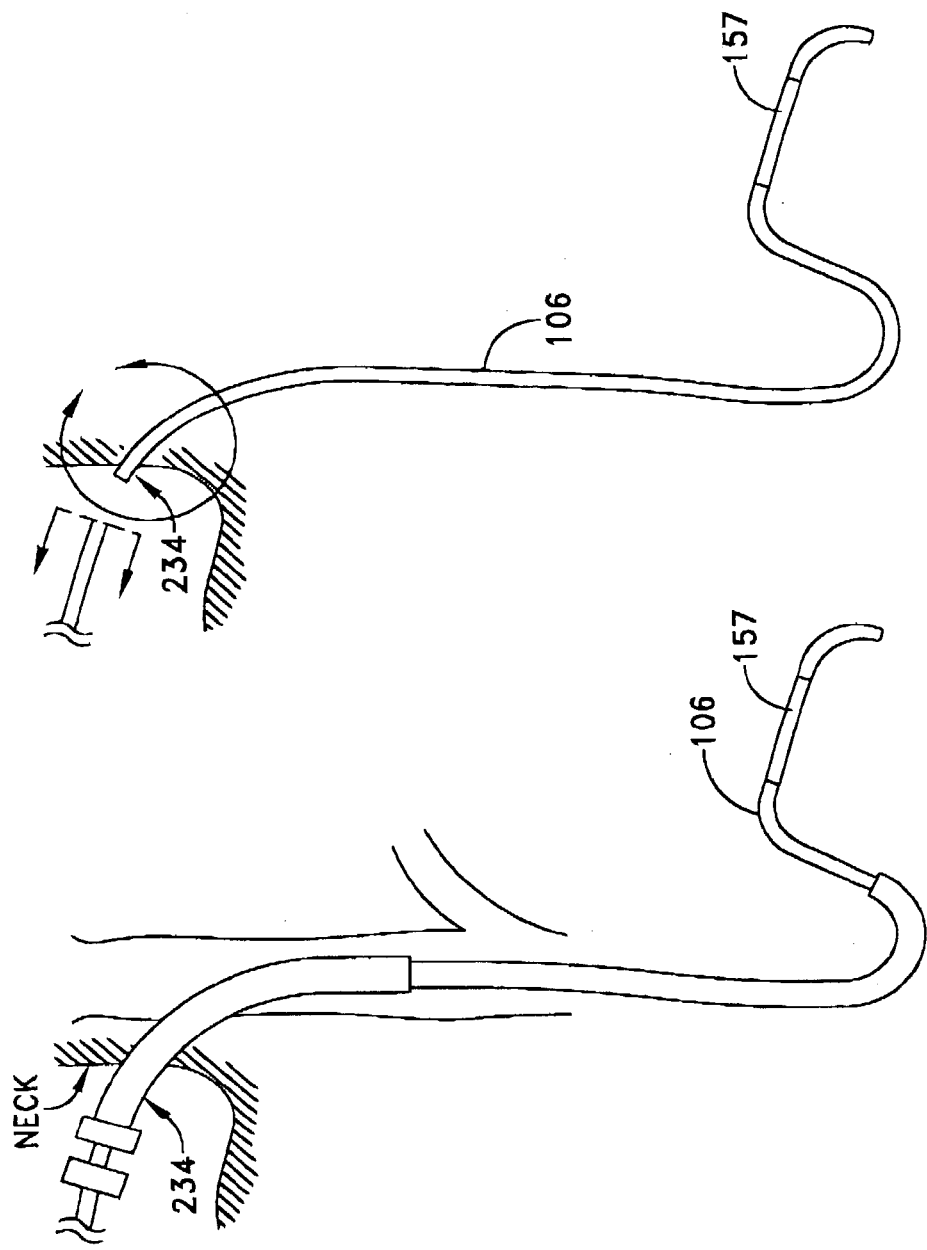

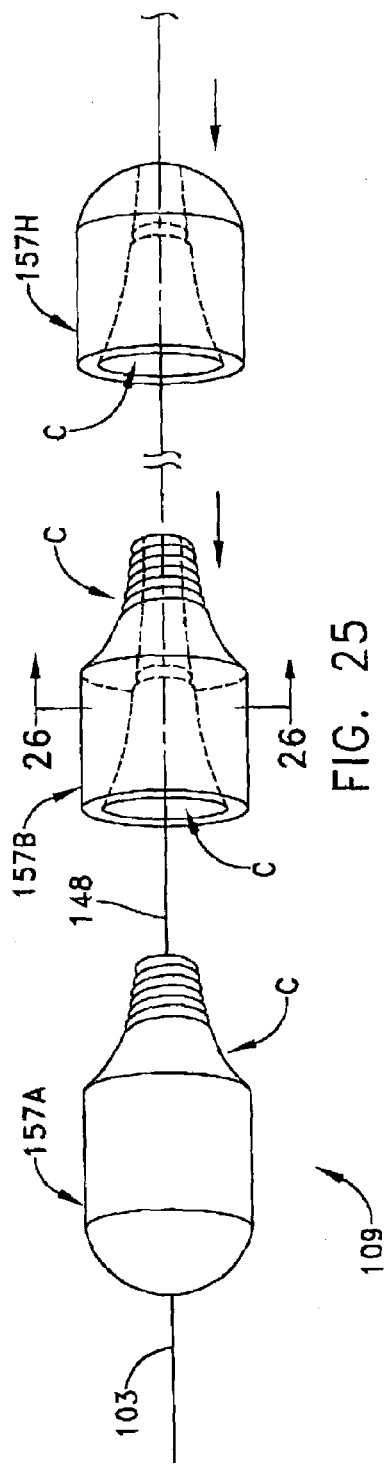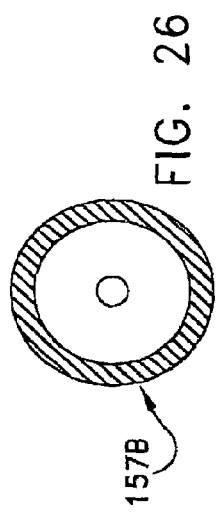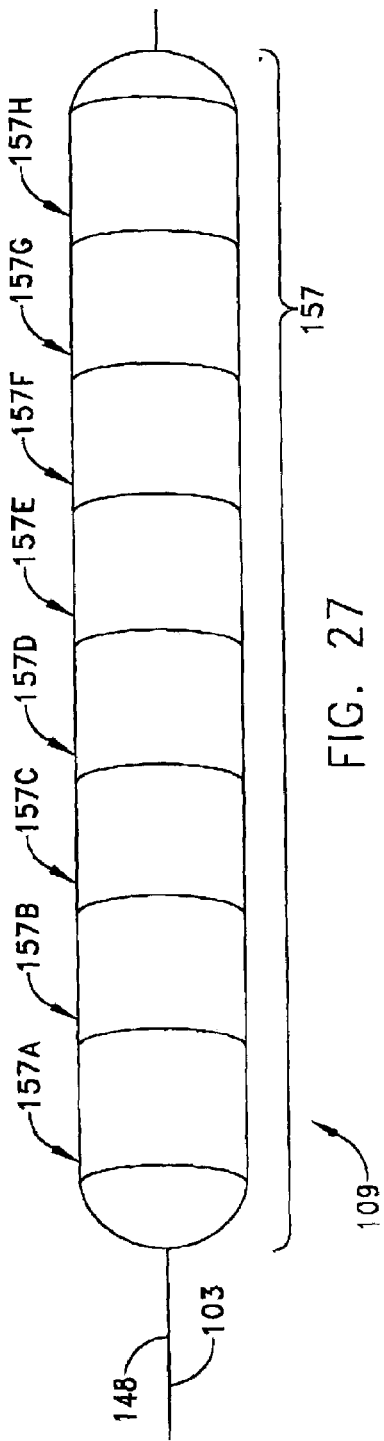

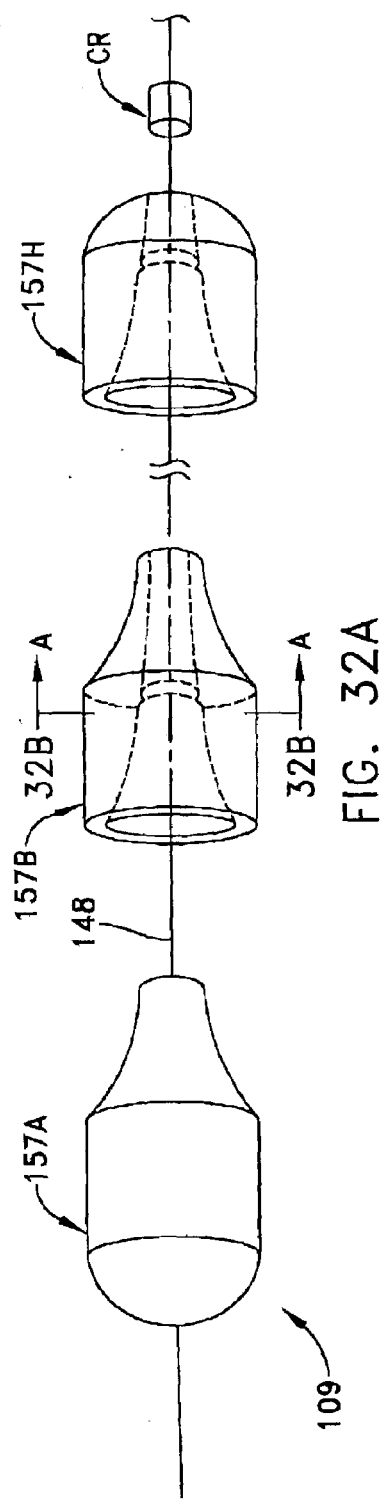
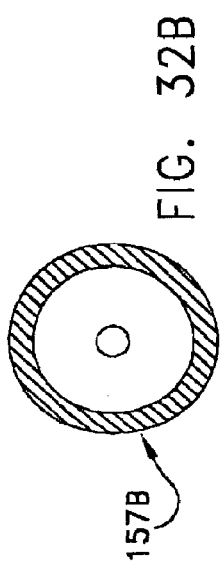
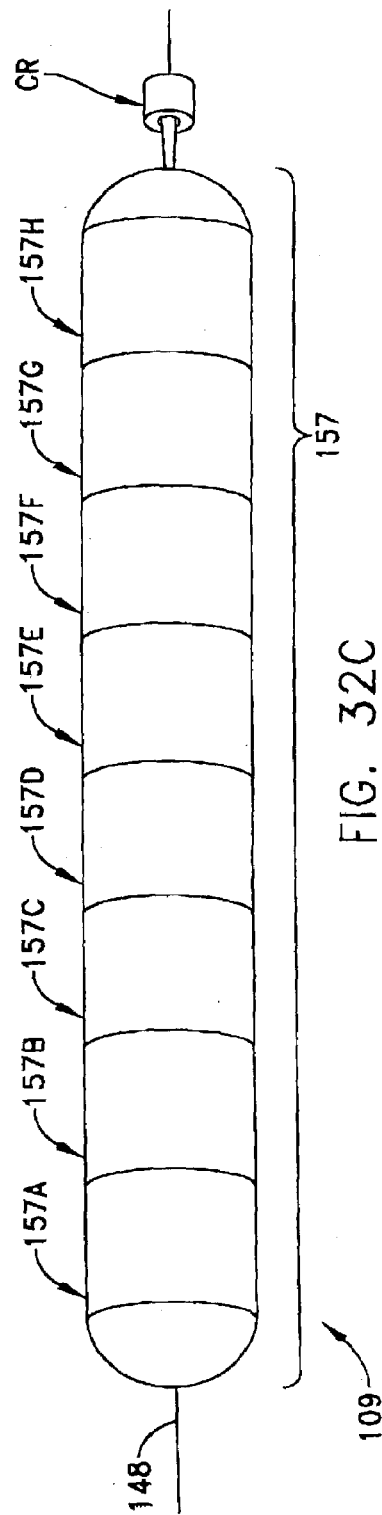
FIG. 32A
FIG. 32B
FIG. 32C

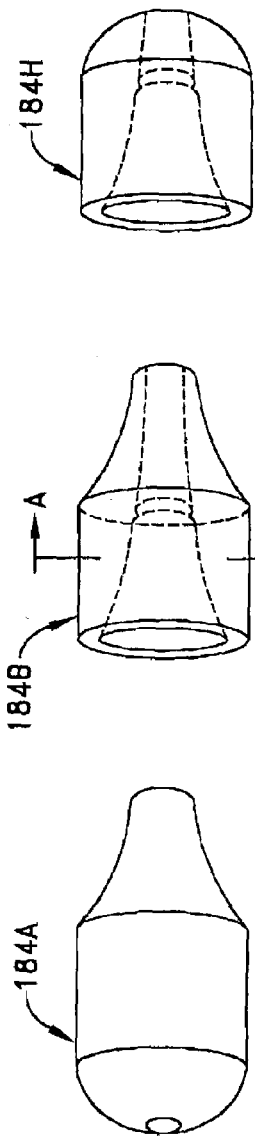
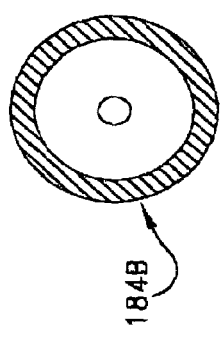
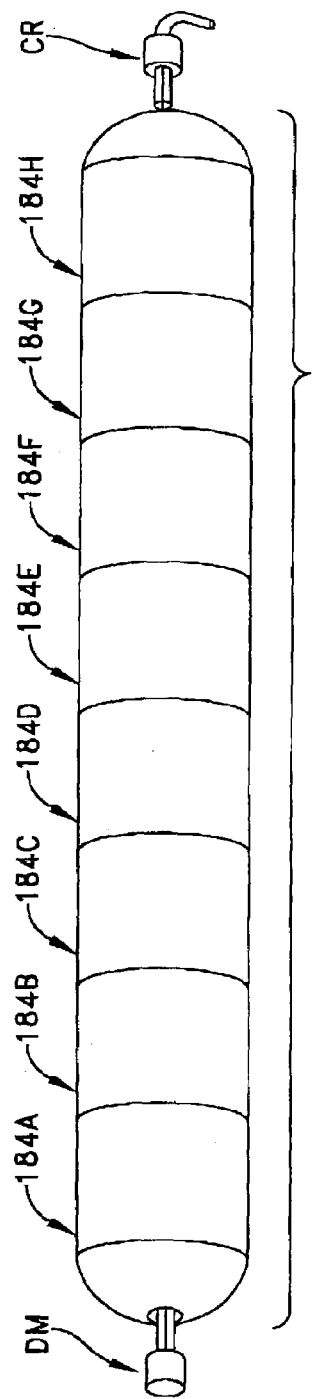
FIG. 37A
FIG. 37B
FIG. 37C

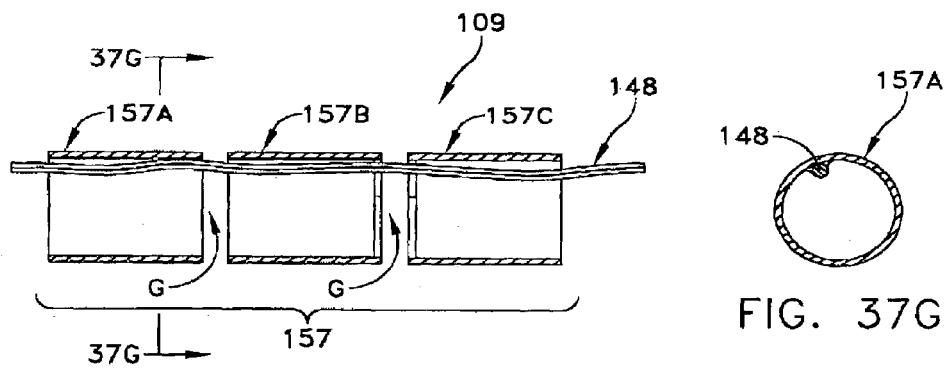
FIG. 37F
FIG. 37G
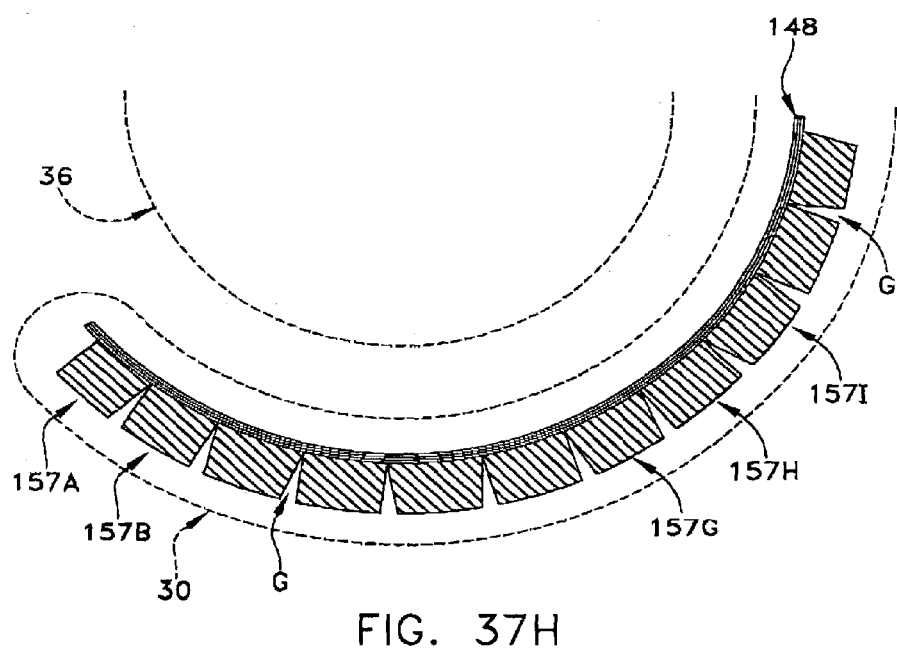
FIG. 37H
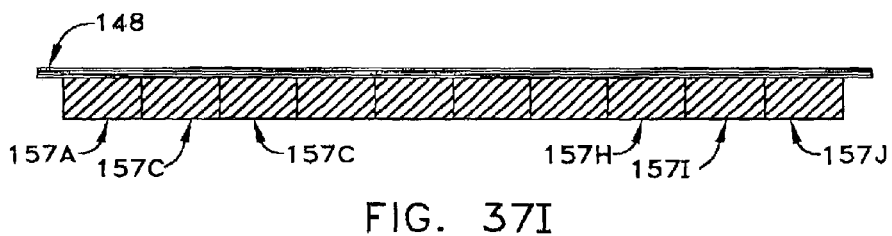
FIG. 37I

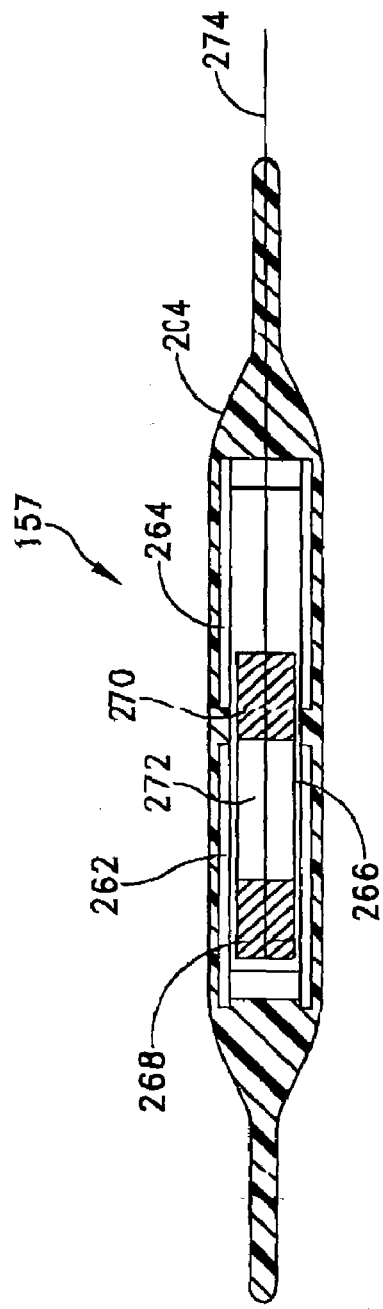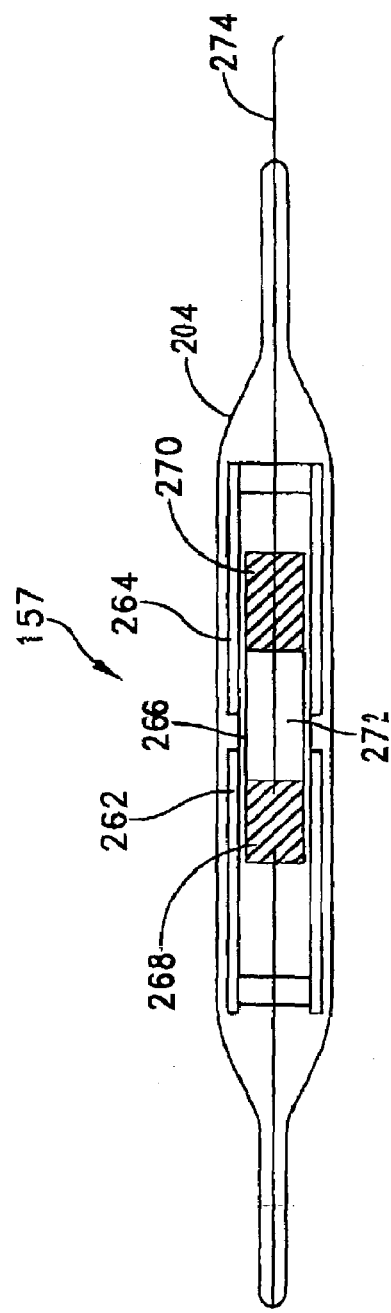

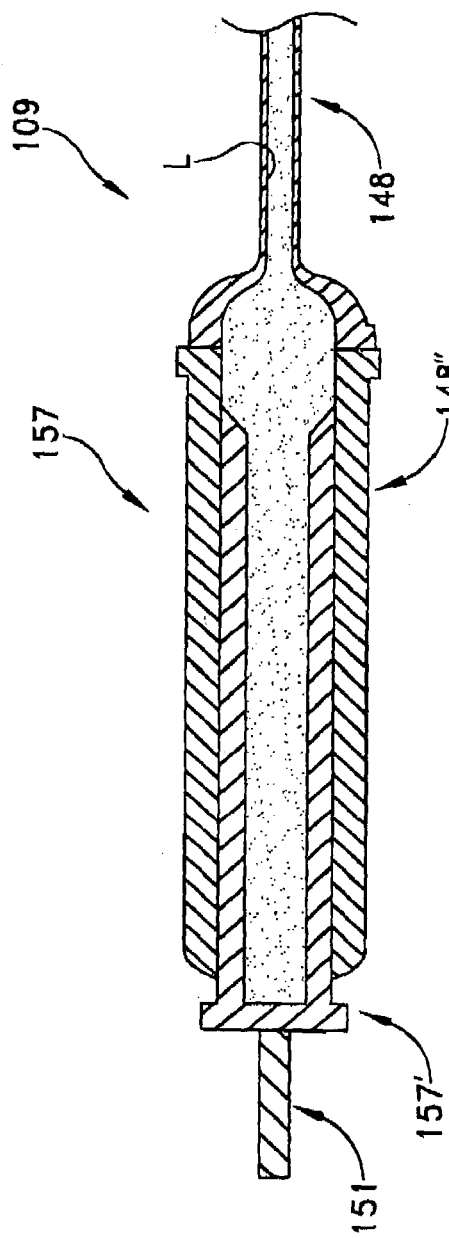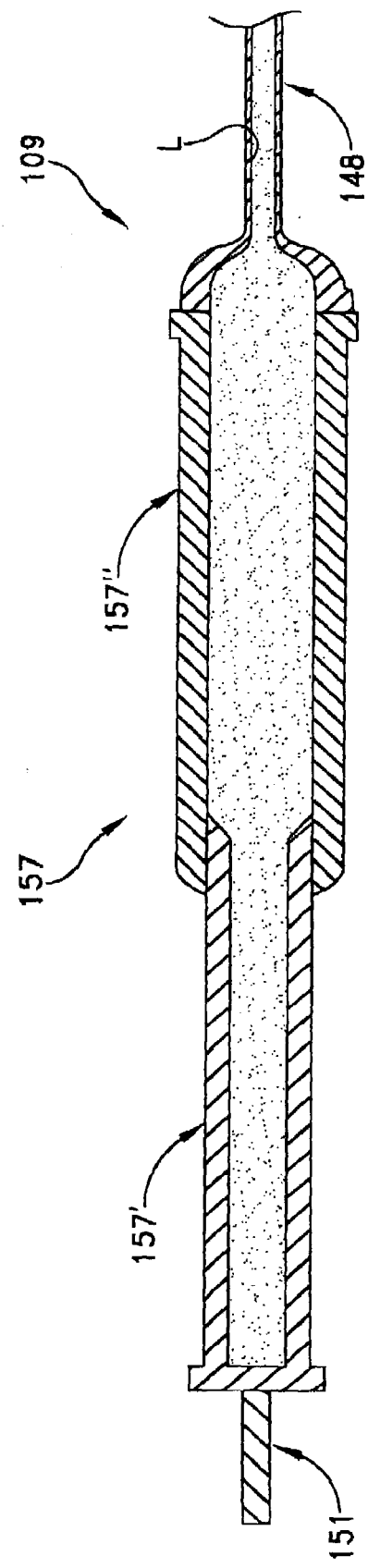

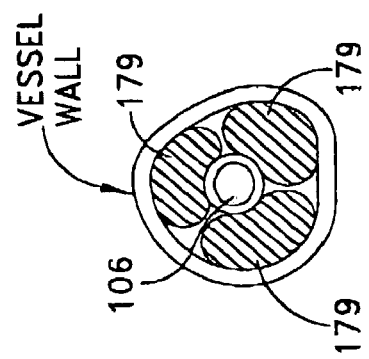
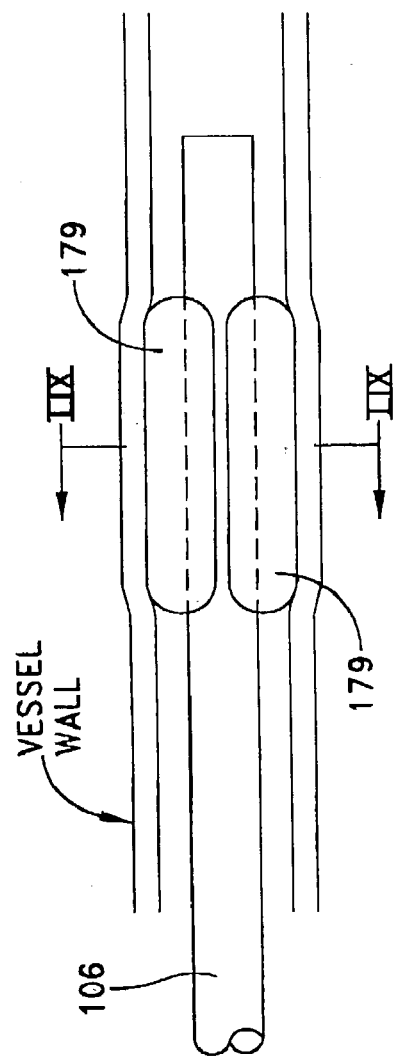

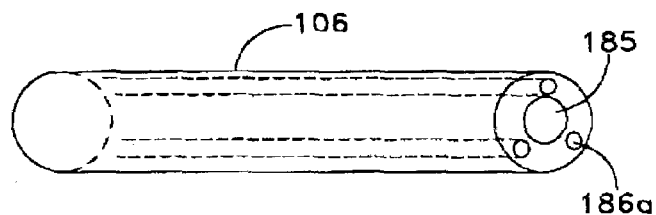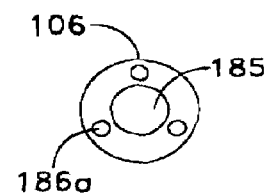
FIG. 65  FIG. 66
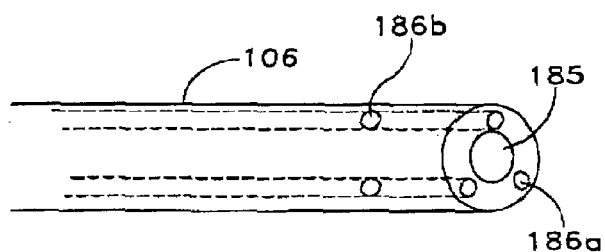
FIG. 67
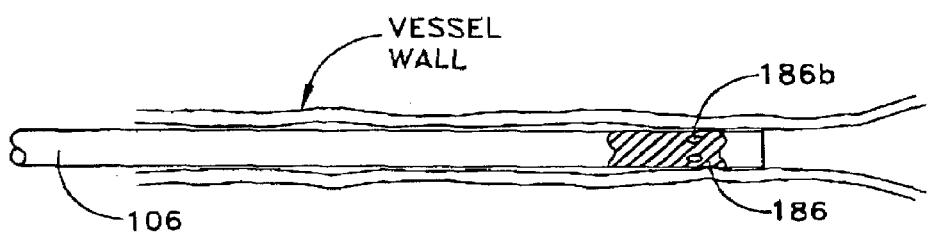
FIG. 68

METHOD AND APPARATUS FOR REDUCING MITRAL REGURGITATION

REFERENCE TO PENDING PRIOR PATENT APPLICATIONS

This patent application:

(1) is a continuation-in-part of prior U.S. patent application Ser. No. 10/068,264, filed Feb. 05, 2002 by Daniel C. Taylor et al. for METHOD AND APPARATUS FOR IMPROVING MITRAL VALVE FUNCTION, now U.S. Pat. No. 6,656,221;

(2) is a continuation-in-part of prior U.S. patent application Ser. No. 10/112,354, filed Mar. 29, 2002 by John Liddicoat et al. for METHOD AND APPARATUS FOR IMPROVING MITRAL VALVE FUNCTION now U.S. Pat. No. 7,186,264;

(3) is a continuation-in-part of pending prior U.S. patent application Ser. No. 10/218,649, filed Aug. 14, 2002 by Daniel C. Taylor et al. for METHOD AND APPARATUS FOR IMPROVING MITRAL VALVE FUNCTION;

(4) claims benefit of prior U.S. patent application Ser. No. 10/280,401 filed Oct. 25, 2002 by William E. Cohn et al. for METHOD AND APPARATUS FOR REDUCING MITRAL REGURGITATION, now U.S. Pat. No. 7,052,487; and (5) claims benefit of prior U.S. Provisional Patent Application Ser. No. 60/348,424, filed Jan. 14, 2002 by Daniel C. Taylor et al. for METHOD AND APPARATUS TO IMPROVE MITRAL VALVE FUNCTION.

The aforementioned five (5) patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in incomplete coaptation of the mitral leaflets during systole. In this situation, mitral regurgitation is corrected by plicating the mitral valve annulus, either by sutures alone or by sutures in combination with a support ring, so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to pull the annulus back into a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longevity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

SUMMARY OF THE INVENTION

As a result, one object of the present invention is to provide improved methods and apparatus for reducing mitral regurgitation.

Another object of the present invention is to provide methods and apparatus for reducing mitral regurgitation which is minimally invasive.

Another object of the present invention is to provide methods and apparatus for reducing mitral regurgitation which can be deployed either permanently (e.g., for patients suffering from heart failure) or temporarily (e.g., for patients suffering from mitral regurgitation with acute myocardial infarction).

With the above and other objects in view, a feature of the present invention is the provision of a novel method for reducing mitral regurgitation. The method comprises the steps of inserting a flexible guiding catheter into a coronary sinus of a patient in a vicinity of a posterior leaflet of a mitral valve, anchoring a distal end of the catheter in the coronary sinus, moving an elongated body through the catheter and into a position within the catheter and in the vicinity of the posterior leaflet, the body being adapted to straighten a natural curvature of at least a portion of the coronary sinus in the vicinity of the posterior leaflet of the mitral valve, to move the posterior annulus anteriorly and thereby improve leaflet coaptation.

In accordance with a further feature of the invention, there is provided a further method for reducing mitral regurgitation. The method comprises the steps of advancing a guidewire into a coronary sinus of a patient, advancing a catheter around the guidewire and into the coronary sinus, providing a push rod having an elongated substantially rigid body fixed to a distal portion thereof, advancing the push rod through the catheter until the body is in a vicinity of a posterior leaflet of a mitral valve of the patient, detaching a proximal portion of the catheter from a distal portion of the catheter, and detaching a proximal portion of the push rod from a distal portion of the push rod, and removing the proximal portions of the catheter and the push rod from the patient.

In accordance with a further feature of the present invention, there is provided a further method for reducing mitral regurgitation. The method comprises the steps of advancing a flexible strand into a coronary sinus, anchoring at least a distal end of the strand in the coronary sinus proximate an anterior interventricular vein, interconnecting a proximal end of the strand and a cinch activation structure, and operating the cinch activation structure to pull the strand taut, whereby to cause the strand to approach a straight configuration and a mid-portion of the strand to engage a posterior wall of a mitral valve annulus, which pushes a posterior mitral valve leaflet anteriorly to improve coaptation.

In accordance with a further feature of the present invention, there is provided a novel assembly for reducing mitral regurgitation, the assembly comprising a flexible guiding catheter for insertion into a coronary sinus of a patient in a vicinity of a posterior leaflet of a mitral valve, structure for anchoring a distal end of the catheter in the coronary sinus, an elongated body for moving through the catheter and into a position within the catheter and in the vicinity of the posterior leaflet, the body being adapted to straighten a natural curvature of at least a portion of the coronary sinus in the vicinity of the posterior leaflet of the mitral valve, to move the posterior leaflet anteriorly and thereby improve leaflet coaptation.

In accordance with a further feature of the present invention, there is provided another assembly for reducing mitral regurgitation. The assembly comprises a flexible catheter having as a part thereof an elongated substantially rigid portion, the catheter being adapted for insertion into a coronary sinus of a patient and adapted to be moved to a position placing the rigid portion in a vicinity of a posterior leaflet of a mitral valve, the rigid portion being adapted to straighten a natural curvature of at least a portion of the coronary sinus in the vicinity of the posterior leaflet of the mitral valve, to move the posterior leaflet anteriorly and thereby improve leaflet coaptation.

In accordance with a still further feature of the present invention, there is provided another assembly for reducing mitral regurgitation. The assembly comprises a flexible guide wire for insertion into a coronary sinus of a patient, a flexible guiding catheter for disposition around the guide wire and adapted for insertion into the coronary sinus, an elongated substantially rigid body fixed to a distal end of a push rod and adapted to advance in the catheter to a vicinity of a posterior leaflet of a mitral valve of the patient, a detachable joint by which the push rod may be separated, and a break-away joint by which the catheter may be separated into distal and proximal portions, whereby after the body is in the vicinity of the posterior leaflet, the push rod and the catheter proximal portions may be removed from the site and withdrawn from the patient.

In accordance with a still further feature of the present invention, there is provided another assembly for reducing mitral regurgitation. The assembly comprises a flexible strand adapted to advance into and through a coronary sinus, an anchor at a distal end of the strand for securing the distal end in a fixed position in the coronary sinus, and a cinch activation structure connected to a proximal portion of the strand and operable by an operator to pull the strand taut, whereby to cause the strand to approach a straight configuration with a mid-portion of the strand adapted to engage a posterior wall of a mitral valve annulus to urge a posterior mitral valve leaflet anteriorly to improve coaptation.

In accordance with a still further feature of the invention, there is provided an elongated body for introduction into a coronary sinus. The body comprises an elastomeric sleeve substantially closed at both ends thereof, the sleeve defining two internal chambers in axial alignment with each other, the chambers being separated by a wall having a aperture therein. A rod is slidably disposed in the aperture and enters into the two chambers, the rod having a distal flexible portion, a middle rigid portion and a proximal flexible portion. A pull wire extends from the proximal end of the rod and through a proximal end of the sleeve. The rod is positionable such that one of the flexible portions of the rod is disposed in the aperture in the chamber wall, rendering the body flexible. The rod is further positionable by manipulation of the pull wire to cause the rod rigid portion to be disposed in the aperture in the chamber wall, rendering the wall rigid. Thus, the body may be rendered flexible so as to be moved to the coronary sinus and may be rendered rigid so as to effect a change in coronary leaflet coaptation.

In accordance with a still further feature of the invention, there is provided a method for reducing mitral regurgitation comprising inserting apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation.

In accordance with a still further feature of the invention, there is provided an apparatus for reducing mitral regurgitation comprising a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation.

Significantly, the present invention may be practiced in a minimally invasive manner, either permanently or temporarily, so as to reduce mitral regurgitation.

The above and other features of the invention, including various novel details of construction and combinations of parts and method steps, will now be more particularly described with reference to the accompanying drawings and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein like numbers refer to like parts and further wherein:

FIG. 9B is a diagrammatic side elevational partly sectioned view of a further flexible push rod;

FIGS. 9C and 9D are similar to FIG. 9B and showing alternative embodiments of flexible push rod;

FIG. 9E is a generally side elevational view of a flexible support catheter;

FIG. 9F is a generally side elevational view of an alternative flexible delivery catheter;

FIGS. 10 and 11 show alternative constructions for the straight, substantially rigid elongated body;

FIGS. 11A-11N and 11P-11S illustrate other aspects of the present invention;

FIGS. 21–24 illustrate other aspects of the present invention;

FIGS. 24B-24H and 24J-24O illustrate alternative features of the invention;

FIGS. 25–27 illustrate another form of the present invention;

FIGS. 32A–32E illustrate other aspects of the present invention;

FIGS. 37A–37C illustrate another aspect of the present invention;

FIGS. 37F–37I illustrate another aspect of the present invention;

FIGS. 37L and 37M are sectional views of a further embodiment of the substantially rigid elongated body; illustrate yet another aspect of the present invention;

FIGS. 41 and 42 illustrate yet another form of the present invention;

FIGS. 45–75 are diagrammatic views illustrating alternative methods and apparatus for anchoring components in place;

DETAILED DESCRIPTION OF THE PREFERRED EMBODIMENTS

Figure 1:
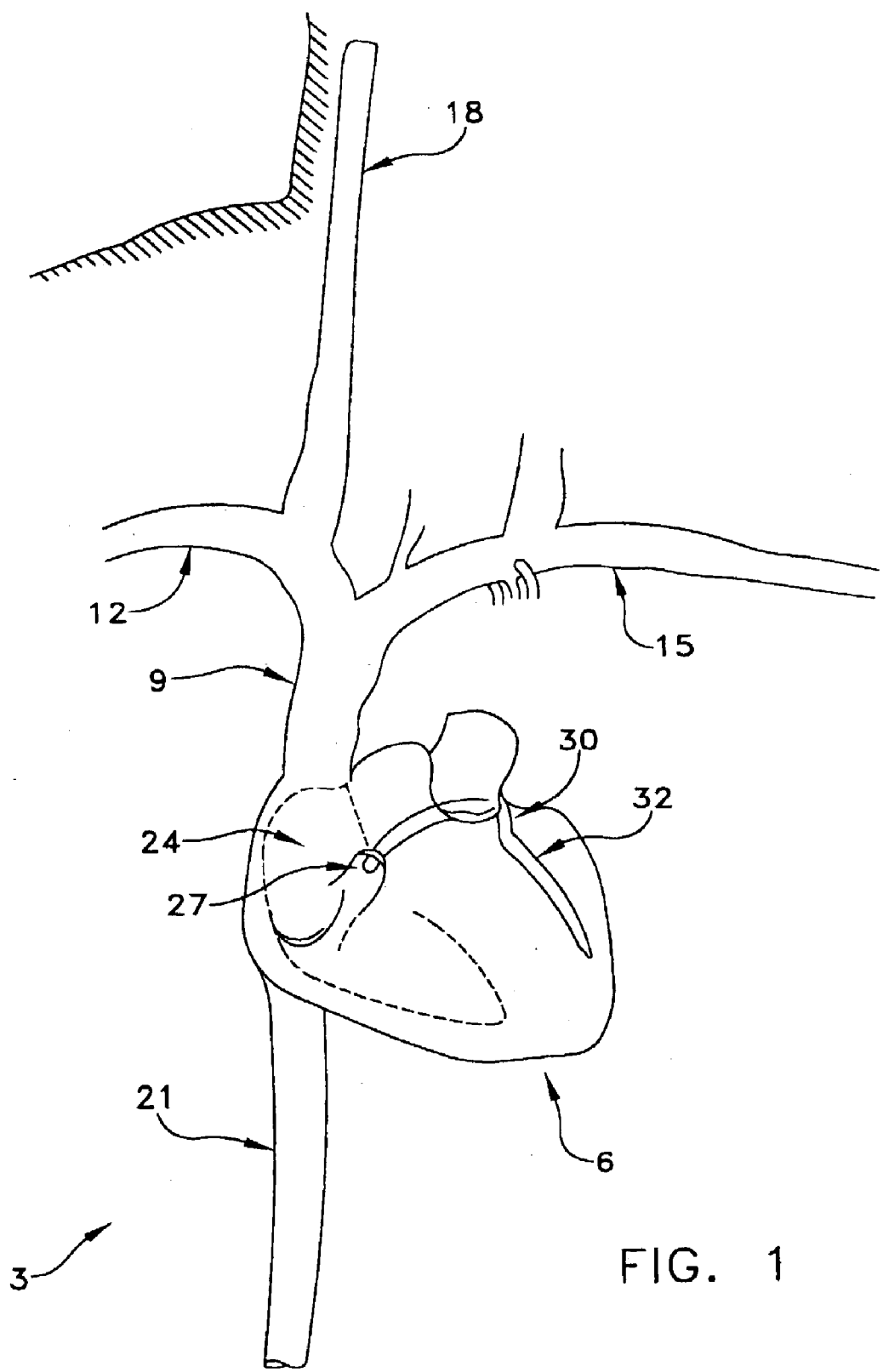
FIG. 1 is a schematic view of portions of the human vascular system.

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this anatomic relationship. More particularly, by deploying novel apparatus in the coronary sinus, adjacent to the posterior leaflet of the mitral valve, the natural curvature of the coronary sinus may be modified in the vicinity of the posterior leaflet of the mitral valve, whereby to move the posterior annulus anteriorly so as to improve leaflet coaptation and, as a result, reduce mitral regurgitation.

In one preferred embodiment of the invention, the novel apparatus comprises a straight, substantially rigid elongated body, the length of the straight, substantially rigid elongated body being sized so that when the straight, substantially rigid body is positioned in the coronary sinus in the vicinity of the posterior leaflet of the mitral valve, the straight, substantially rigid elongated body causes at least a portion of the coronary sinus to assume a substantially straight configuration adjacent to the posterior leaflet of the mitral valve, whereby to move the posterior annulus anteriorly and thereby improve leaflet coaptation.

And in one preferred embodiment of the invention, access to the coronary sinus is gained percutaneously, e.g., the straight, substantially rigid elongated body is introduced into the patient's vascular system via the jugular vein or via the left subclavian vein, passed down the superior vena cava, passed through the right atrium and then passed into the coronary sinus, where it is deployed. Alternatively, the straight, substantially rigid elongated body may be introduced into the coronary sinus through a small incision in the heart, or through some other incision into the patient's vascular system.

And in one preferred embodiment of the invention, the straight, substantially rigid elongated body is guided into position by (i) passing it through a pre-positioned catheter, and/or (ii) passing it over a pre-positioned guidewire, and/or (iii) passing it guide-free (e.g., on the end of a steerable delivery tool) to the surgical site.

Once deployed, the novel apparatus may be left in position permanently (e.g., in the case of patients suffering from mitral regurgitation associated with heart failure) or the novel apparatus may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Figure 2:
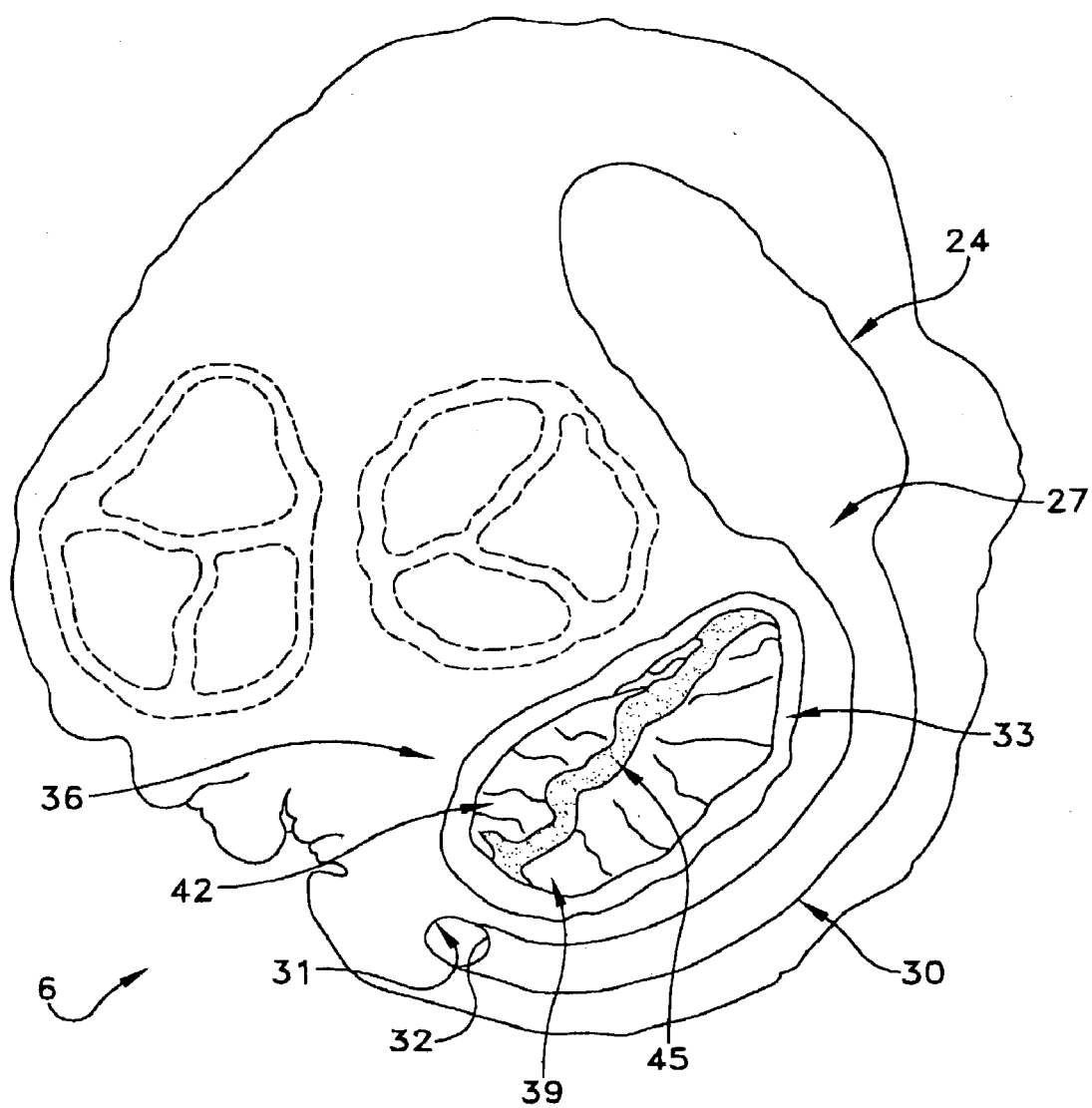
FIG. 2 is a schematic view of portions of the human heart.

Looking now at FIGS. 1 and 2, there are shown aspects of the cardiovascular system 3 of a patient. More particularly, cardiovascular system 3 generally comprises the heart 6, the superior vena cava 9 (FIG. 1), the right subclavian vein 12, the left subclavian vein 15, the jugular vein 18, and the inferior vena cava 21. Superior vena cava 9 and inferior vena cava 21 communicate with the heart's right atrium 24 (FIGS. 1 and 2). A coronary ostium 27 leads to a coronary sinus 30. At a far end 31 (FIG. 2) of coronary sinus 30, the vascular structure leads to a vertically-descending anterior interventricular vein ("AIV") 32. For purposes of the present invention, it is convenient to consider the term "coronary sinus" to mean the vascular structure extending between coronary ostium 27 and AIV 32.

As seen in FIG. 2, between coronary ostium 27 and AIV 32, coronary sinus 30 generally extends substantially adjacent to a posterior perimeter of an annulus 33 of a mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which will permit regurgitation.

Figure 3:
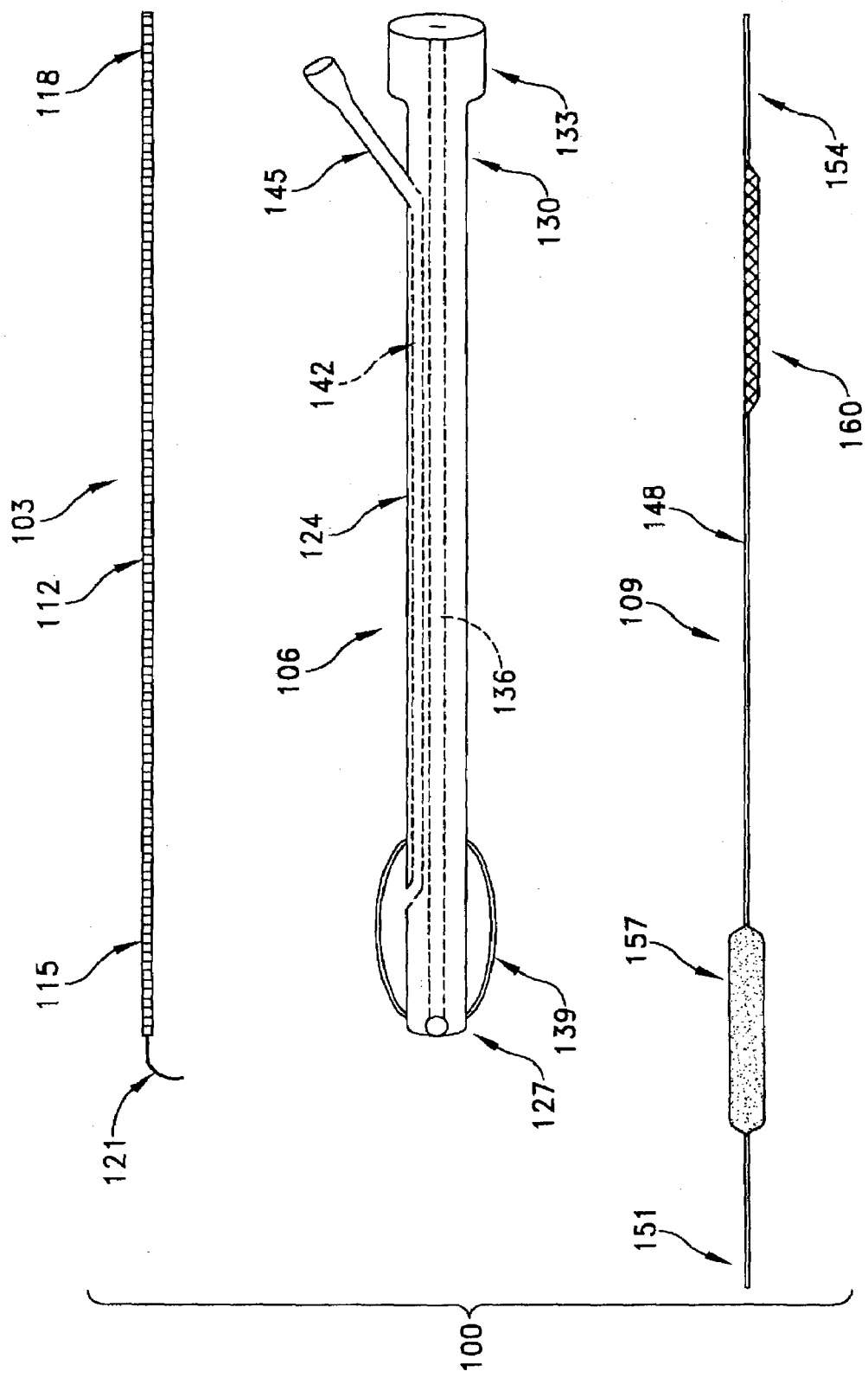
FIG. 3 is a schematic view of a preferred system formed in accordance with the present invention.

Looking next at FIG. 3, there is shown a system 100 which comprises one preferred embodiment of the present invention. More particularly, system 100 generally comprises a guidewire 103, a delivery catheter 106 and a push rod 109.

Guidewire 103 comprises a flexible body 112 having a distal end 115 and a proximal end 118. The distal end 115 of guidewire 103 preferably includes a spring tip 121 for allowing the distal end of guidewire 103 to atraumatically traverse vascular structures, i.e., while the guidewire 103 is being passed through the vascular system of a patient.

Delivery catheter 106 comprises a flexible body 124 having a distal end 127 and a proximal end 130, preferably with an adjustable valve 133 attached. A central lumen 136 extends from distal end 127 to proximal end 130. In some circumstances, it is desirable to provide a securing mechanism for securing the distal end 127 of the delivery catheter 106 within a vascular structure. By way of example, but not limitation, a balloon 139 may be positioned about the exterior of flexible body 124, just proximal to distal end 127, with an inflation lumen 142 extending between balloon 139 and an inflation fitting 145. Alternative means for securing the delivery catheter 106 within a vascular structure are discussed hereinafter.

Push rod 109 comprises a flexible body 148 having a distal end 151 and a proximal end 154. A straight, substantially rigid elongated body 157, which may have a variety of different lengths, is formed on flexible body 148, proximal to distal end 151. A removable proximal stiffener, or handle, 160 may be placed between straight, substantially rigid elongated body 157 and proximal end 154 to facilitate gripping flexible body 148, e.g., for advancement or retraction purposes.

System 100 may be used as follows to reduce mitral regurgitation.

Figure 4:
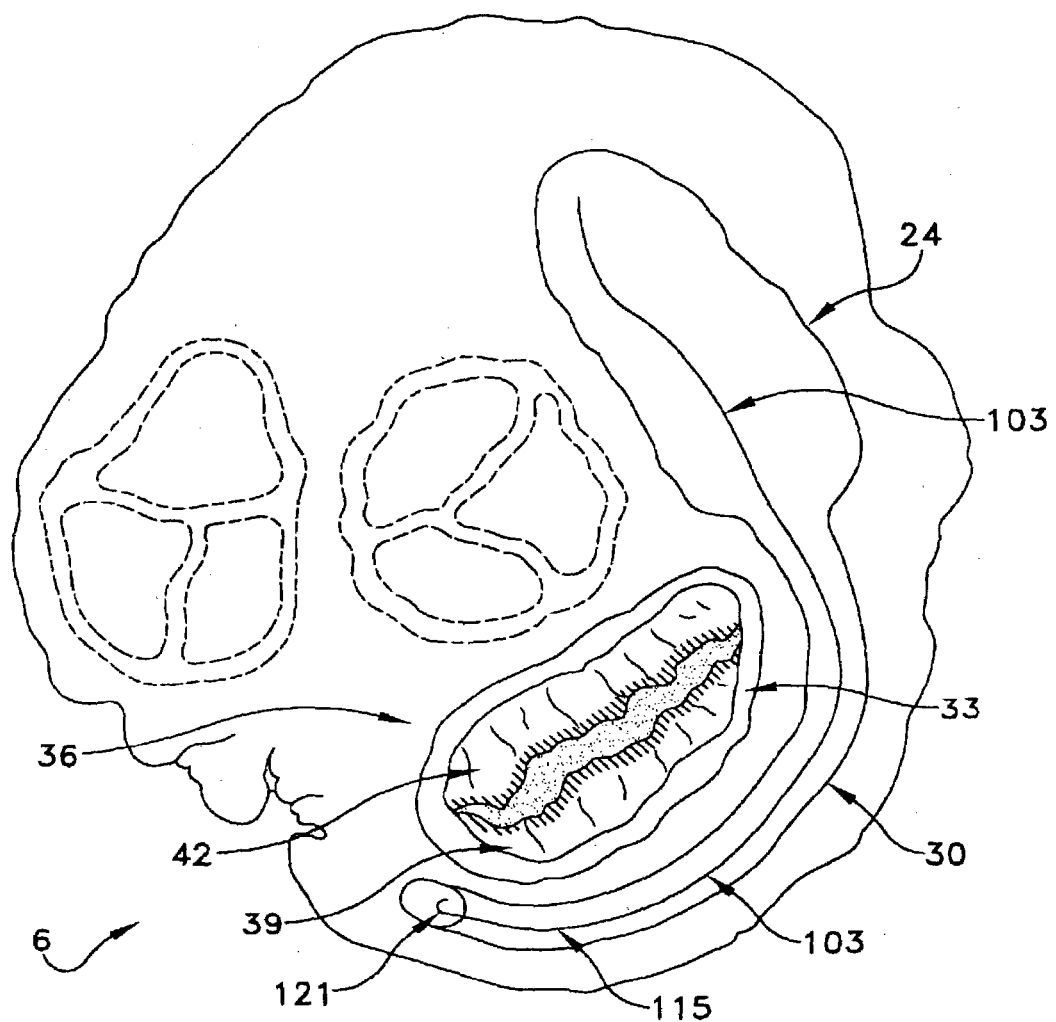
FIGS. 4–7 are a series of views illustrating use of the system of FIG. 3 to reduce mitral regurgitation.

First, distal end 115 of guidewire 103 is passed down the jugular vein 18 (or the left subclavian vein 15) of a patient, down superior vena cava 9, through right atrium 24 of the heart 6, and into the coronary sinus 30 (FIG. 4). It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 helps ensure minimal damage to vascular structures as guidewire 103 is maneuvered into position.

Figure 5:
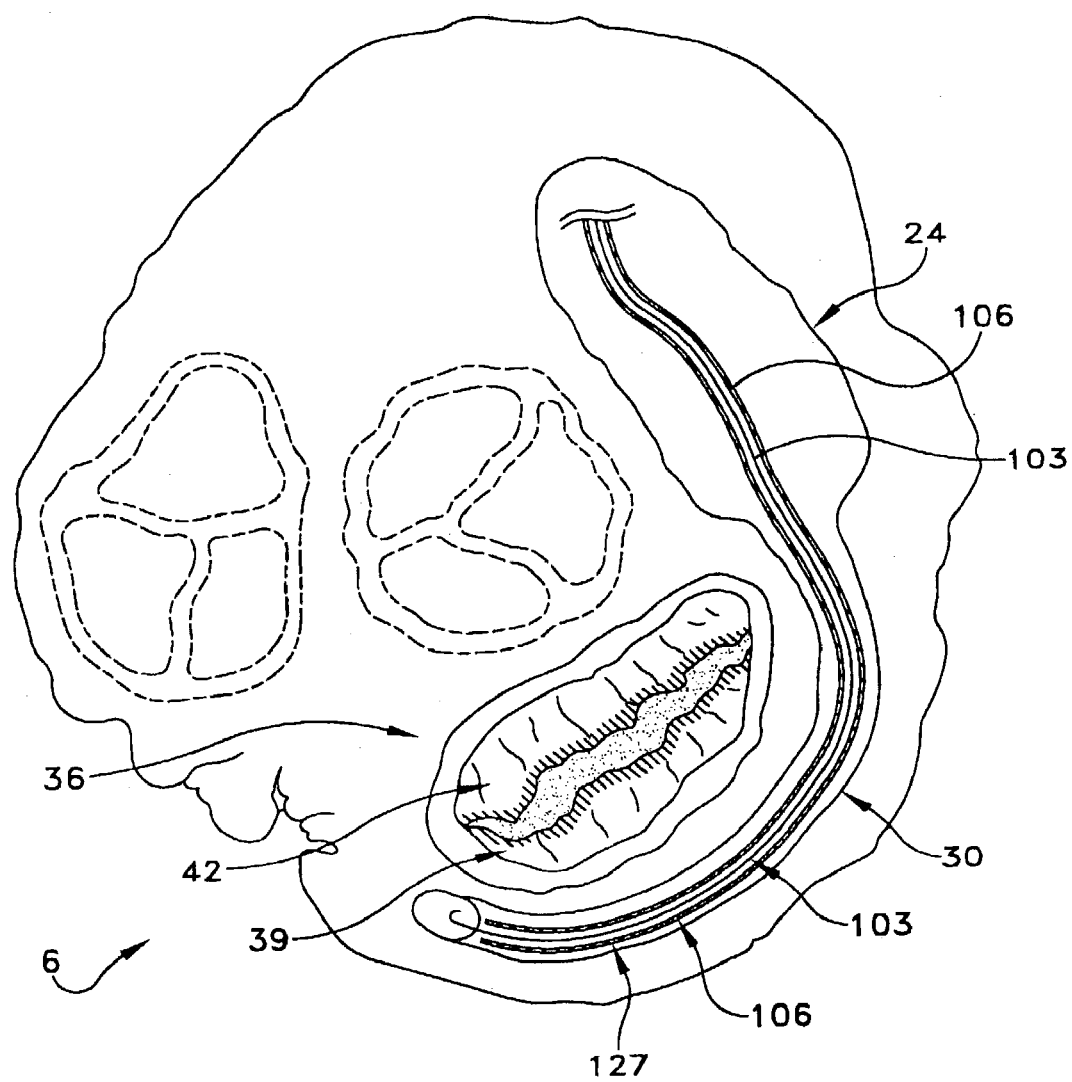

Next, distal end 127 of delivery catheter 106 is placed over proximal end 118 of guidewire 103 and passed down the guidewire until the distal end 127 of the delivery catheter 106 is positioned in coronary sinus 30 (FIG. 5). Again, it will be appreciated that as the flexible delivery catheter 106 passes down the coronary sinus, the delivery catheter will tend to assume the natural curved shape of the coronary sinus, due to the flexible nature of the delivery catheter.

Figure 6:
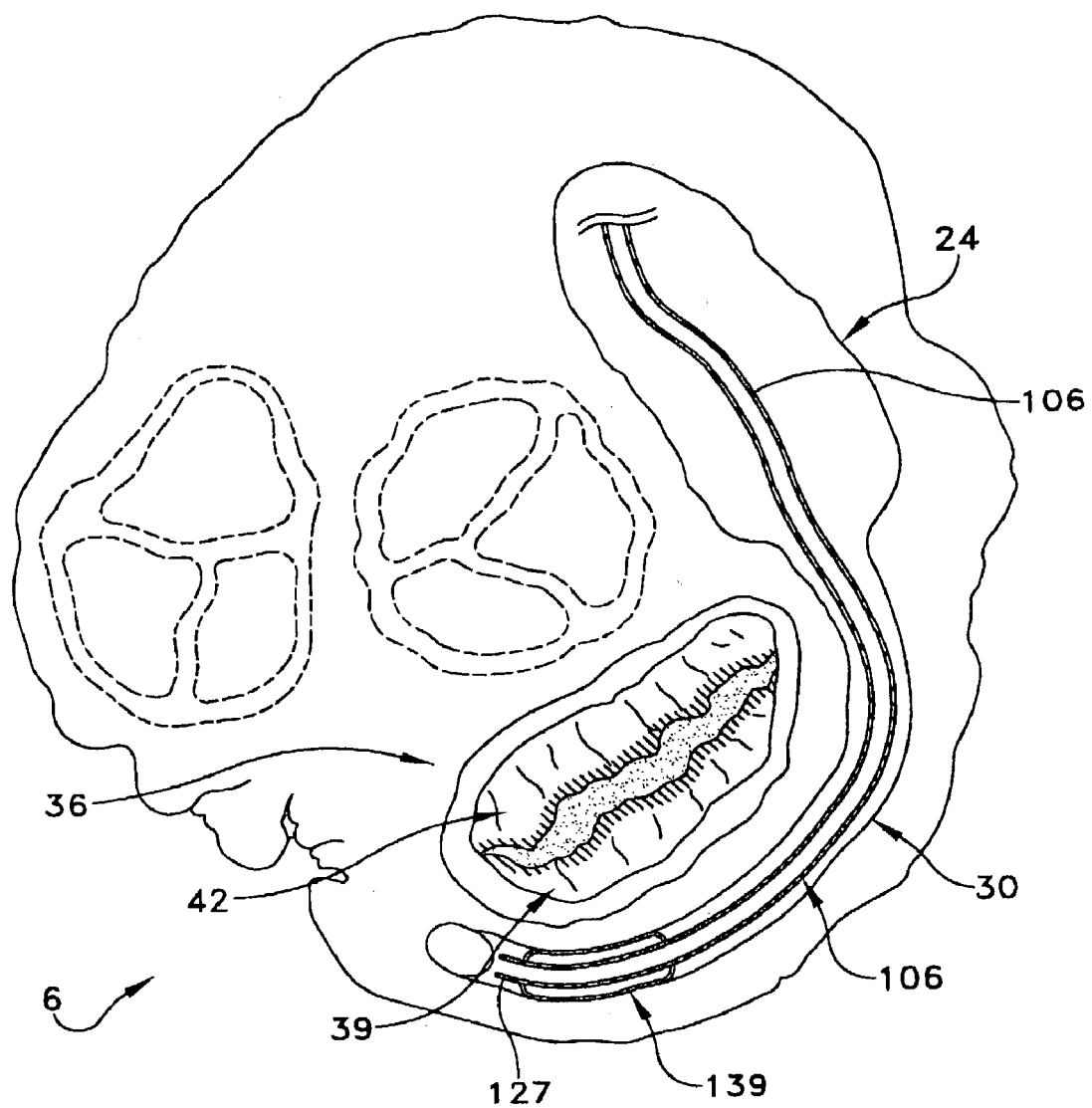

Once delivery catheter 106 has been positioned within the coronary sinus, guidewire 103 is removed (FIG. 6). Either before or after guidewire 103 is removed, balloon 139 may be inflated so as to secure distal end 127 of delivery catheter 106 in position within coronary sinus 30. Alternatively, a selected one of several anchor structures described hereinbelow may be provided and at this point activated so as to secure the catheter distal end 127 in place.

Figure 7:
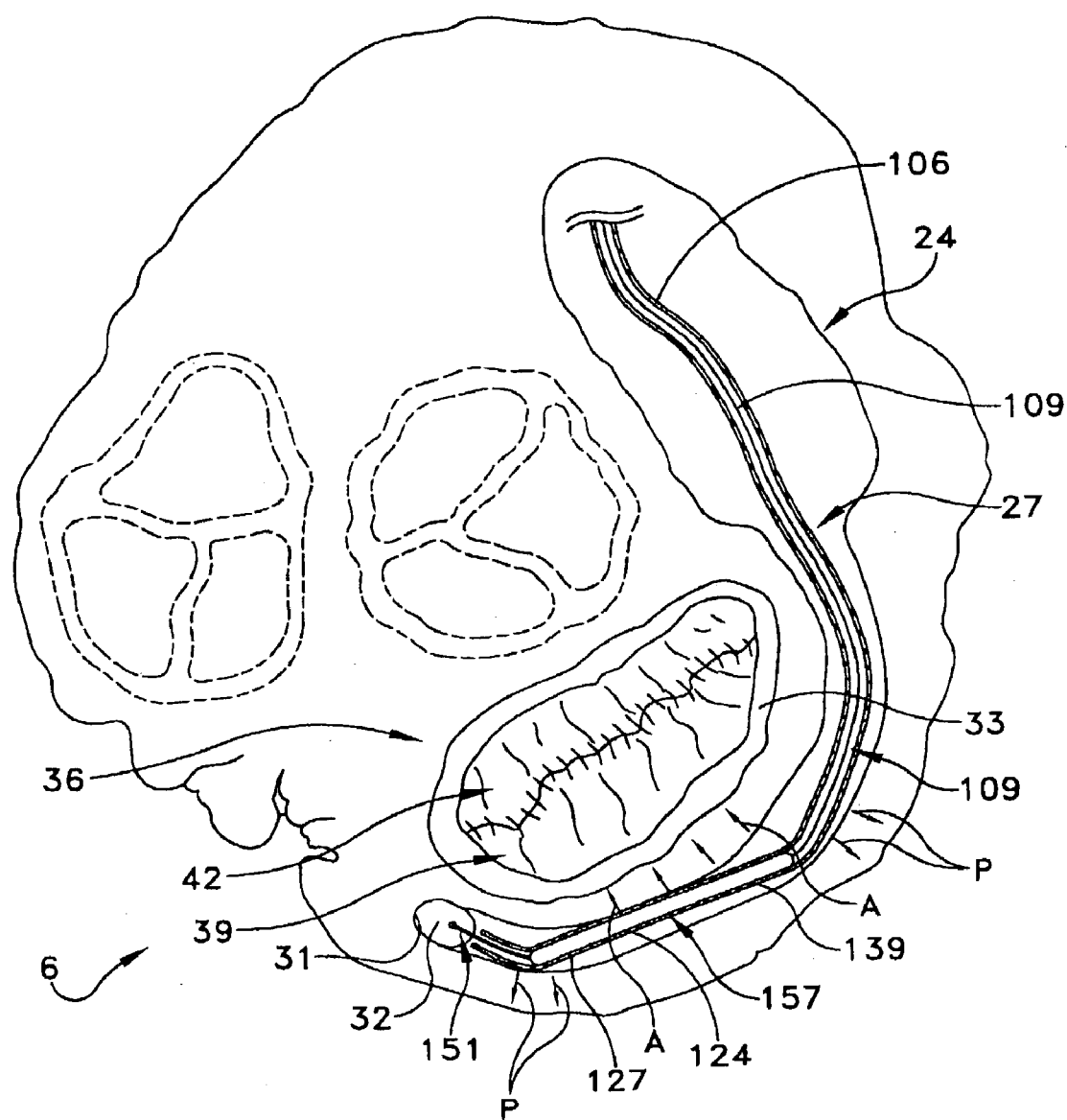

Next, push rod 109 is passed down the central lumen 136 of delivery catheter 106. As the push rod's straight, substantially rigid elongated body 157 is passed down central lumen 136 of delivery catheter 106, it forces the delivery catheter 106 to assume a straight configuration at the point where the straight, substantially rigid elongated body 157 currently resides (FIG. 7). As push rod 109 is pushed down delivery catheter 106, balloon 139 holds the distal end 127 of the delivery catheter 106 in position within coronary sinus 30.

Push rod 109 is pushed down delivery catheter 106, utilizing proximal handle 160 as needed, until the straight, substantially rigid elongated body 157 is located adjacent to the posterior annulus 33 of mitral valve 36 (FIG. 7). As this occurs, the presence of the straight, substantially rigid elongated body 157 in delivery catheter 106 causes at least a portion of coronary sinus 30 to assume a substantially straight configuration at this point, so that the posterior annulus 33 of mitral valve 36 is forced anteriorly. This causes the mitral valve's posterior leaflet 39 to move anteriorly so as to improve mitral valve leaflet coaptation and thereby reduce (or completely eliminate) mitral valve regurgitation. In this respect, it should be appreciated that the posterior annulus 33 may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like. Using standard visualization means (e.g. echocardiography or fluoroscopy), the exact position of the straight, substantially rigid elongated body 157 is adjusted so as to reduce (or completely eliminate) regurgitation in mitral valve 36.

In this respect, it should be appreciated that the straight, substantially rigid elongated body 157 is preferably sized to be somewhat less than the length of the coronary sinus between coronary ostium 27 and AIV 32. However, in some circumstances it may be desirable to size the straight, substantially rigid elongated body 157 so that it will extend out of the coronary sinus 30 and into the right atrium 24.

Furthermore, it should also be appreciated that the system provides a degree of tactile feedback to the user during deployment. More particularly, substantial resistance will typically be encountered as the straight, substantially rigid elongated body 157 is pushed out of right atrium 24 and into coronary sinus 30; then resistance will typically drop as body 157 is moved through the coronary sinus; and then resistance will typically increase significantly again as the distal end 151 of push rod 109, and/or the leading distal tip of body 157, comes to the far end 31 of the coronary sinus. Thus, there is something of a tactile "sweet spot" when the straight, substantially rigid elongated body 157 is located in the coronary sinus between coronary ostium 27 and AIV 32, and this tactile "sweet spot" can be helpful to the user in positioning the straight, substantially rigid elongated body 157 in coronary sinus 30.

At this point in the procedure, the straight, substantially rigid elongated body 157 is locked in position, e.g., by closing adjustable valve 133 (FIG. 3), and balloon 139 may be deflated.

System 100, less guidewire 103, is left in this position until it is no longer needed. In some cases, this may mean that system 100 is left in position for a period of a few hours, days or weeks; in other cases system 100 may be substantially permanent. If and when system 100 is to be removed, push rod 109 is removed from delivery catheter 106, and then delivery catheter 106 is removed from the patient.

Thus, it will be seen that with the present invention, the straight, substantially rigid elongated body 157 is essentially force-fit into the normally curved portion of the coronary sinus adjacent to the mitral valve's posterior leaflet 39. By properly sizing the length of the straight, substantially rigid elongated body 157 relative to the natural curvature of the patient's anatomy, and by properly positioning the straight, substantially rigid elongated body 157 in the patient's coronary sinus, the straight, substantially rigid elongated body will cause at least a portion of the coronary sinus to assume a substantially straight configuration adjacent to the posterior leaflet 39 of the mitral valve 36. This action will, in turn, drive the posterior annulus of the mitral valve anteriorly, so as to improve leaflet coaptation and thereby reduce mitral regurgitation. Thus, by inserting the straight, substantially rigid elongated body 157 into the coronary sinus 30 adjacent to the posterior leaflet 39 of the mitral valve 36, the annulus 33 of the mitral valve is effectively manipulated so that it will assume an increased radius of curvature.

As noted above, by properly sizing the length of the straight, substantially rigid elongated body 157 relative to the natural curvature of the patient's anatomy, and by properly positioning the straight, substantially rigid elongated body 157 in the patient's coronary sinus, the straight, substantially rigid elongated body will cause at least a portion of the coronary sinus to assume a substantially straight configuration adjacent to the posterior leaflet 39 of the mitral valve 36, whereby to drive the posterior annulus of the mitral valve anteriorly, so as to improve leaflet coaptation and thereby reduce mitral regurgitation. To this end, push rod 109 is preferably provided as part of a kit having a plurality of different push rods 109, each with a differently-sized elongated body 157, whereby a physician may select and deploy the appropriately-sized elongated body 157 for a specific patient's anatomy. Furthermore, if upon deployment it should be discovered (e.g., under echocardiography or fluoroscopy) that a different size of elongated body 157 is needed, the first push rod 109 may be replaced by a second push rod having the desired size of elongated body 157.

It has also been found that by inserting the straight, substantially rigid elongated body 157 into the coronary sinus adjacent to the posterior leaflet of the mitral valve, the left ventricle may be remodeled so as to help alleviate congestive heart failure.

It is significant to note that with the present invention, the distal and proximal ends of straight, substantially rigid elongated body 157 apply a posteriorly-directed force on the walls of coronary sinus 30 (e.g., as shown with arrows P in FIG. 7) while the intermediate portion of straight, substantially rigid elongated body 157 applies an anteriorly-directed force on the walls of coronary sinus 30 (e.g., as shown with arrows A in FIG. 7).

Figure 8:
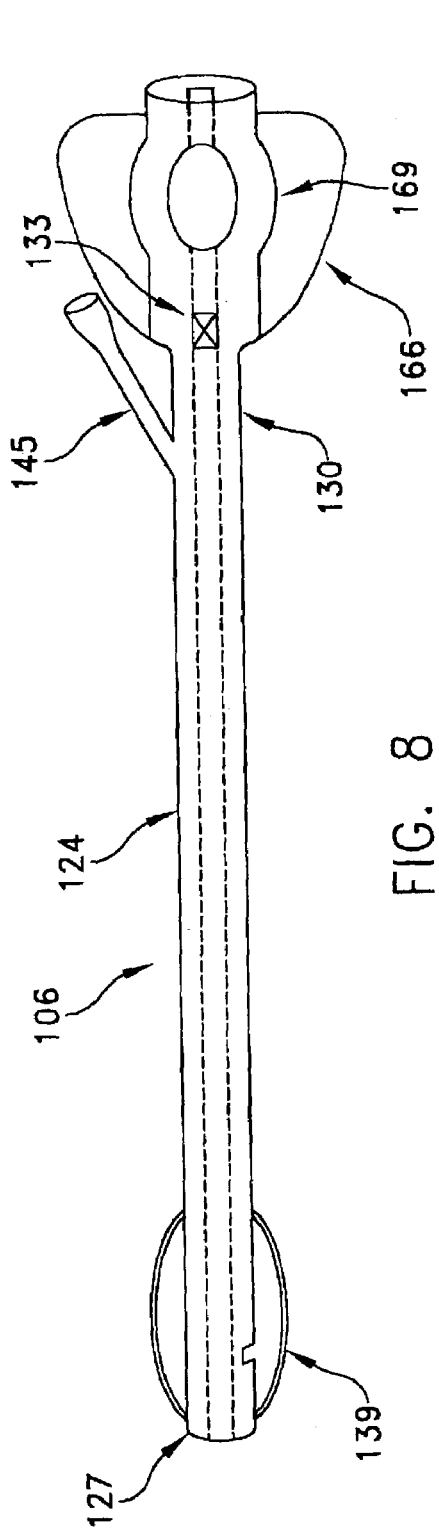
FIG. 8 shows an alternative form of delivery catheter.

In some cases, the proximal end 130 of delivery catheter 106 may be fixed to the patient's outer skin, using standard patient care methods such as adhesive tape, pursestring sutures, skin staples, etc. In other cases, proximal end 130 of delivery catheter 106 may include a sewing cuff whereby the delivery catheter may be secured to the patient's tissue by suturing. See, for example, FIG. 8, where a sewing cuff 166 is shown attached to the proximal end 130 of delivery catheter 106. If desired, an element 169 may be provided proximal to adjustable valve 133, whereby flexible push rod 109 may be made fast to delivery catheter 106. By way of example, element 169 may comprise a crimpable element to secure flexible push rod 109 to delivery catheter 106, which is in turn secured to the patient, e.g., with sewing cuff 166.

If desired, the proximal end of the assembly may be embedded under the skin of the patient, e.g., in the case of a permanent implant.

As noted above, it can be helpful to anchor the distal end of delivery catheter 106 in position within the coronary sinus prior to pushing push rod 109 into the delivery catheter. Such an arrangement will keep the delivery catheter in place as the push rod makes the turn within the right atrium and enters the coronary sinus. In the absence of such anchoring, the push rod may drive the delivery catheter down the inferior vena cava 21 (FIG. 1). By securing the distal end of delivery catheter 106 to the walls of coronary sinus 30, the delivery catheter can be stabilized against diversion down the inferior vena cava 21 when the straight, substantially rigid elongate body 157 encounters initial resistance to making the turn into the coronary sinus.

Figure 9:
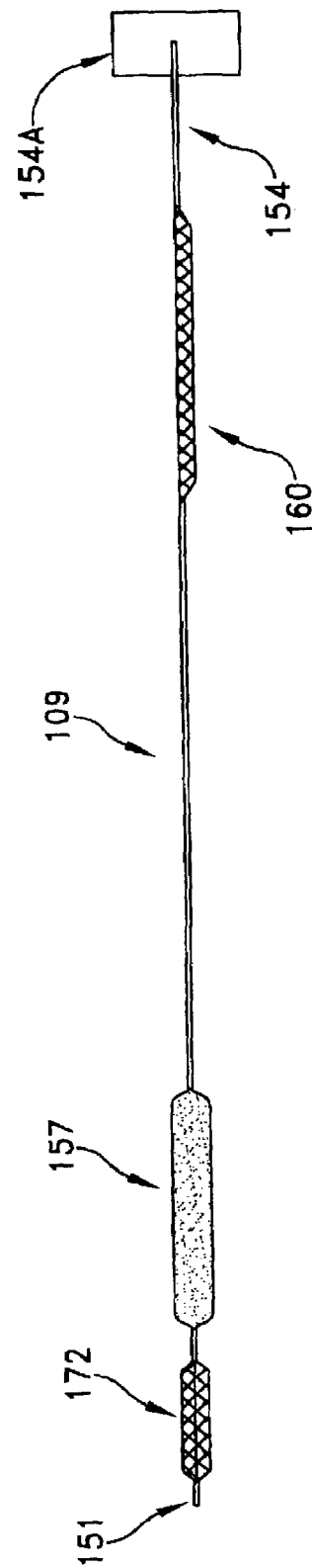
FIG. 9 shows an alternative form of flexible push rod.

The balloon 139 is one way of accomplishing such anchoring. However, it is also possible to utilize other types of securing mechanisms to anchor the distal end 127 of delivery catheter 106 in position within coronary sinus 30, e.g., spring clips, ribs, etc. If desired, the distal end 151 of push rod 109 may itself be provided with a distal anchor, e.g., such as the distal anchor 172 shown in FIG. 9. Such a distal anchor on push rod 109 can help hold the straight, substantially rigid elongated body 157 in proper position within coronary sinus 30.

Figure 9A:
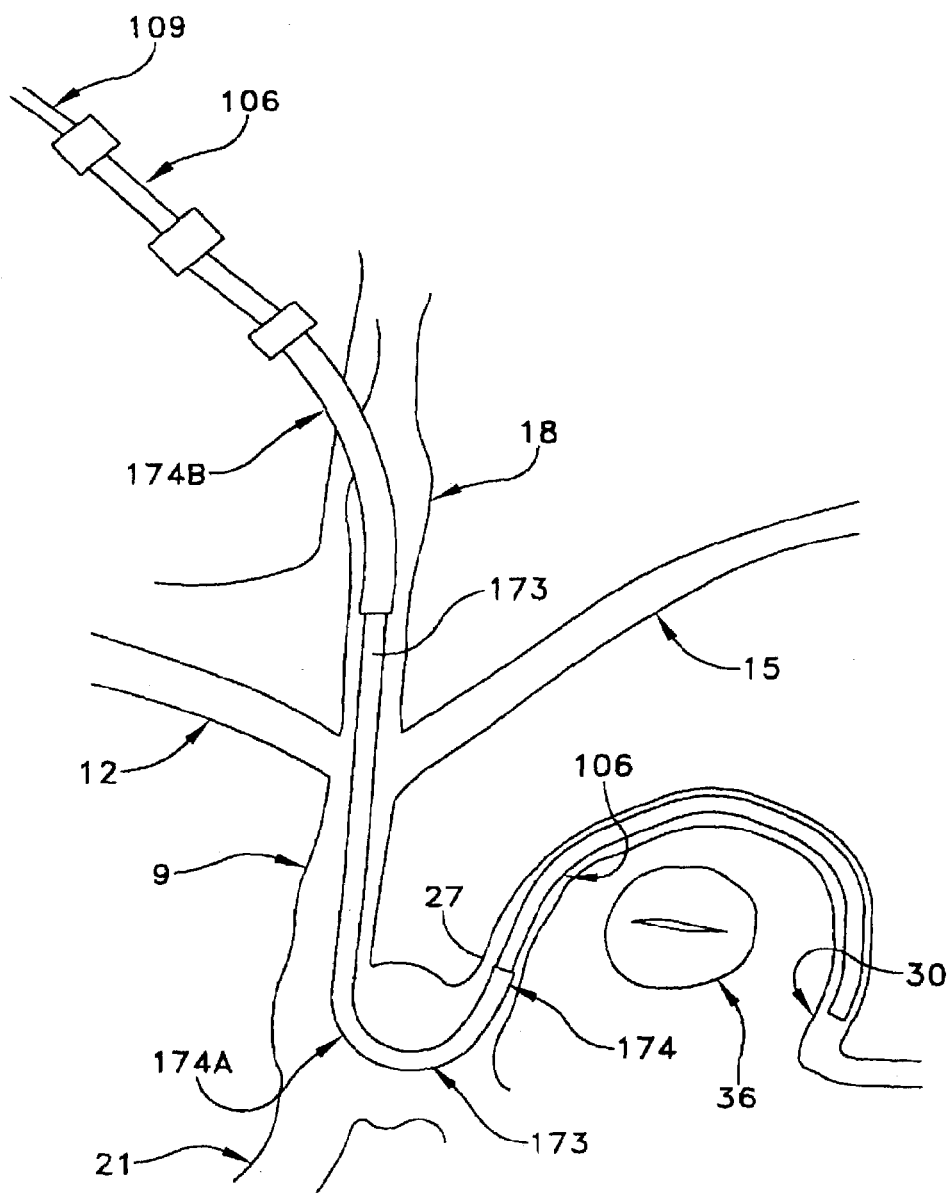
FIG. 9A shows an alternative form of the present invention.

It is also possible to prevent diversion of delivery catheter 106 down inferior vena cava 21 without anchoring the distal end of delivery catheter 106 to the walls of the coronary sinus. More particularly, and looking now at FIG. 9A, there is shown a support catheter 173 which is formed out of a more rigid material than delivery catheter 106. Support catheter 173 is constructed so that its distal end 174 can be positioned in coronary ostium 27 and then its sidewall 174A can support delivery catheter 106 adjacent to inferior vena cava 21 when push rod 109 is passed down delivery catheter 106, whereby to prevent delivery catheter 106 from diverting down inferior vena cava 21. FIG. 9A also shows an introducer catheter 174B at the entrance to jugular vein 18.

Looking next at FIG. 9B, there is shown a push rod 112A which comprises an alternative form of push rod. Push rod 112A comprises a flexible body 148A having a distal end 151A and a proximal end 154A. Preferably, flexible body 148A is formed out of a superelastic shape memory alloy, such as Nitinol. A straight, substantially rigid member 157A is formed on flexible body 148A, proximal to distal end 151A. Substantially rigid member 157A can have a variety of different lengths so as to accommodate different patient anatomies. A tube 158A is positioned concentrically over flexible body 148A and extends for at least part of the distance between substantially rigid member 157A and a locking collar 159A secured to proximal end 154A of flexible body 148A. Tube 158A serves as a stiffener or reinforcer for flexible body 148A, whereby flexible body 148A can have the flexibility required (particularly at its distal end 151A) to traverse tortuous vascular passages, yet have the column strength, particularly at its proximal end 154A, to advance flexible body 148A by pushing. In addition, tube 158A can be sized so as to have a diameter just slightly smaller than the internal diameter of delivery catheter 106, whereby to further support flexible body 148A. In one preferred form of the invention, tube 158A preferably comprises a PEEK tube.

Looking next at FIG. 9C, flexible body 148A can also be necked down, e.g., as shown at 220A, so as to further increase the flexibility of flexible body 148A distal to tube 158A.

Flexible push rod 112A preferably is a device with a series of changes in stiffness and flexibility that allow the device to be bending flexible and have column strength sufficient to pass through a tortuous path, such as the vascular system of a patient, yet have specific areas of stiffness to reduce mitral valve regurgitation by pushing the posterior annulus anteriorly and thus closing the gap between the anterior and posterior leaflets of the mitral valve. One preferred embodiment of this device is a single rod of superelastic material, such as Nitinol, that has a plurality of changes in diameter that allow for appropriate bending flexibility. At the same time, the largest diameter section has a bending stiffness sufficient to push the posterior annulus anteriorly. The longest portions of the rod may have serrations that provide bending flexibility along with column strength.

Figure 9D:
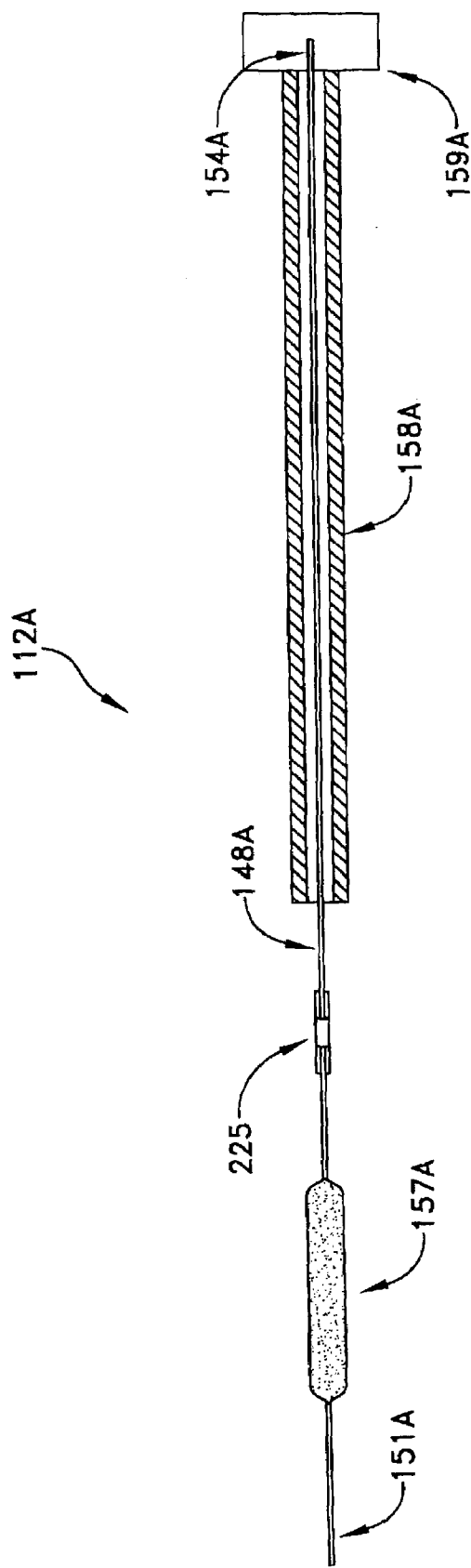

Alternatively, and looking next at FIG. 9D, it is also possible to provide additional flexibility to flexible body 148A by severing the flexible body along its length and then connecting the two severed portions with a flexible tube or wire, e.g., such as is shown at 225.

In addition to the foregoing, in an alternative embodiment as shown in FIG. 9E, it is also possible to use a support catheter 162, preferably with a pre-formed tip 164, which could be advanced over guidewire 103, whereby pre-formed tip 164 of support catheter 162 would engage the opening of the coronary sinus 30. The distalmost portion of the pre-formed tip 164 is sufficiently flexible to execute extreme bends, and may be of reduced diameter, so as to facilitate deployment into the coronary sinus. At the same time, the region proximal to the distalmost portion is preferably substantially more rigid, e.g., with a rigidity similar to the sidewall 174A of support catheter 173, so as to prevent diversion down inferior vena cava 21. Upon successful engagement and advancement of the support catheter tip 164 a short distance into the coronary sinus, guidewire 103 is removed. Then delivery catheter 106 is advanced toward and into the coronary sinus through the central lumen 165 of support catheter 162. Then, push rod 109 would be advanced within central lumen 136 of the delivery catheter 106 into the coronary sinus and into position as described herein.

It is also envisioned that the structure of the delivery catheter 106 may be modified so as to add a region 163 (FIG. 9F) of increased stiffness proximal to the distal tip 127 of delivery catheter 106. In this way the distal tip of delivery catheter 106 will be sufficiently flexible for placement into the coronary sinus, yet the body of delivery catheter will be rigid enough to prevent diversion down the inferior vena cava during the delivery of push rod 109. Where delivery catheter 106 includes an intermediate region of increased stiffness, it should not be necessary to utilize a support catheter 173 or a support catheter 162 to prevent diversion down the inferior vena cava.

As noted above, as push rod 109 (or 112A) is advanced to the region adjacent to the posterior annulus of the mitral valve, the straight, substantially rigid elongated body 157 (or 157A) distorts the natural configuration of the coronary sinus so that it assumes a substantially straight configuration. While this action induces the desired valve remodeling, it can also induce a significant stress on the walls of the coronary sinus, particularly at the distal and proximal ends of the straight, substantially rigid elongated body 157 (or 157A), where stress will be concentrated. To this end, the construction of the straight, substantially rigid elongated body 157 (or 157A) may be modified somewhat so as to better distribute this stress.

More particularly, and looking next at FIG. 10, the distal and proximal ends of straight, substantially rigid elongated body 157 may include relatively flexible portions 175 to help better distribute the stress exerted on the walls of the coronary sinus. Additionally, and/or alternatively, any taper applied to the distal and proximal ends of straight, substantially rigid elongated body 157 may be elongated, e.g., such as shown at 178 in FIG. 11, so as to better distribute the stress imposed on the walls of the coronary sinus.

In the preceding discussion of system 100, push rod 109 is described as being inserted to the surgical site through the delivery catheter 106 and remaining within delivery catheter 106 while at the surgical site and, when push rod 109 is to be removed, removing push rod 109 and then delivery catheter 106. However, if desired, once push rod 109 has been deployed at the surgical site, delivery catheter 106 may then be removed, leaving just push rod 109 at the surgical site. See, for example, FIG. 11A.

It is also possible to advance push rod 109 directly to the surgical site without passing it through a delivery catheter; in this case push rod 109 would be advanced on its own through the intervening vascular structure until it is deployed in coronary sinus 30.

Referring to FIG. 11B, it will be seen that the body 157 may be provided with extended strain relief tapers 200 and a non-traumatic distal tip 202 in a body having a cross-section of a circular configuration (FIG. 11C), which provides the advantage of rotational symmetry.

In FIGS. 11D and 11E, there is shown a similar body 157 with extended strain relief tapers 200 and non-traumatic tip 202, but of a generally "square" configuration with rounded corners, in cross-section, which provides four stable orientations.

In FIGS. 11F and 11G, there is shown a similar body 157 which is generally rectangular in cross-section. The rectangular configuration offers increased flexibility in two stable orientations.

As illustrated in FIGS. 11H, 11I, 11J and 11K, the body 157, whether circular (FIGS. 11H and 11I) or generally rectangular (FIGS. 11J and 11K), may be hollow and of a metal construction. Tubular hollow cross-sections can provide additional flexure.

Figure 11A:
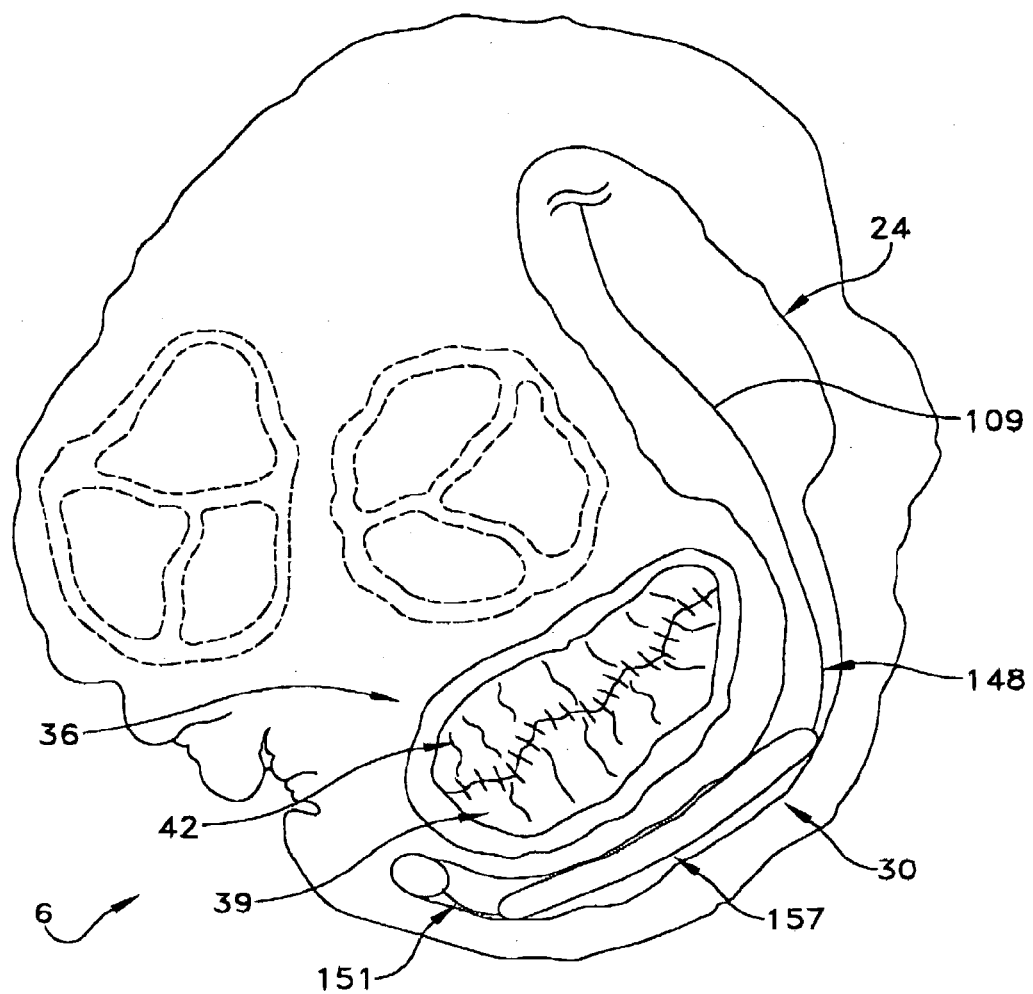
Figure 11I:
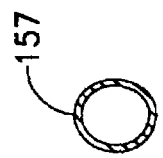
Figure 11H:
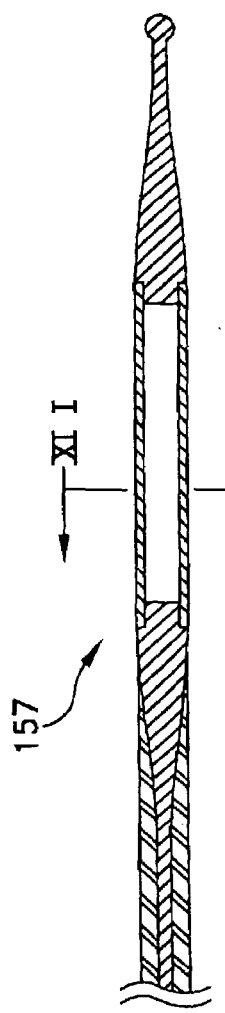
Figure 11K:
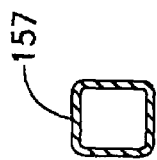
Figure 11J:
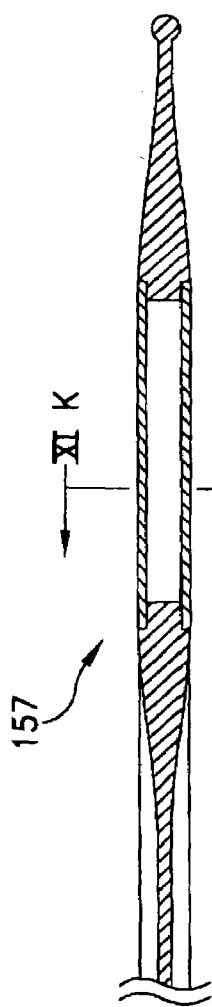
Figure 11L:
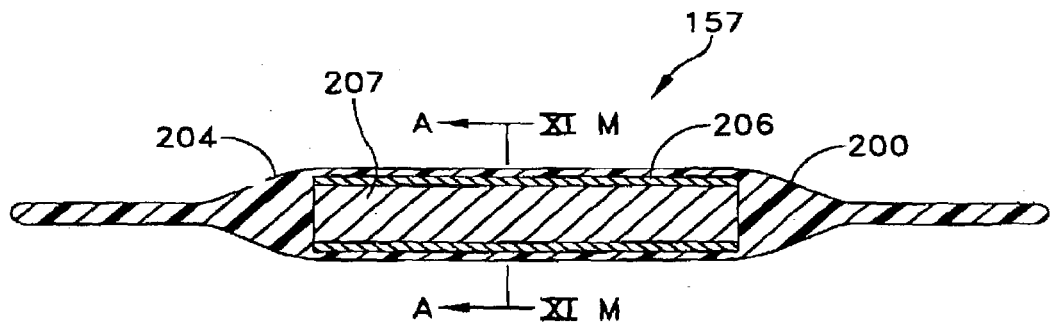
Figure 11M:
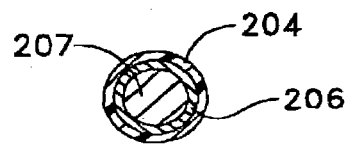
Figure 11N:
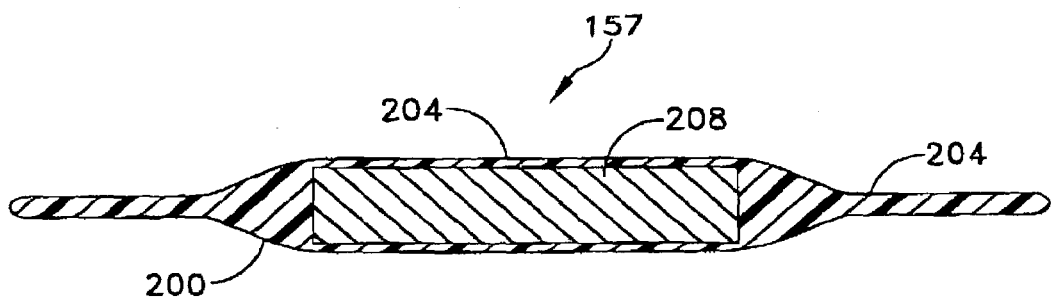
Figure 11P:
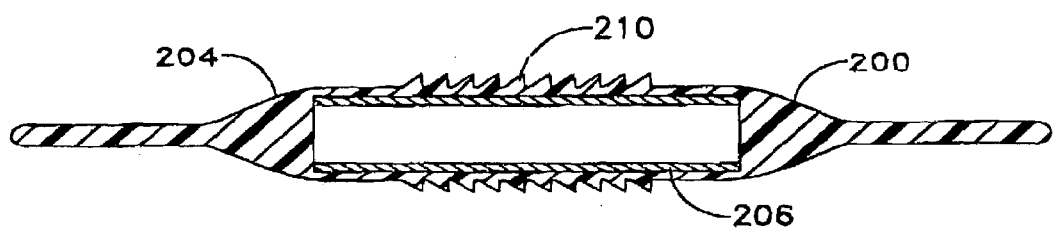

In FIGS. 11L-11N and 11P, there are shown embodiments in which an elastomeric outer body 204 is molded over a metal tube 206 (FIGS. 11L and 11P) or over a metal rod 208 (FIG. 11N). The tubes 206 may be empty (FIG. 11P) or filled with an appropriate metal or other material 207 (FIG. 11L).

All of the embodiments of FIGS. 11L-11N and 11P may be molded with barbs 210 (shown in FIG. 11P) which are engageable with the interior of the delivery catheter 106 and/or the walls of the coronary sinus 30 so as to help stabilize the longitudinal position of body 157.

In FIGS. 11R and 11S, there are illustrated stepped strain relief segments 212, and in FIG. 11Q there is shown an embodiment in which there are provided a series of metal and/or plastic strain relief segments 213.

During introduction, the body 157 must negotiate two difficult turns and several less tortuous ones. The two difficult ones are (1) a small radius 80 to 120 degree turn as the device begins to enter the coronary ostium, and (2) the 160 to 200 degree turn around the coronary sinus. Two problems must be overcome in order to successfully place the body 157 in the coronary sinus. First, there is a tendency for the delivery catheter 106 to withdraw from the coronary sinus as the body 157 is advancing into the coronary sinus. Second, once the body 157 has entered the coronary sinus, the forces required to advance it into its correct position can cause the delivery catheter 106 to prolapse down the inferior vena cava (in the case of a jugular or subclavian approach) or up into the right atrium or superior vena cava (in the case of a femoral vein approach). Once the delivery catheter has prolapsed, further advancement of the body 157 is generally very difficult. Several features of the body 157 and introducer systems disclosed above and hereinbelow may be incorporated to solve these introduction problems.

The difficulties associated with introduction of the body 157 illustrate the benefit of an articulating (i.e. active) body over a non-articulating (passive) body. An articulating body requires significantly smaller forces during introduction, mitigating the anchoring features required to eliminate catheter withdrawal and prolapse. The liability of the articulating (i.e., active body), however, is that it requires a more complex mechanism.

The body 157 must be able to resist bending moments in order to appropriately deform the mitral annulus. Note that, for the body described above, this requirement directly conflicts with the ability to negotiate the sharp turn into the coronary ostium. For a non-articulating (i.e., passive) body, a balance must generally be struck between flexibility (for introduction) and stiffness (for in-situ functionality).

Figure 11T:
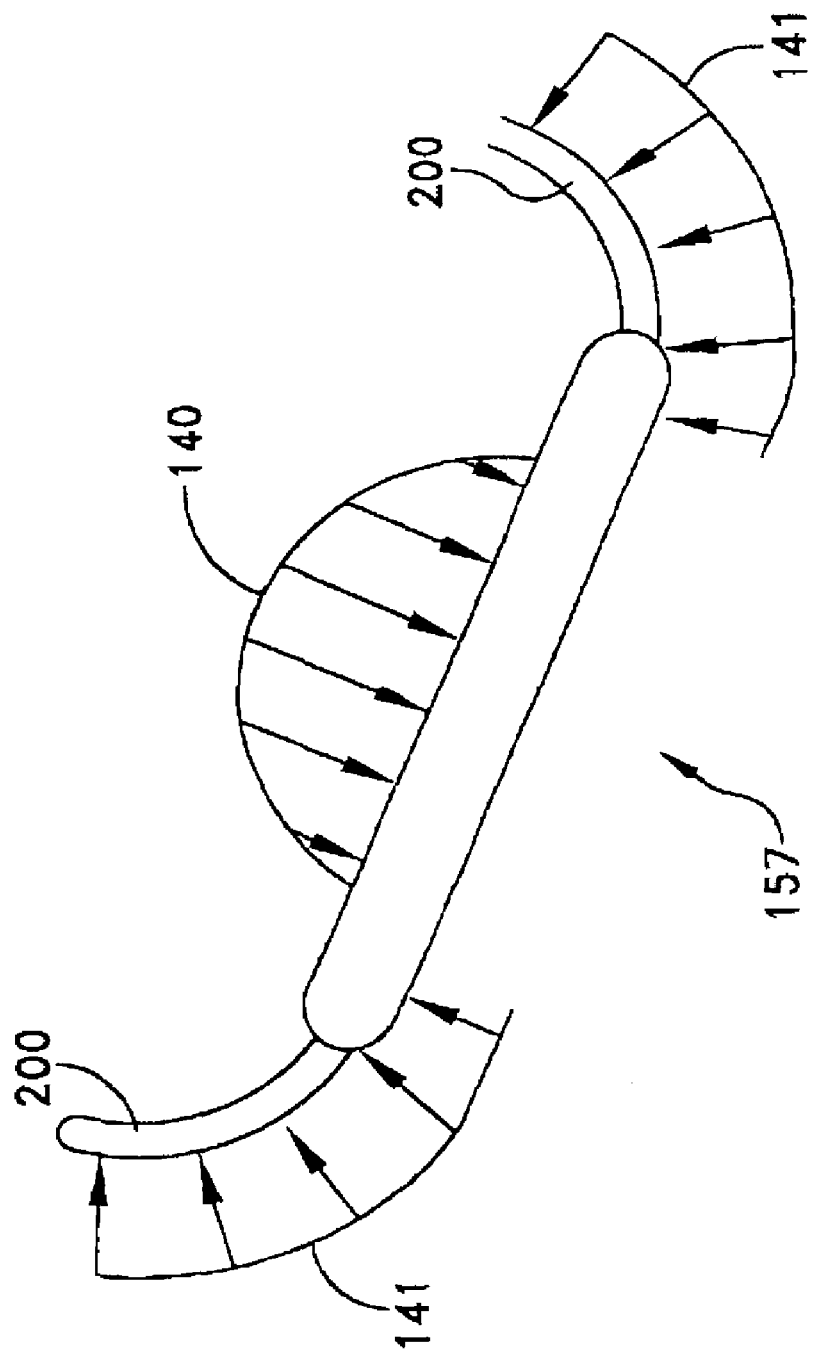
FIG. 11T is a diagrammatic illustration of forces engaging upon an operative portion of the inventive assemblies.

The force loading and strain reliefs for the body 157 are shown in FIG. 11T. A high, distributed center load 140 is imparted by the mitral annulus and smaller (approximately half) loads 141 on either strain relief 200 are imparted by the coronary sinus.

Figure 11U:
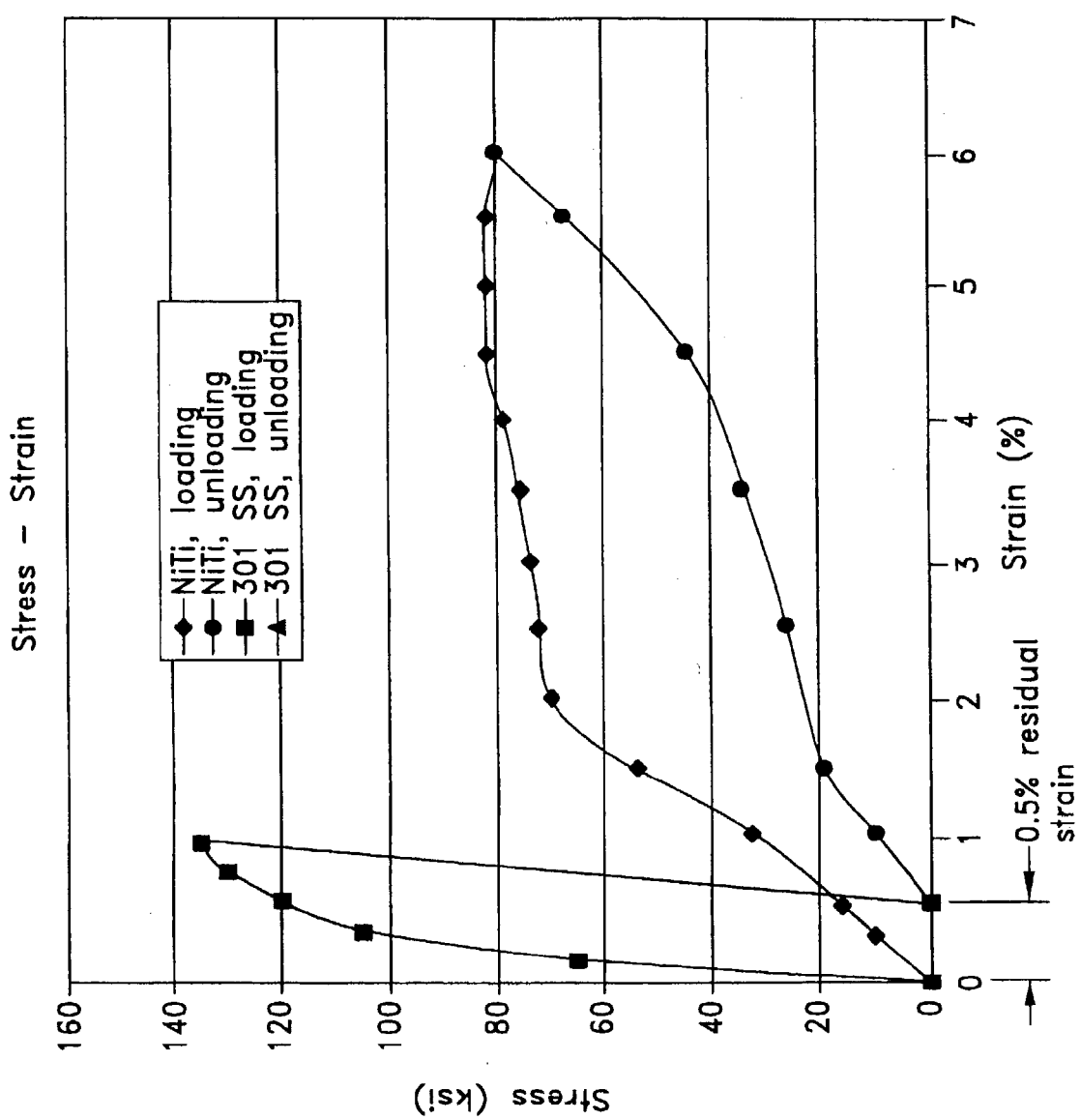
FIGS. 11U and 11V are graphs illustrating comparative strains and stresses.

The stress-strain curves for stainless steel and nickel titanium are shown in FIG. 11U. Stress is defined as force per unit area, and strain is defined as elongation per unit length. For simplicity, a pure tensile case will be described first. The slightly more complicated condition of bending will be described next.

In pure tension, the stress is uniformly distributed across the area of the body. As a result, the force-deflection and stress-strain curves are similar to each other, as seen in FIG. 11V.

In bending, the stress distribution in not uniform throughout the body, but is distributed. The outer fibers of the body 157 are at higher strain levels than those close to the neutral axis. This outer fiber strain limits the amount of bend that the body can tolerate. Sharper bends mean higher strains.

After a body 157 has been loaded beyond its proportional limit, it will retain some residual strain when it is unloaded. This residual strain will manifest itself as a permanent elongation in the case of a tensile strain, or as a residual bend in the case of a bending strain. A residual bend in the body will have a very specific detrimental effect on the performance of the body. Due to the lubricity of the vessels, a round body with a residual bend will self-align to the minimum energy condition where the bend of the body coincides with the bend of the coronary sinus. As a result, the amount of bend in the body directly subtracts from the deflection of the mitral annulus. Larger residual strains will result in larger residual bends, and larger "lost" deflection.

Figure 11V:
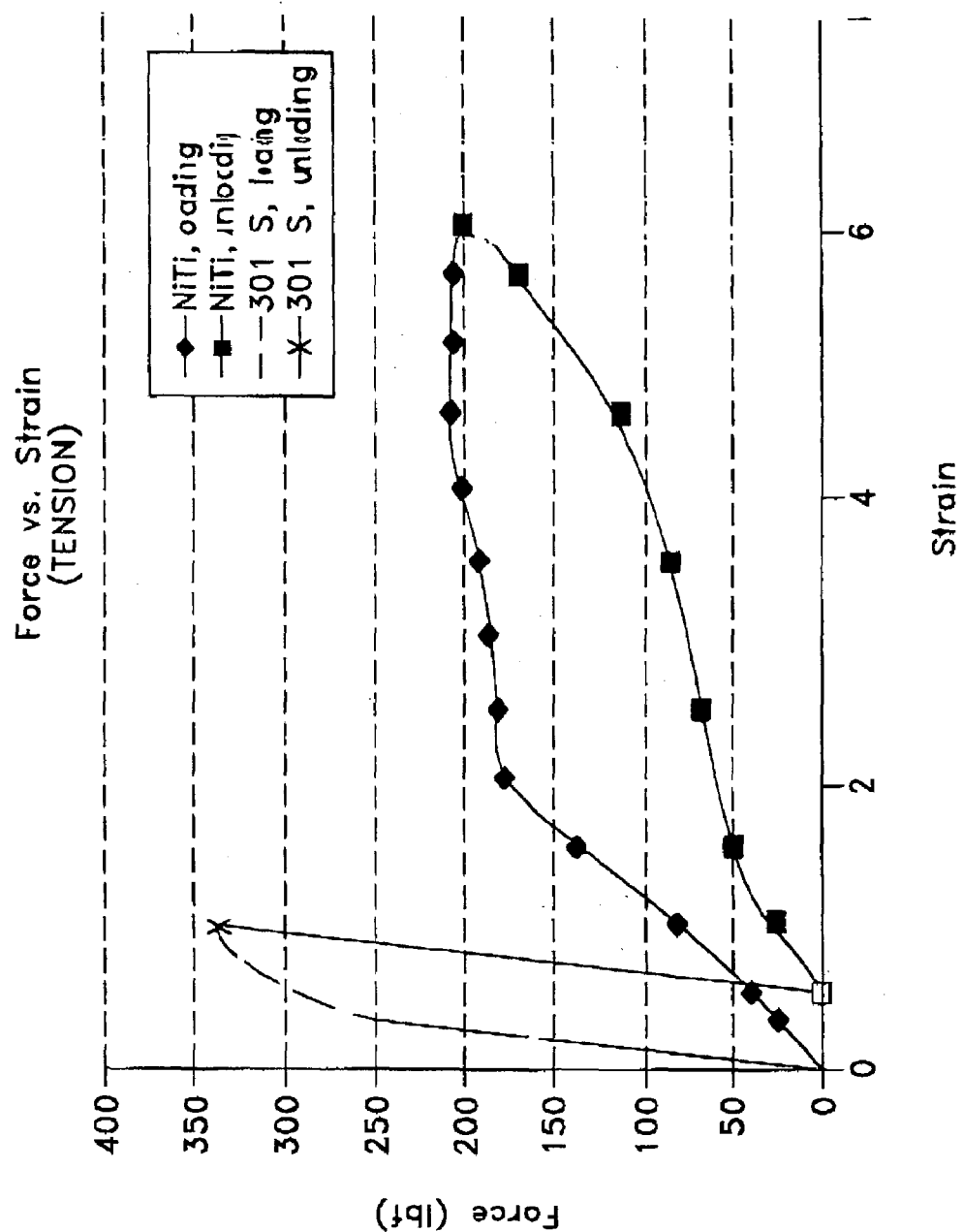

In can be seen in FIG. 11V that stainless steel can be stretched to approximately 1% and return with a residual strain of 0.5%, while nickel titanium can be stretched to approximately 6% and return with the same residual strain. This means that nickel titanium can bend around much sharper bends, and return with an equivalent residual strain.

In the inventive method, the body 157 preferably is placed with a percutaneous procedure. When introducing the body, it must negotiate some relatively sharp turns on its way to the coronary sinus. A body fabricated from non-superelastic material (such as stainless steel) will retain the residual curvature imparted upon the body by the flexure required to negotiate the sharp curves. This residual curvature will detrimentally affect the performance of the body, subtracting from the resultant deflection of the mitral annulus. The use of a body fabricated from a superelastic material will negotiate these sharp curves without acquiring this detrimental residual curvature.

As shown in the stress-strain curves presented in FIG. 11V, the stress in the stainless steel continues to rise between 0 and 1% (although at a slower rate above 0.4%). With the nickel titanium, however, the stress reaches a plateau level at a strain of about 2%. Between 2% and 6% strain, the stress remains almost constant at about 80 ksi.

Since stress correlates to bending forces in the body, it can be seen that the stress plateau has the very desirable effect of putting an upper limit on the forces that are required to bend the device and strain reliefs. The plateau feature of the nickel titanium allows placing an upper limit on the amount of stress put on the tissue that is causing the body or strain reliefs to bend. With careful design, this intrinsic feature of nickel titanium results in two specific benefits:

(1) During insertion of the body 157, the body exerts high side loads on the tissues adjacent to the body. These tissues are deflected out of the way of the body, and the body itself bends in response to these side loads. The most severe side load is placed on the tissue immediately superior to the coronary ostium in the right atrium. The plateau in the stress-strain also allows the selection of an upper limit to the forces exerted on the heart tissue as the device negotiates this curve. Once the maximum side load has been reached (corresponding to the plateau stress), it will require little extra side load to cause the body to bend into a much sharper curve.

(2) In a similar fashion to the situation described above, the plateau in the stress-strain curve allows the selection of an upper limit on the forces (i.e., stresses) that will be exerted on the coronary sinus by the strain reliefs.

Accordingly, it is preferable that the straight, substantially rigid, elongated body 157 be of nickel titanium, or an alloy thereof. In bodies 157 featuring a combination of elastomeric material and metal (e.g., such as those shown in FIGS. 11L-11N and 11P), a preferred metal is, similarly, nickel titanium or an alloy thereof.

Figure 12:
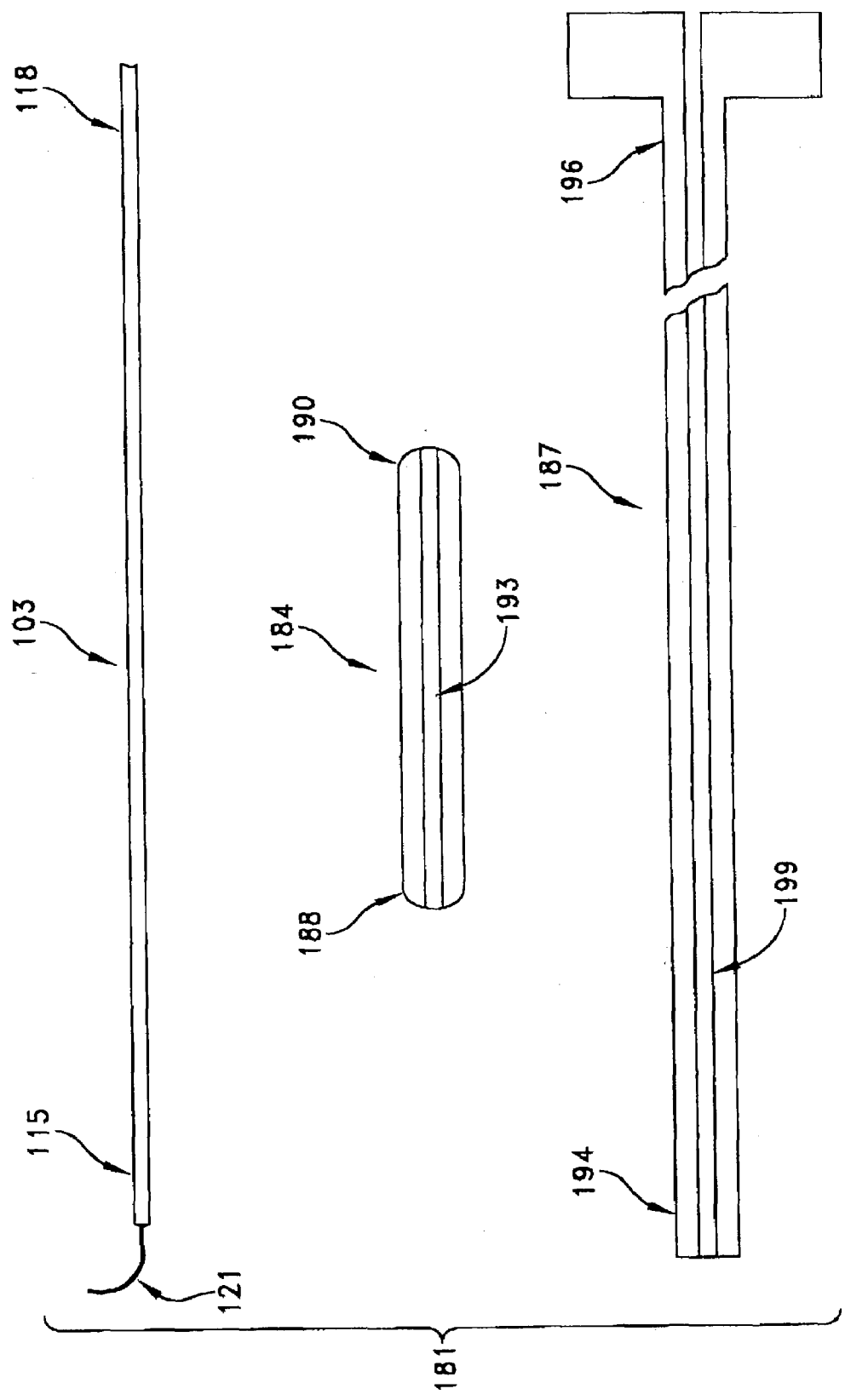
FIG. 12 shows another alternative system formed in accordance with the present invention.

Looking next at FIG. 12, there is shown a system 181 which comprises another preferred embodiment of the present invention. More particularly, system 181 generally comprises the guidewire 103, a straight, substantially rigid elongated body 184 and a push cannula 187.

Guidewire 103 is as previously described.

Straight, substantially rigid elongated body 184, which may have a variety of different lengths, comprises a distal end 188 and a proximal end 190. A central lumen 193 extends between distal end 188 and proximal end 190. Central lumen 193 accommodates guidewire 103.

Push cannula 187 comprises a distal end 194 and a proximal end 196. A central lumen 199 extends between distal end 194 and proximal end 196. Central lumen 199 accommodates guidewire 103.

Figure 13:
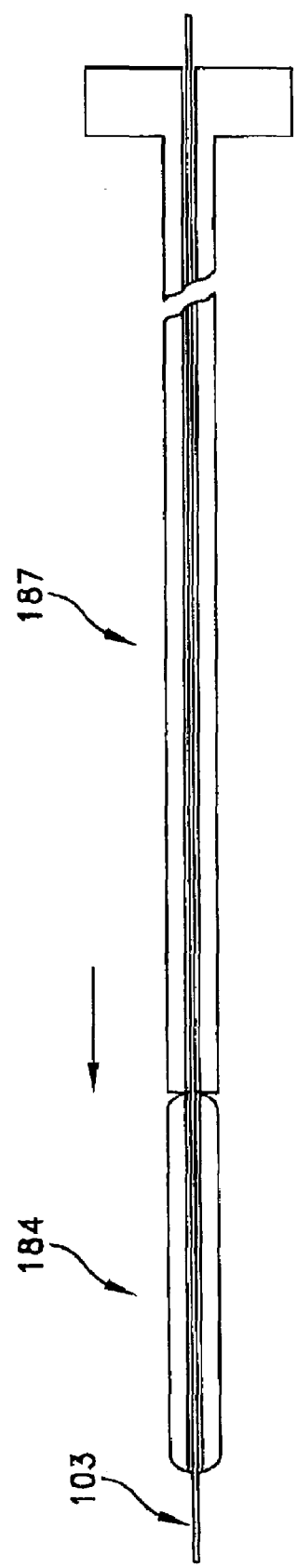
FIG. 13 shows the components of FIG. 12 assembled for use.

As a result of this construction, elongated body 184 and push cannula 187 may be mounted on guidewire 103, and push cannula 187 may be used to push elongated body 184 down guidewire 103 (FIG. 13).

System 181 may be used as follows to reduce mitral regurgitation.

Figure 14:
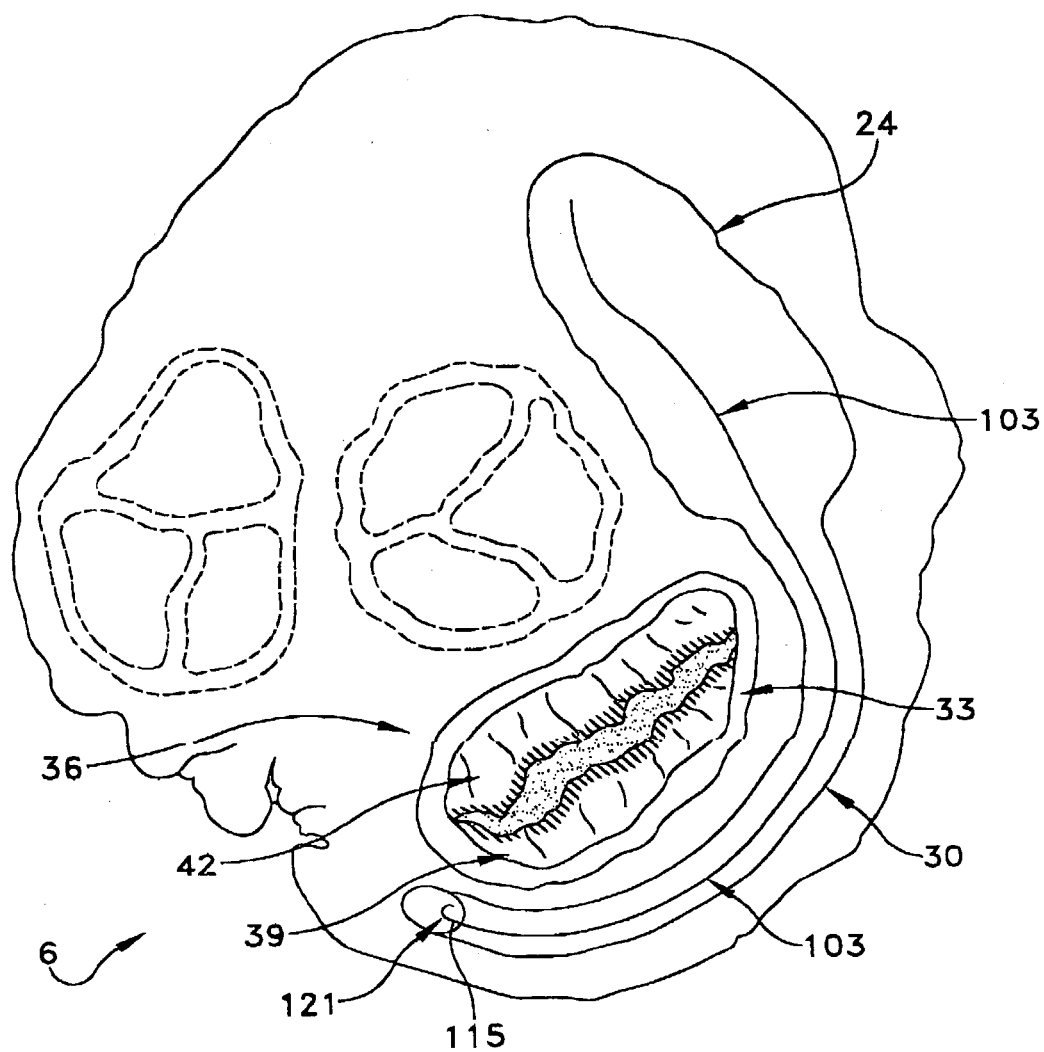
FIGS. 14–16 illustrate another aspect of the present invention.

First, distal end 115 of guidewire 103 is passed down jugular vein 18 (or the left subclavian vein 15) of a patient, down superior vena cava 9, through right atrium 24 of the heart, and into coronary sinus 30 (FIG. 14). It will be appreciated that as flexible guidewire 103 is passed down coronary sinus 30, the guidewire tends to assume the natural curved shape of the coronary sinus, due to the flexible nature of the guidewire. The guidewire's atraumatic spring tip 121 helps minimize damage to vascular structures as the guidewire is advanced into position.

Figure 15:
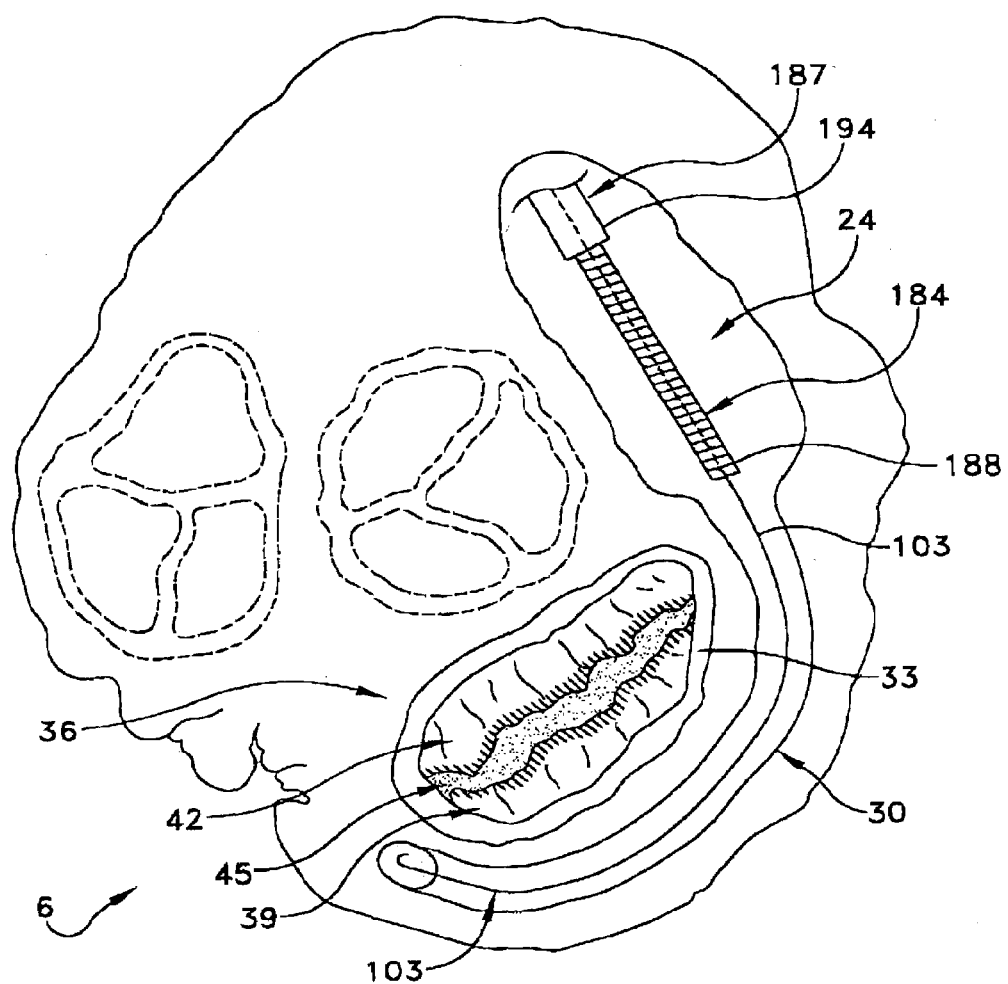

Next, distal end 188 of straight, substantially rigid elongated body 184 is placed over proximal end 118 of guidewire 103 and passed a short distance down the guidewire. Then the distal end 194 of push cannula 187 is placed over proximal end 118 of guidewire 103, and then push cannula 187 is advanced down the guidewire. As push cannula 187 is advanced down the guidewire, its distal end 194 pushes the straight, substantially rigid elongated body 184 ahead of it (FIG. 15).

Figure 16:
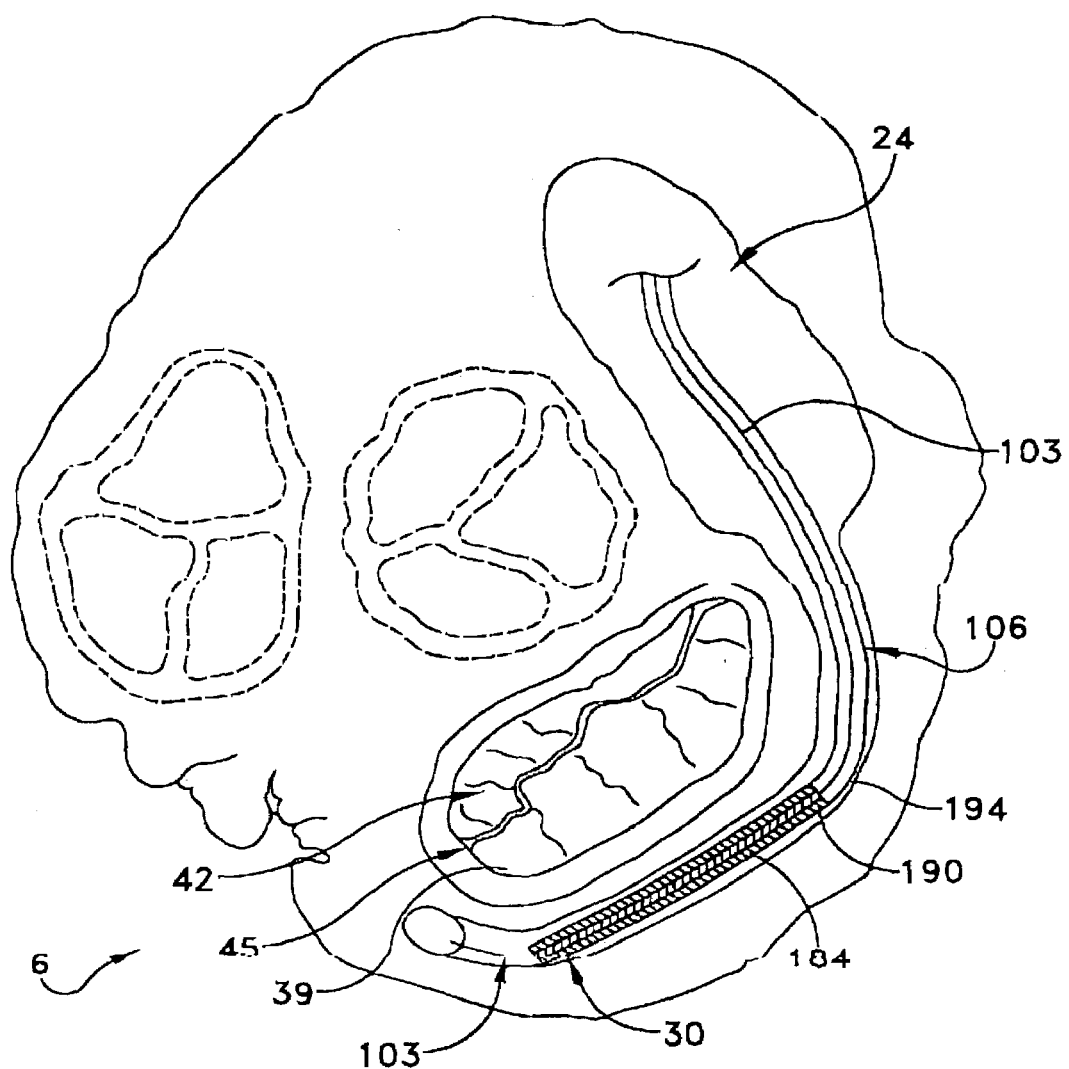

As the straight, substantially rigid elongated body 184 is passed down the coronary sinus 30, it forces the coronary sinus to assume a straight configuration at the point where the straight, substantially rigid elongated body 184 currently resides. Push cannula 187 is pushed down guidewire 103 as needed, until the straight, substantially rigid elongated body 184 is located adjacent to the posterior annulus of the mitral valve (FIG. 16). As this occurs, the presence of the straight, substantially rigid elongated body 184 in the coronary sinus 30 causes the coronary sinus to assume a substantially straight configuration at this point, so that the posterior annulus of the mitral valve is forced anteriorly. This causes the posterior mitral valve leaflet to also move anteriorly so as to improve leaflet coaptation and thereby reduce, or eliminate, mitral valve regurgitation. Using standard visualization means (e.g. echocardiography or fluoroscopy), the exact position of the straight, substantially rigid elongated body 184 may be adjusted so as to reduce, or eliminate regurgitation in the mitral valve.

Figure 16A:
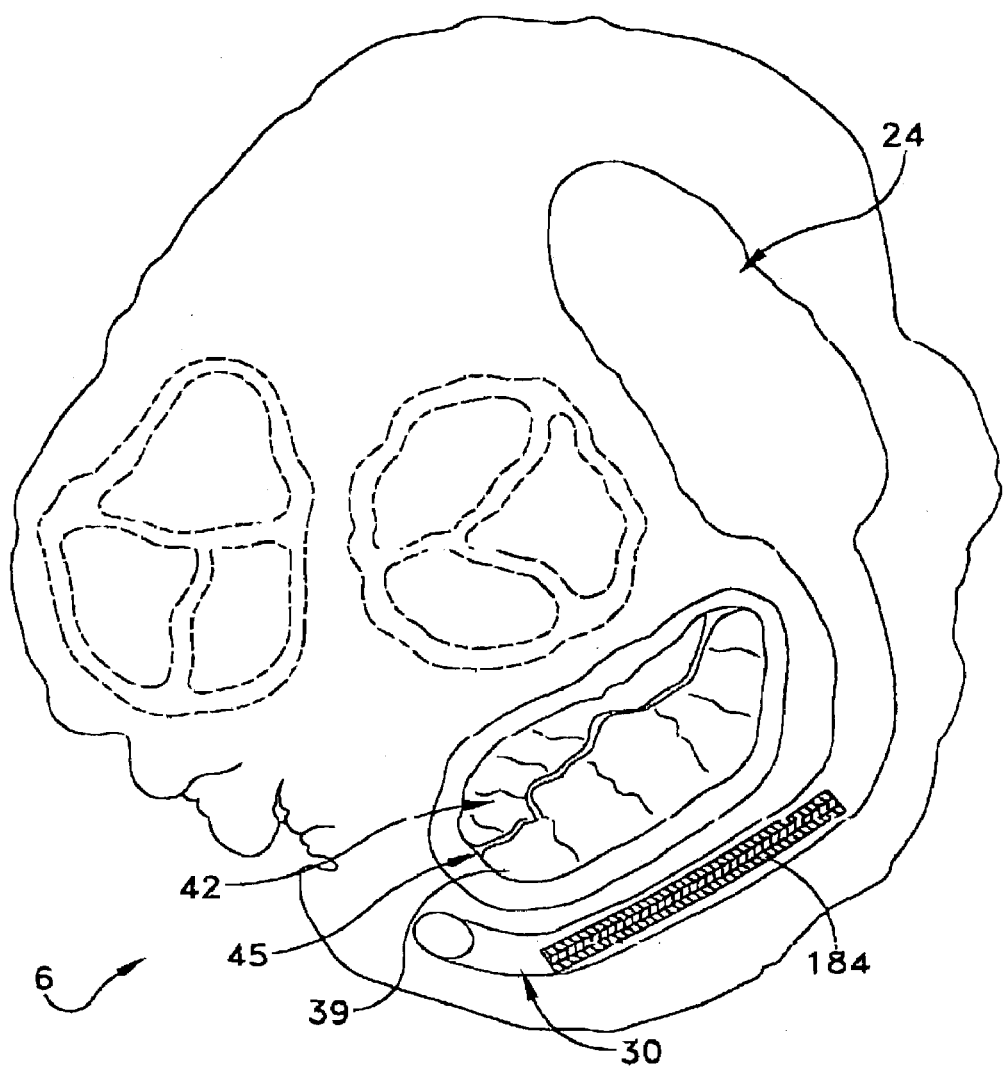
FIGS. 16A–16D illustrate other aspects of the present invention.
Figure 16B:
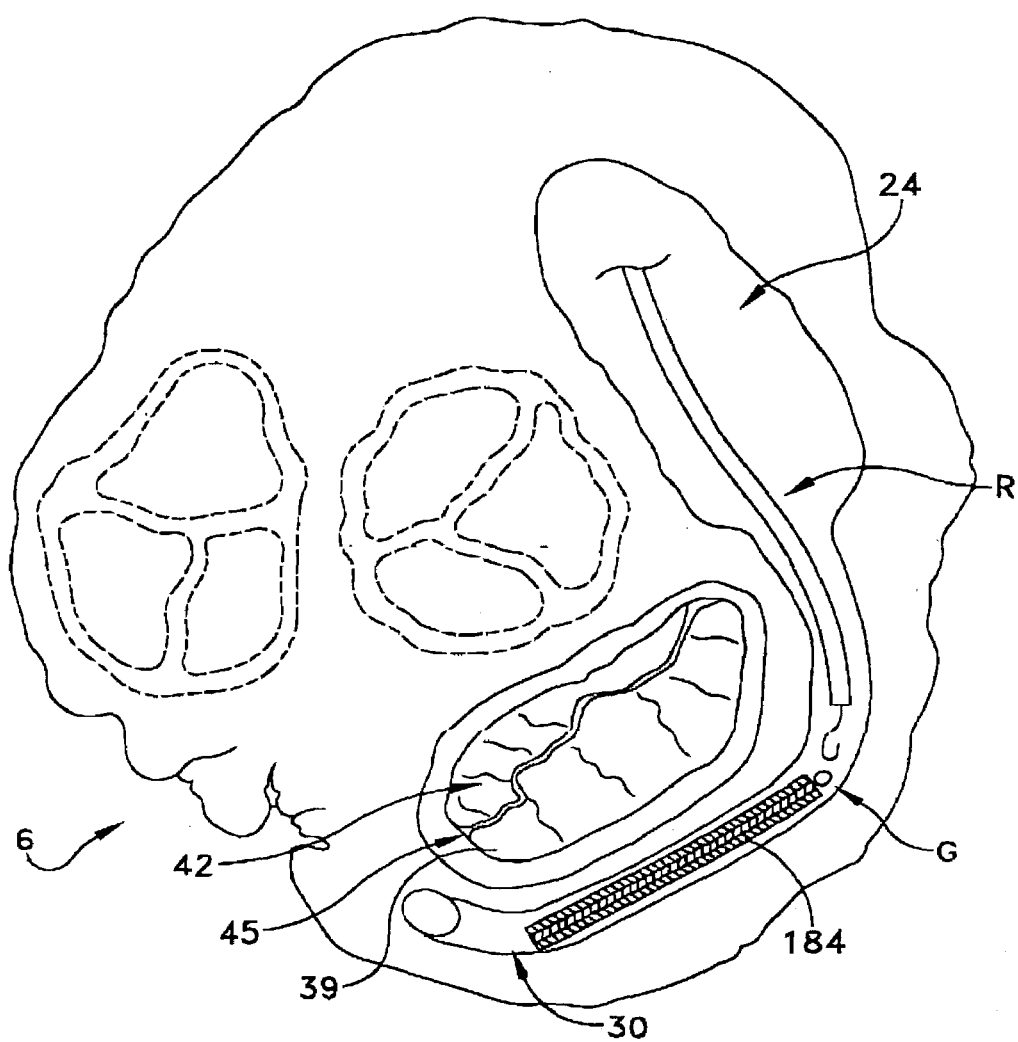

If desired, the push cannula 187 may be provided with a releasably attachable interface (e.g., a grasper) so that it may releasably secure the proximal end 190 of the straight, substantially rigid elongated body 184. Such a feature will permit the straight, substantially rigid elongated body 184 to be pulled backward within the coronary sinus, either for positioning or removal purposes.

Where elongated body 184 is to be left within the body for a substantial period of time, it is possible to leave the apparatus in the position shown in FIG. 16, i.e., with elongated body 184 fit over guidewire 103 and at the end of push cannula 187. Alternatively, guidewire 103 and/or push cannula 187 may be removed, leaving just elongated body 184 deployed at the surgical site (FIG. 16A). To the extent that elongated body 184 may be left by itself at the surgical site, it may be desirable to provide elongated body 184 with an eyelet or hook or other graspable feature G (FIG. 16B) such that a retriever R may thereafter be used to easily grapple and extract the elongated body 184 from the surgical site.

If desired, the straight, substantially rigid elongated body 184 may include relatively flexible portions 175 and/or elongated relatively flexible portions 178 at its distal and proximal ends so as to better distribute the loads on the coronary sinus.

Figure 16C:
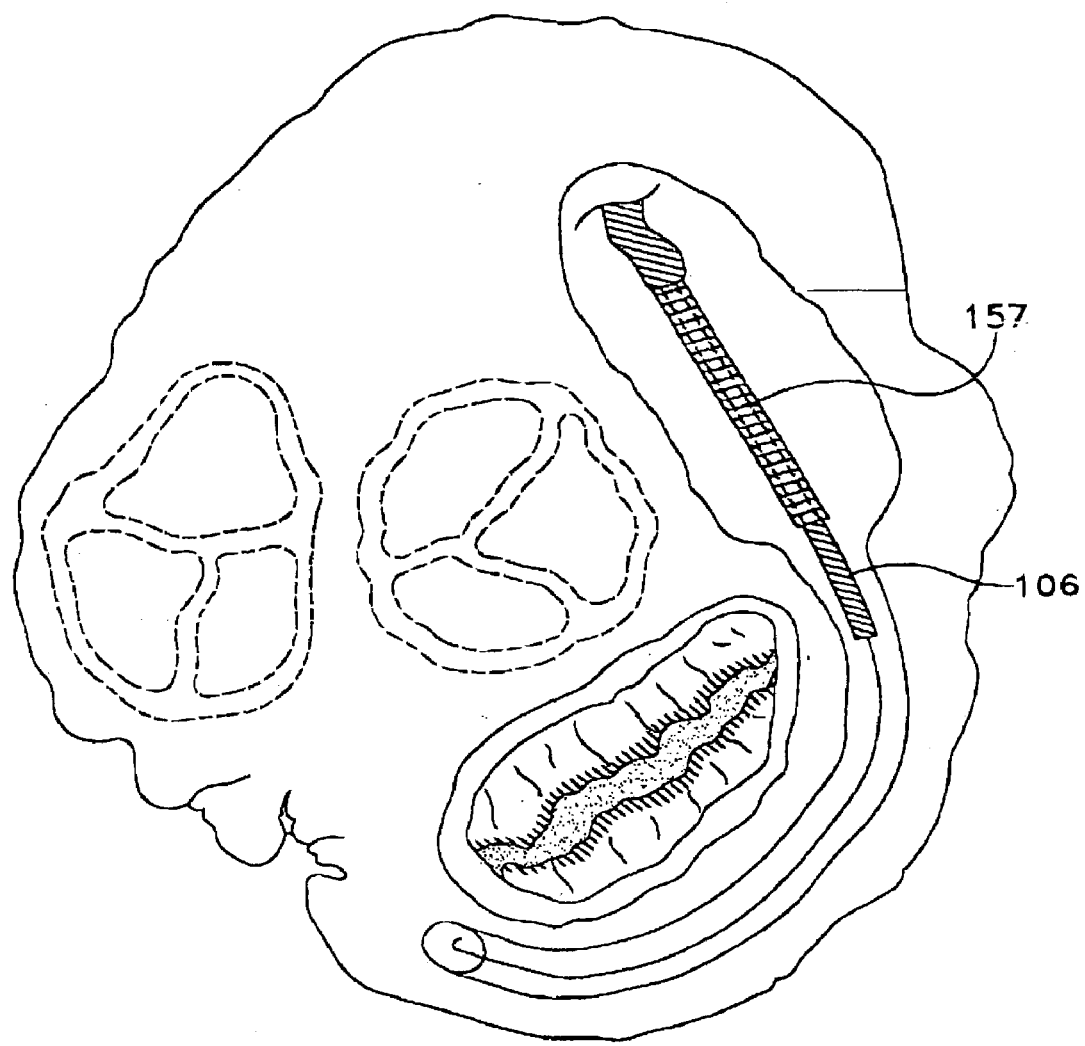
Figure 16D:
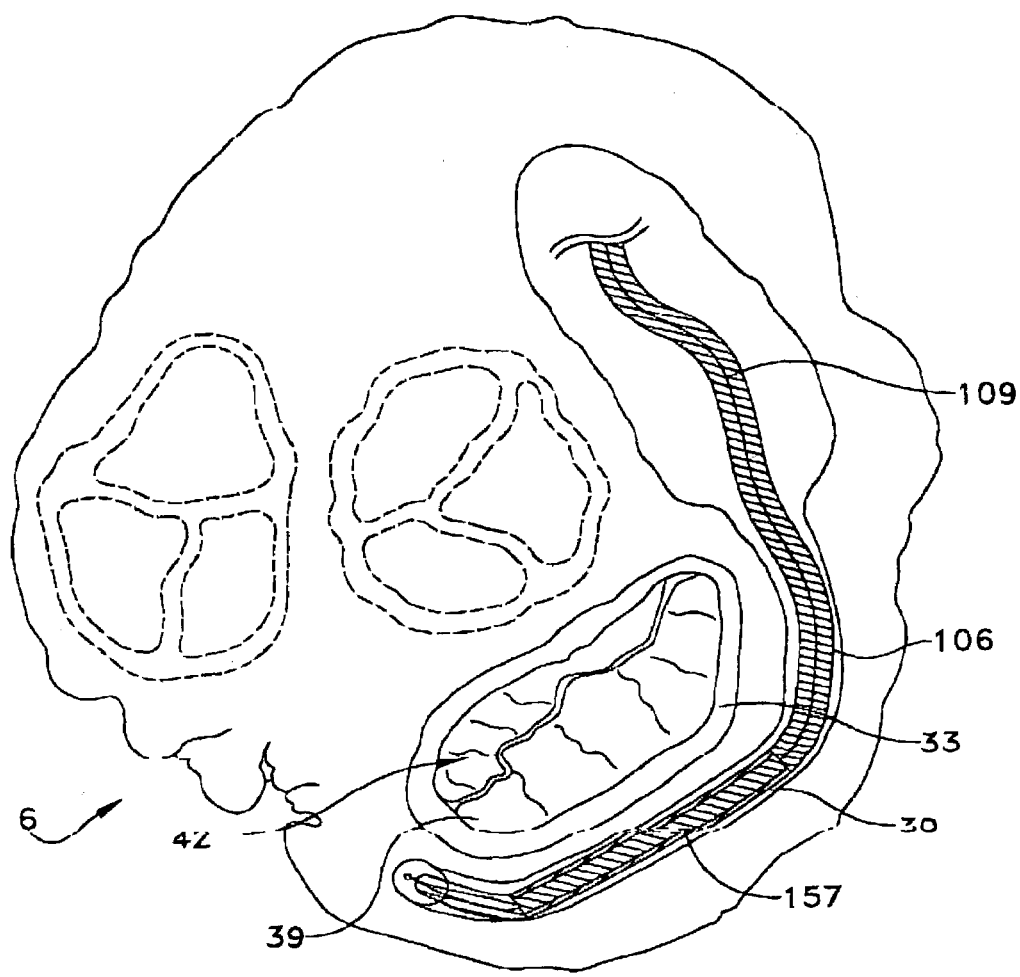

In a further alternative embodiment, straight inflexible body 184 is an integral part of flexible delivery catheter 106 (FIG. 16C). The catheter 106 remains in place after the positioning of the body 184, as shown in FIG. 16D).

When the combination delivery catheter 106 and body 184 is deployed within coronary sinus 30, the flexible delivery catheter 106 serves as a strain relief means. This strain relief means minimizes trauma to the walls of the coronary sinus by spreading the loads at the proximal and distal ends of the body 184 over a greater length of the coronary sinus walls.

Figure 17:
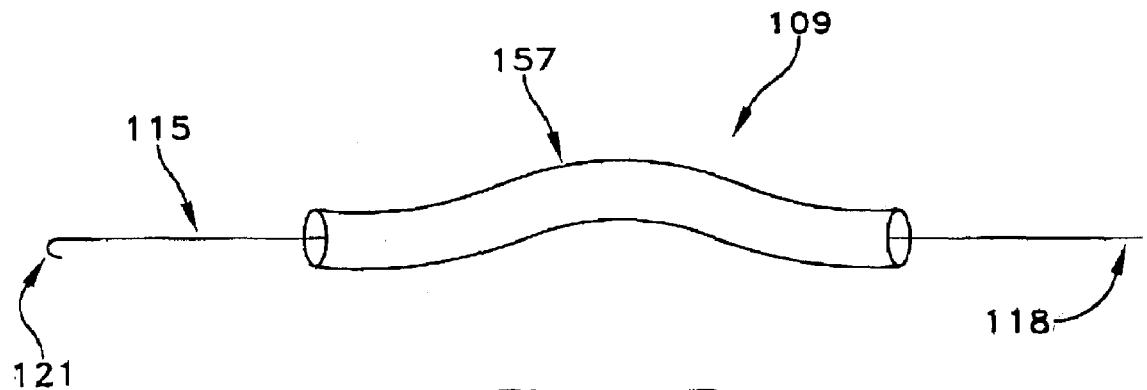
FIGS. 17–20 illustrate still other aspects of the present invention.
Figure 18:
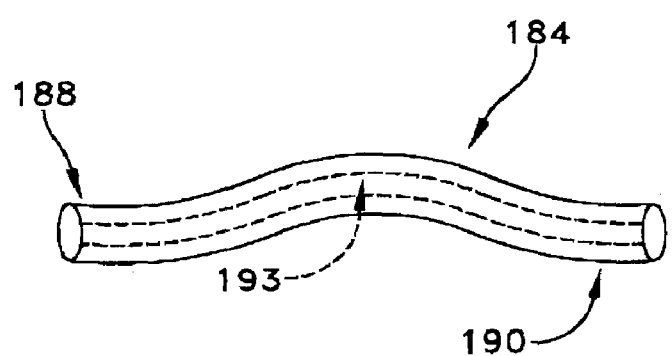
Figure 19:
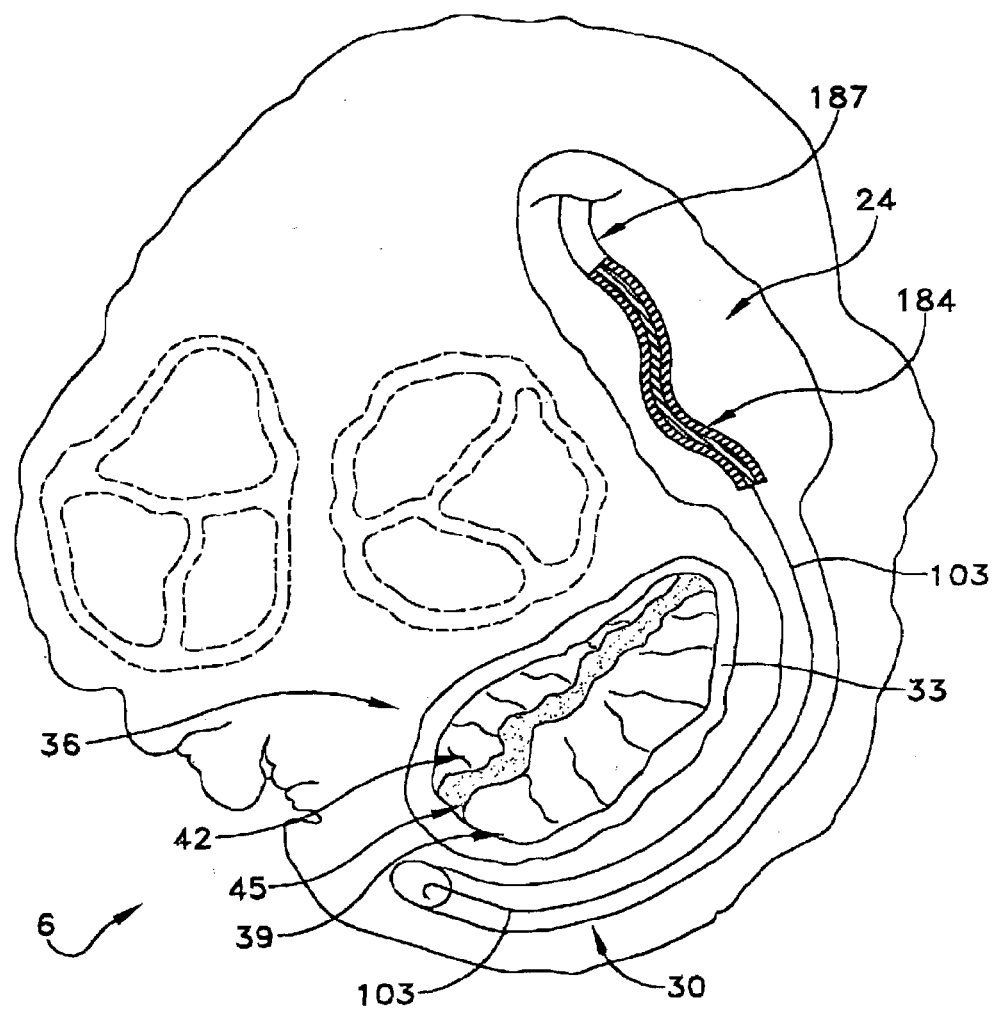
Figure 20:
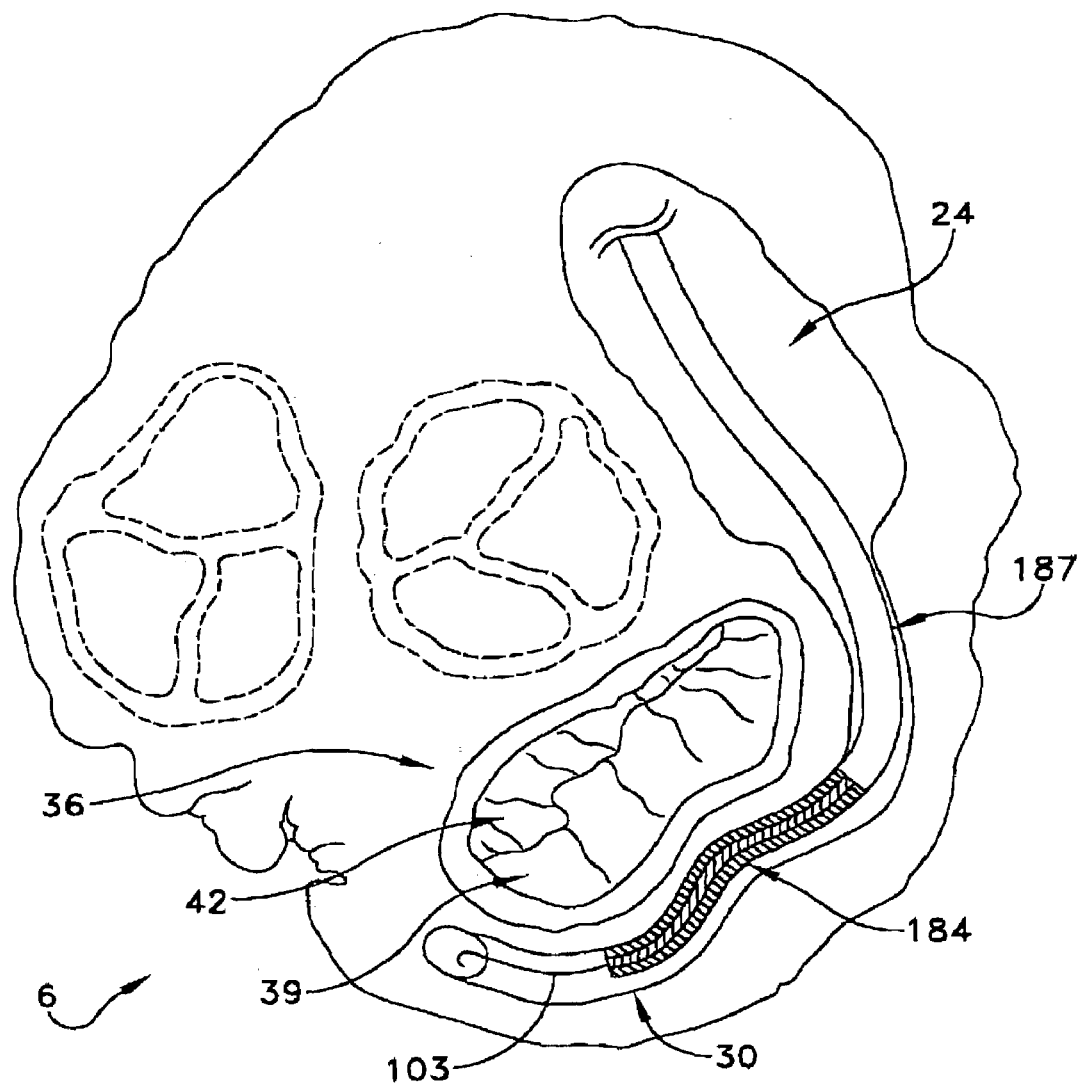

Elongated body 157 and/or elongated body 184 may have any of a variety of non-straight shapes along its length. For example, the elongated body may be wavy, spiraled, or curved along all or a portion of its length. By way of example, elongated body 157 and/or 184 may have a curved configuration so as to invert the natural curvature of the coronary sinus, i.e., so that it is bowed towards the anterior annulus. Or the elongated body may have a compound shape along its length, e.g., it may have a sort of "w" shape, with the center of the "w" being directed towards the anterior annulus. See, for example, FIG. 17, which shows a push rod 109 having an elongated body 157 with a "w" type of shape; and see FIG. 18, which shows an elongated body 184 with a "w" type of shape. See also FIGS. 19 and 20, which show a "w" shaped elongated body 184 being advanced down guidewire 103 (FIG. 19) to a position adjacent to mitral valve 36 (FIG. 20), whereby to reduce mitral regurgitation. Any of the aforementioned elongated body shapes, or other alternative shapes, may effect the anterior displacement of the posterior annulus that results in reduction of the mitral valve regurgitation.

It is preferable that use of the present invention not result in occlusion of coronary sinus 30. Thus, with system 100 shown in FIG. 3, delivery catheter 106 is preferably sized so as to have a diameter less than the diameter of coronary sinus 30, so that blood may flow about the perimeter of delivery catheter 106 when delivery catheter 106 is disposed in coronary sinus 30. Alternatively, and/or additionally, and looking now at FIGS. 21 and 22, delivery catheter 106 may be provided with one or more longitudinally-extending surface grooves SG so as to facilitate blood flow past the perimeter of delivery catheter 106. Similarly, with system 181 shown in FIG. 12, elongated body 184 is preferably sized so as to have a diameter less that the diameter of coronary sinus 30, so that blood may flow about the perimeter of elongated body 184 when elongated body 184 is disposed in coronary sinus 30. Alternatively, and/or additionally, and looking now at FIGS. 23 and 24, elongated body 184 may be provided with one or more longitudinally-extending surface grooves SG so as to facilitate blood flow past the perimeter of elongated body 184.

There are at least three possible configurations for the mitral regurgitation reduction assembly, namely, (i) a non-drop-off body, (ii) a drop-off body with a detachable short length of a delivery catheter and, (iii) a drop-off body without the short delivery catheter segment.

The drop-off body 184 without a short section of delivery catheter is easily appreciated. In one form of the invention, it may comprise the system shown in FIG. 12. In another form of the invention, the push rod 109 is provided with a detachable joint 230 (FIG. 24A) near the proximal end of the body 184. The delivery catheter 106 is introduced into place in the coronary sinus, as described above, the body is advanced into place, and the delivery catheter 106 and push rod 187 are withdrawn, leaving only the body 184 in place, as shown in FIG. 16A.

The drop-off design that leaves a short section of the delivery catheter 106 in place is shown in FIGS. 24A-24D. This design requires an annular locking mechanism between the body and the delivery catheter 106. Embodiments of annular locking mechanism are described hereinbelow. The drop-off embodiment requires a break-away joint 232 in the delivery catheter 106, as well as the breakaway joint 230 in the push rod 12A.

In the non-drop-off design (FIGS. 24E, 24F and 24G) the delivery catheter 106 remains indwelling and extends from the body 157 (or 184) all the way to the puncture site 234. The non-drop-off prosthetic bodies (active or passive) are identical to their diagnostic counterparts, with the additional needs for a long term, reliable anchor and proximal termination of the delivery catheter 106 and push rod 109.

Once the body 157 or 184 is correctly placed, the delivery catheter 106 (and push rod 109 in the case of body 157) are snipped and terminated near the perforation site 234. This site will be the neck, chest or thigh in the case of a jugular, subclavian or femoral vein approach, respectively. Crimping and/or adhesive bonding in the annular space between the push rod and the delivery catheter provides reliable fixation of these two components. Once these components have been secured, the proximal end of the assembly is capped and terminated in a manner similar to the techniques used to implant subcutaneous pacing leads. The fixation of the delivery catheter 106 to the push rod/body assembly assures that there can be no relative motion between these components, and therefore the body 157, 184 cannot migrate within the delivery catheter 106.

Figure 24A:
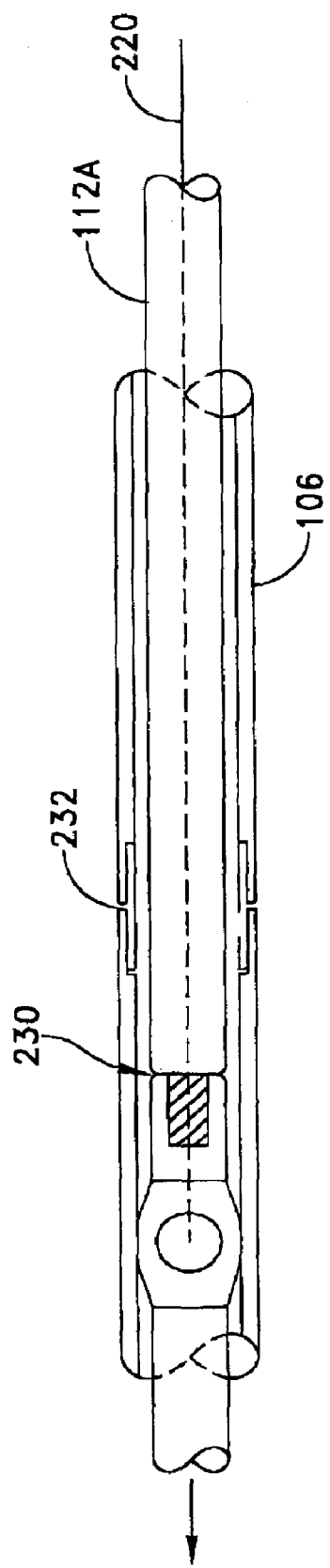
FIG. 24A is a diagrammatic illustration of another feature of the invention.
Figures 24B, 24C, 24D:
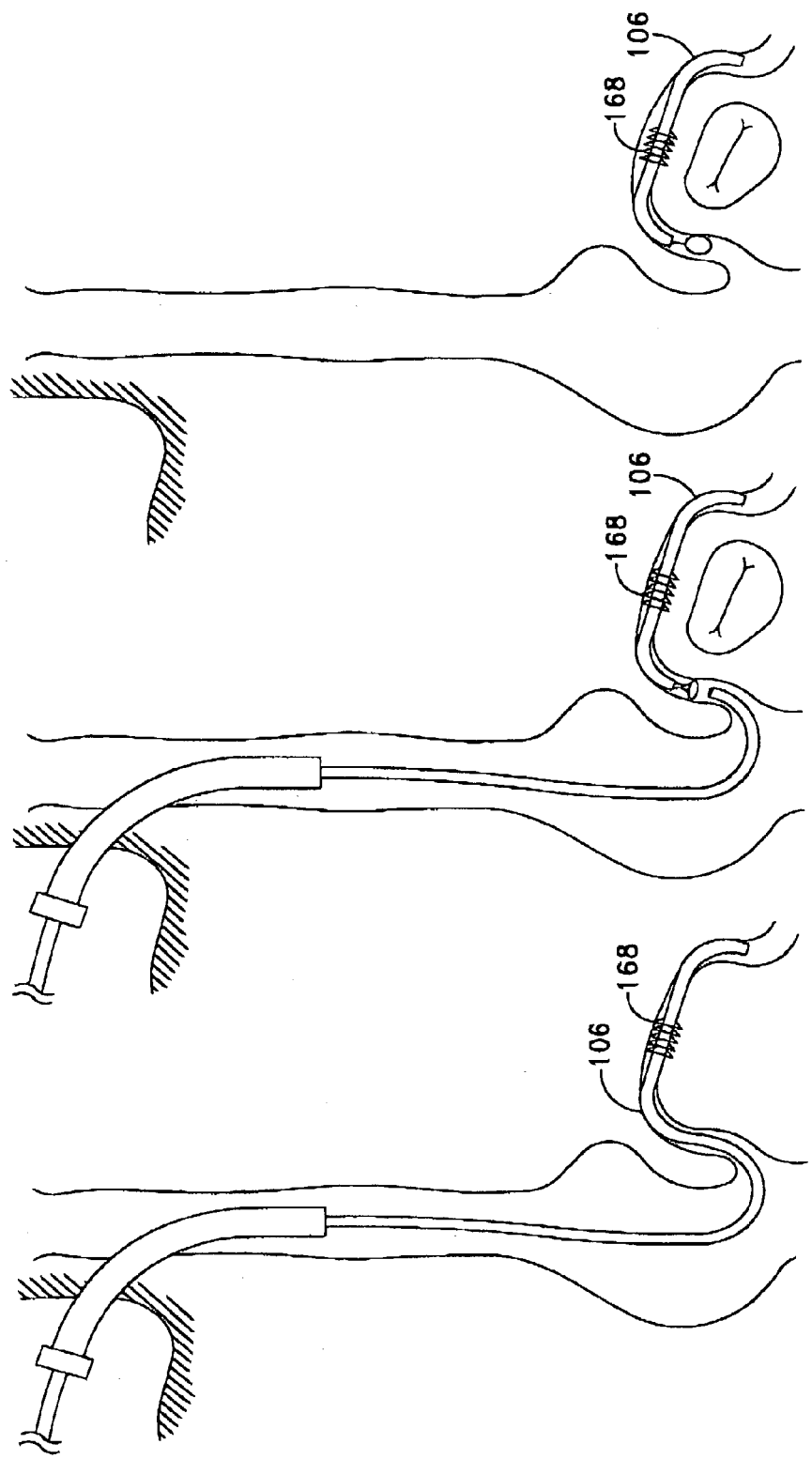
Figure 24H:
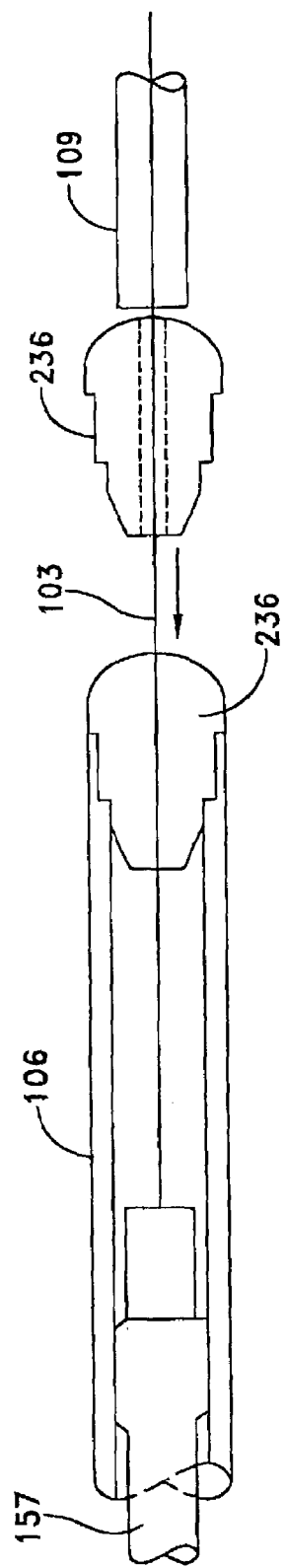
Figure 24J:
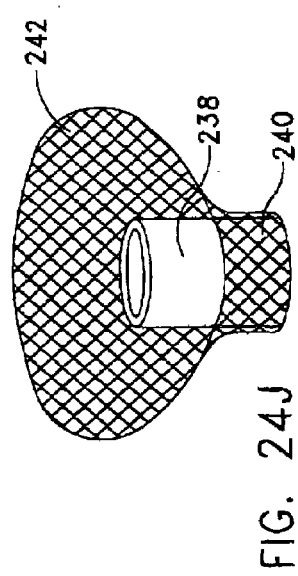
Figure 24K:
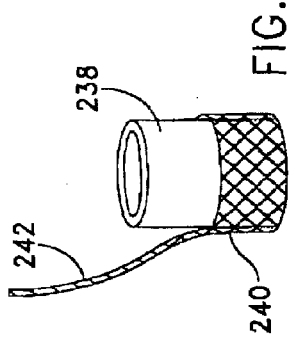
Figure 24L:
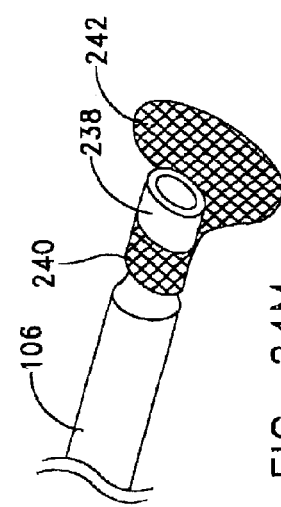
Figure 24M:
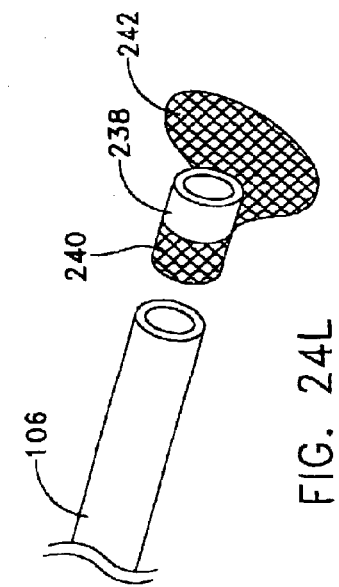
Figure 24N:
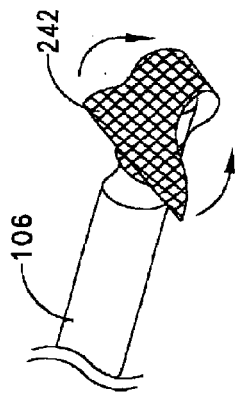
Figure 24O:
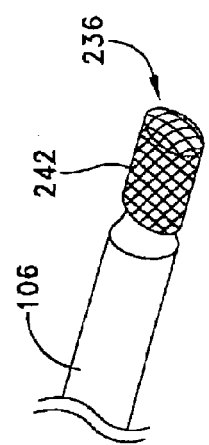

An additional feature of prosthetic designs that leave an indwelling delivery catheter is the ability to close the proximal end of the catheter. It is desirable to close off this relatively large lumen to avoid clot formation within the lumen, and the concomitant risk of embolus. A cap 236 designed to permit this closure is shown in FIG. 24H. The cap 236 can close the delivery catheter 106 at any point along its length, from the proximal end of a non-drop-off prosthetic device to the proximal end of the drop-off prosthetic device.

A second embodiment of a delivery catheter cap is shown in FIGS. 24J-24O. This device is constructed of a short length of malleable metal 238 surrounded by a woven mesh collar 240 fixed to a mesh tab 242. When terminating the system with this cap, the delivery catheter 106 and push rod are sectioned as before. The cap is then slid over the end of the delivery catheter 106, the collar 240 of the crimp is crushed onto the delivery catheter (FIG. 24M), securely locking the delivery catheter and push rod together. The woven mesh tab 242 is then folded over the mesh collar 240 and delivery catheter 106 (FIG. 24N) and pressed against the mesh collar 240 and catheter 162.

In system 100 (FIG. 3) and in system 181 (FIG. 12), the elongated bodies 157 and 184 are shown completely formed prior to their deployment in the patient. However, it is also possible to form elongated body 157 and/or elongated body 184 in situ from a plurality of smaller elements.

Thus, for example, in FIGS. 25–27 there is shown an alternative form of push rod 109 for use with guidewire 103 and delivery catheter 106. More particularly, push rod 109 comprises flexible body 148 and a plurality of substantially rigid elongated elements 157A, 157B, 157C, etc. which collectively form the complete elongated body 157. Preferably, the distalmost elongated element 157A is fixed to flexible body 148 while the remaining elongated elements 157B, 157C, 157D, etc. are free to slide on flexible body 148. In addition, elongated elements 157A, 157B, 157C, etc. preferably include connectors C for permitting one elongated element to be secured to a neighboring elongated body. The connectors C shown in FIG. 25 comprise male and female screw type connectors; however, other types of connectors may also be used.

By assembling the elongated body 157 in situ using a plurality of elongated elements 157A, 157B, 157C, etc., it is possible to create an elongated body 157 which is perfectly sized to the needs of the patient.

Figure 28:
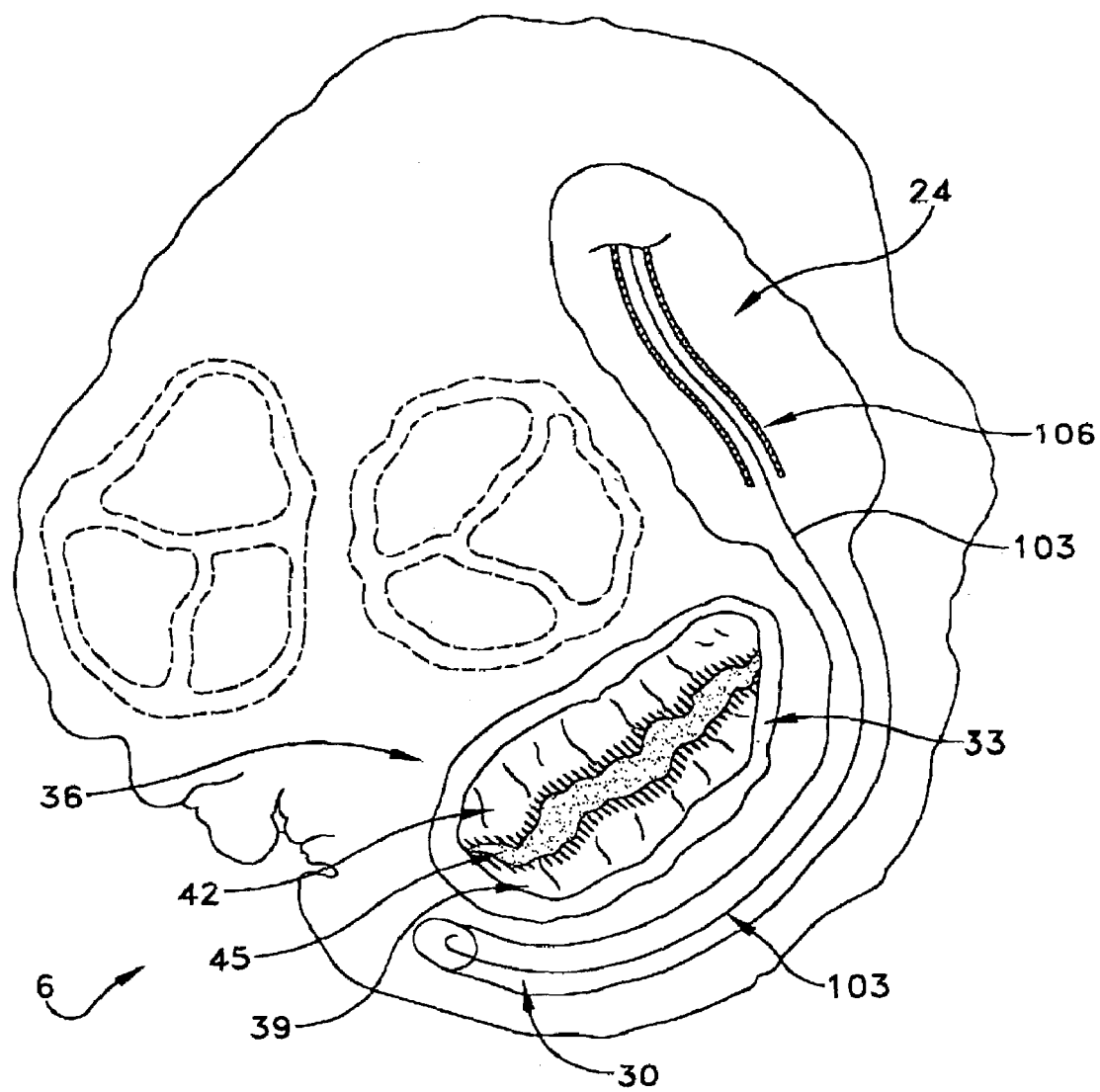
FIGS. 28–32 illustrate the embodiment of FIGS. 25–27 in use.
Figure 29:
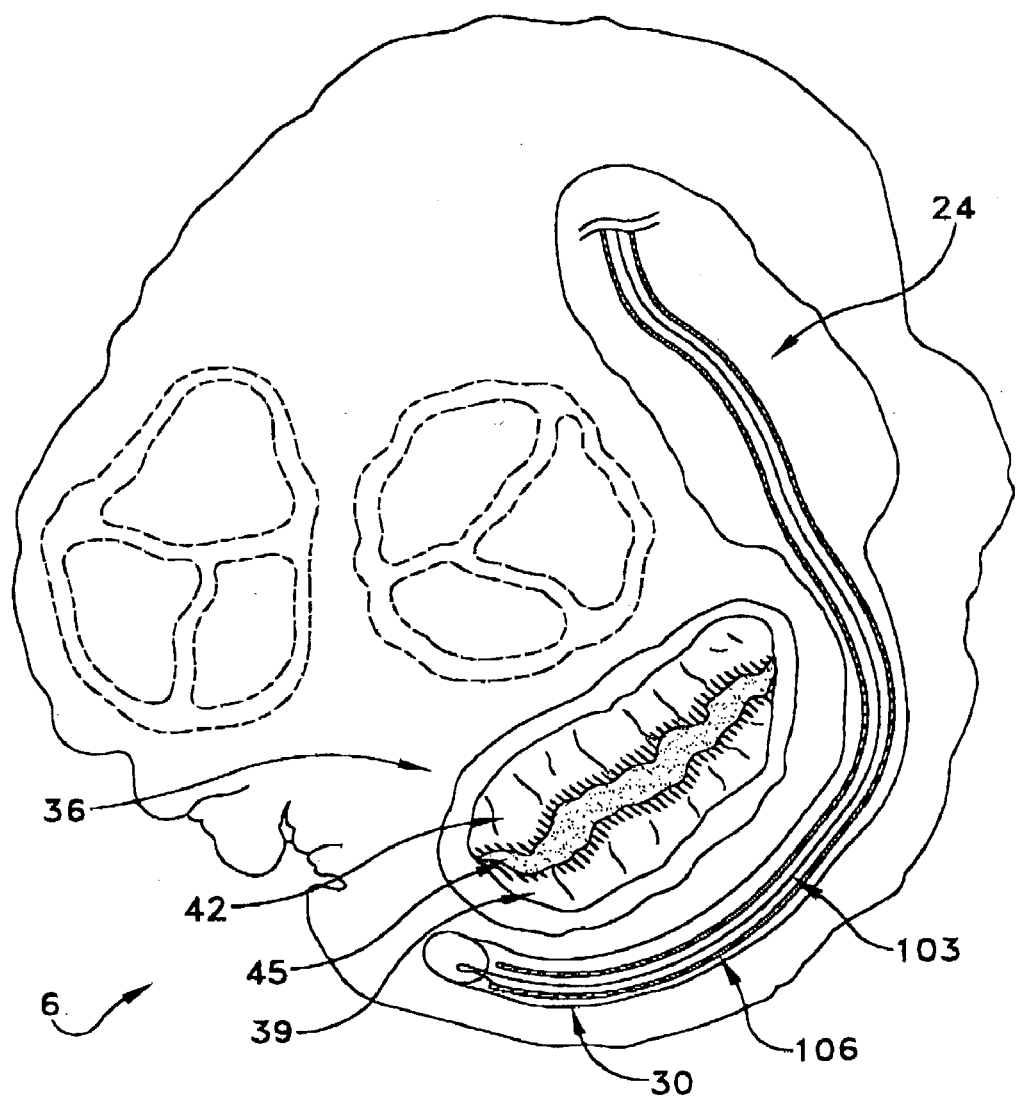
Figure 30:
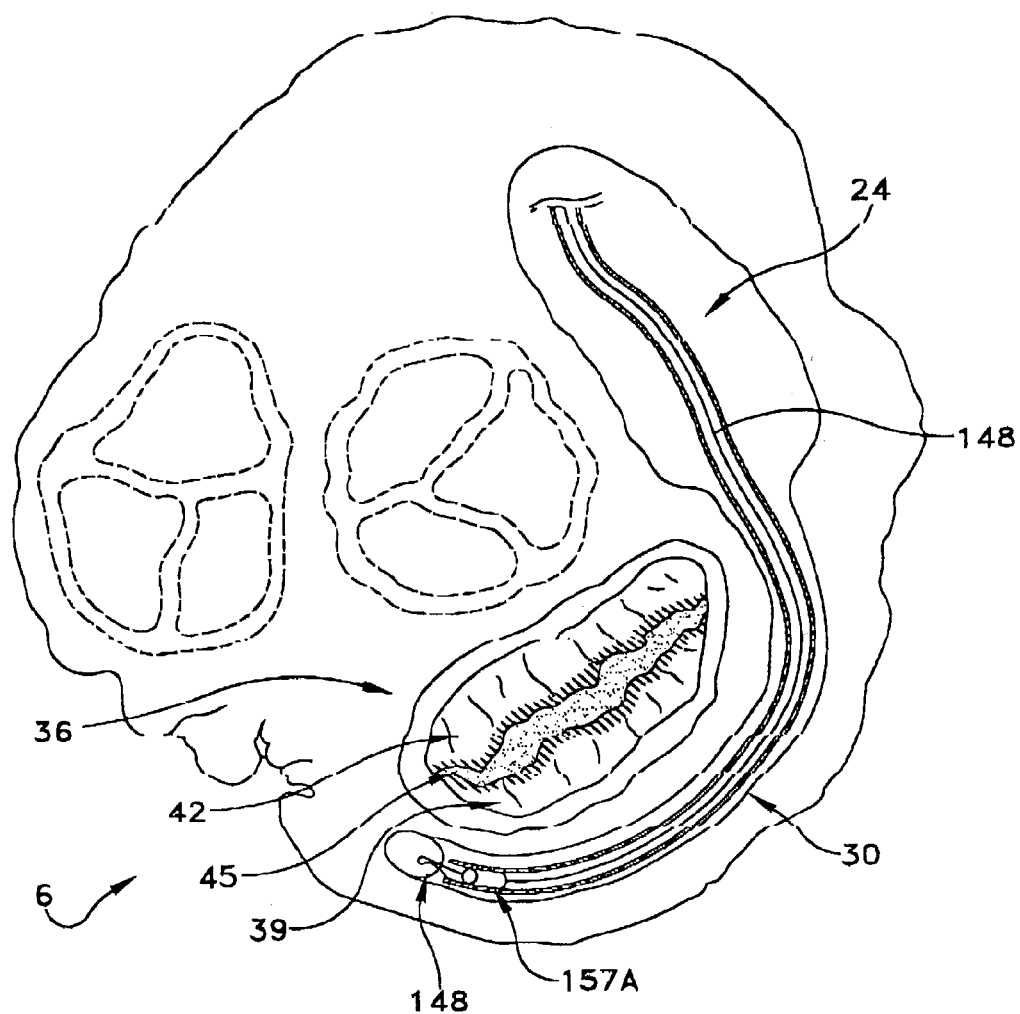
Figure 31:
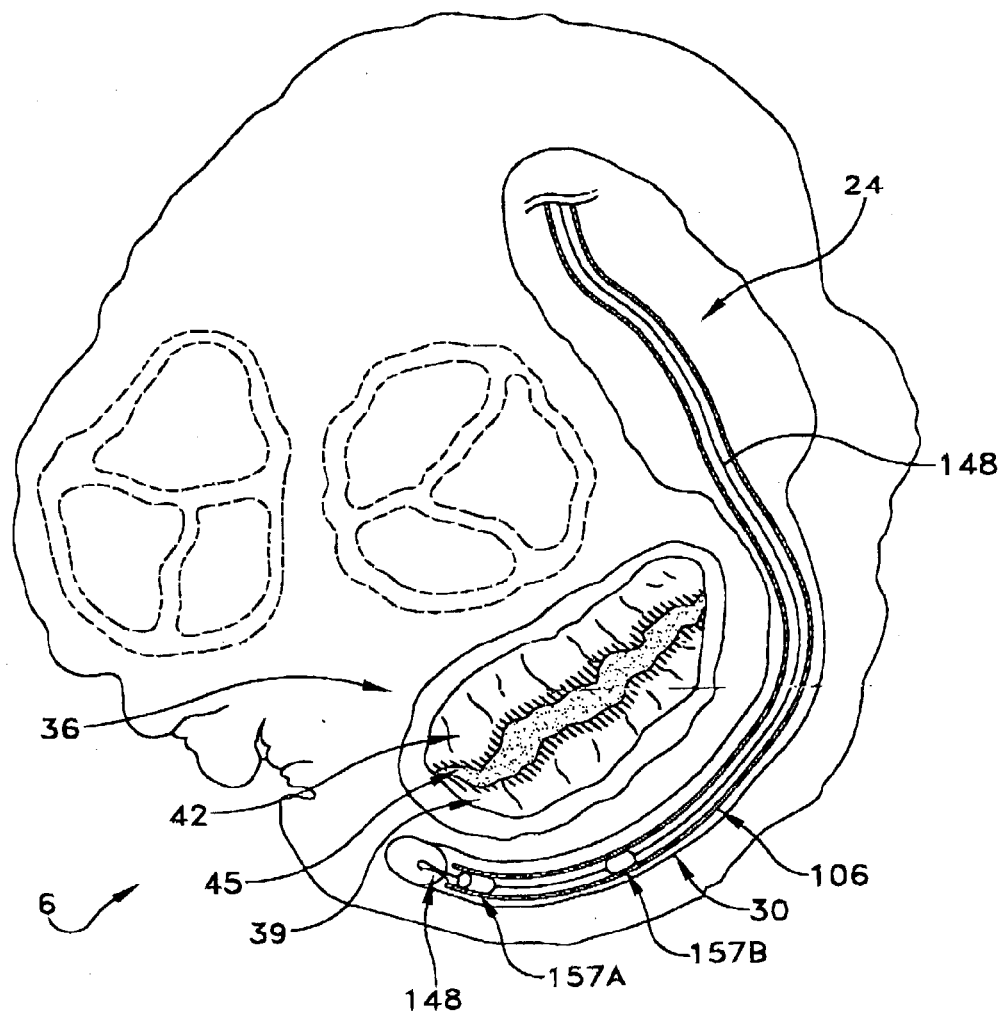

The push rod 109 shown in FIGS. 25–27 may be used as follows. First, guidewire 103 is passed down to the coronary sinus 30 (FIG. 28). Then delivery catheter 106 is passed down guidewire 103 and into the coronary sinus (FIGS. 28 and 29). Then the guidewire 103 is withdrawn from the surgical site and replaced by the push rod's flexible body 148 with elongated element 157A attached (FIG. 30). Next, a plurality of elongated elements 157B, 157C, 157D, etc. are slid down flexible body 148 (FIG. 31) and secured to elongated element 157A (and any preceding elongated element). As many elongated elements 157A, 157B, 157C, etc. are used as is necessary to effect the desired leaflet coaptation (FIG. 32).

In FIGS. 32A–32C, there is shown another form of push rod 109. More particularly, with this form of the push rod, elongated body 157 is formed by a plurality of elongated elements 157A, 157B, 157C, etc. which collectively form the complete elongated body 157. Preferably the distalmost elongated element 157A is fixed to flexible body 148 while the remaining elongated elements 157A, 157B, 157C, etc. are free to slide on flexible body 148. With this version of the invention, elongated body 157 may be formed in situ by moving elongated elements 157A, 157B, 157C, etc. distally, with distalmost elongated element 157A acting as a distal stop, and then keeping elongated elements 157A, 157B, 157C, etc. biased distally with a holding mechanism, e.g., a crimp CR.

Figure 32:
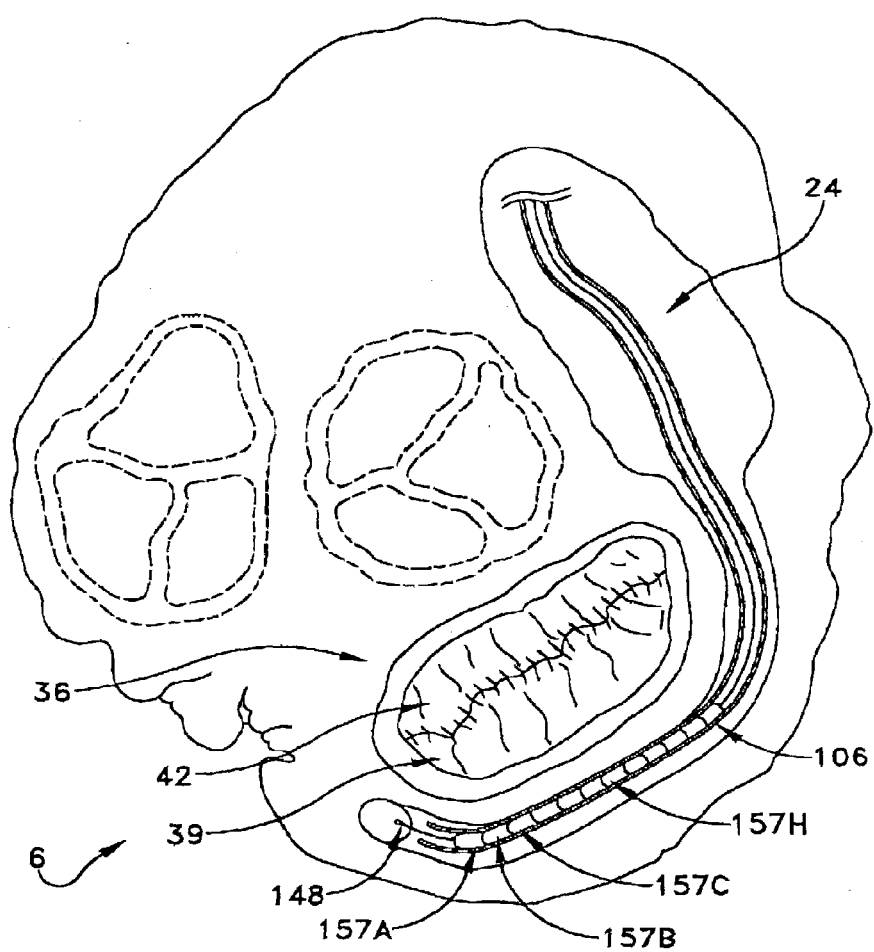
Figure 32D:
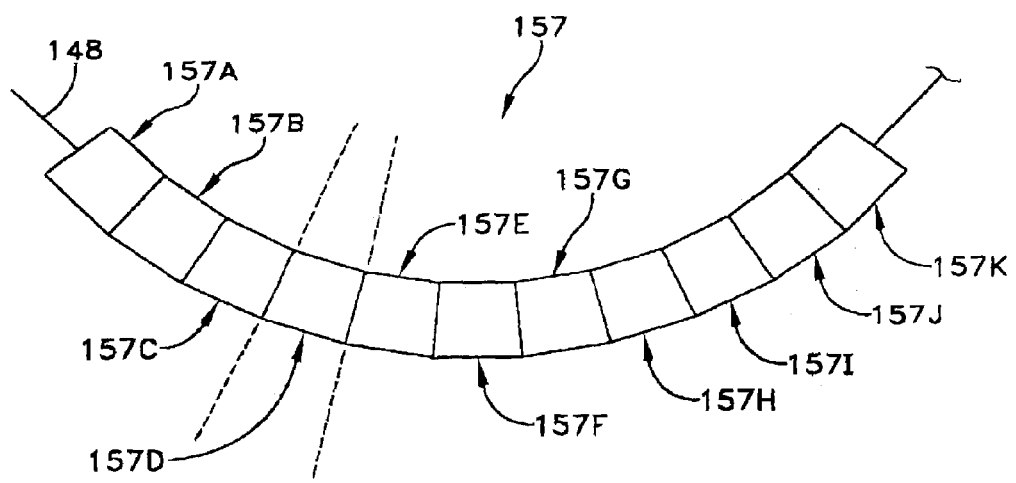
Figure 32E:
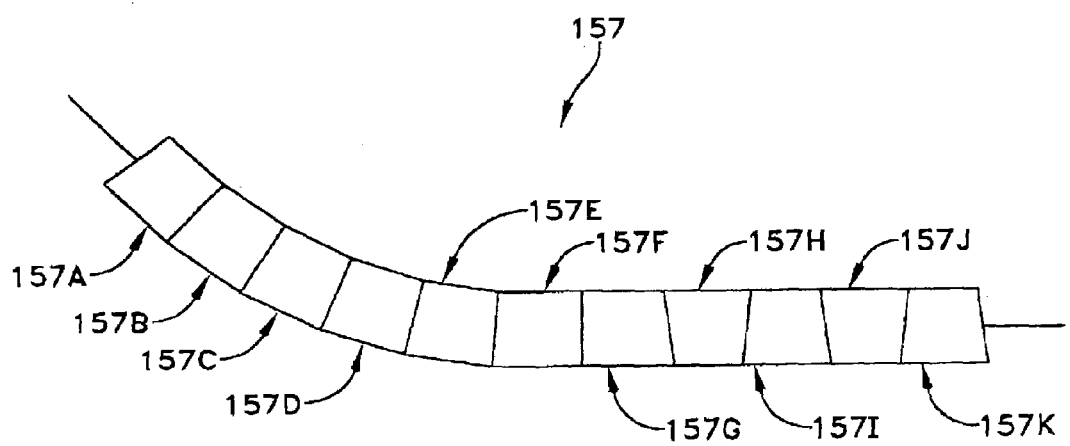

In FIGS. 25–32, and in FIGS. 32A–32C, elongated elements 157A, 157B, 157C, etc. are shown configured so as to form a substantially straight elongated body 157. However, if desired, elongated elements 157A, 157B, 157C, etc. could have alternative configurations so as to form other body shapes. Thus, for example, in FIG. 32D elongated elements 157A, 157B, 157C, etc. are shown forming a curved elongated body 157, and in FIG. 32E elongated elements 157A, 157B, 157C, etc. are shown forming a composite curved-and-straight elongated body 157. It will be appreciated that still other shapes may be formed by elongated elements 157A, 157B, 157C, etc. In this respect, it will be appreciated that the shapes of elongated body 157 may be established either by (1) forming elongated elements 157A, 157B, 157C, etc. so that they have only one possible way of being assembled together, or (2) by forming elongated elements 157A, 157B, 157C, etc. so that they have multiple ways of being assembled together. In this latter situation, one possible way to vary the final configuration of elongated body 157 is by individually rotating various ones of elongated elements 157A, 157B, 157C, etc., e.g., such as is shown in FIGS. 32D and 32E.

As noted above, it is also possible to form the elongated body 184 of system 181 (FIG. 12) in situ from a plurality of smaller elements.

Figure 33:
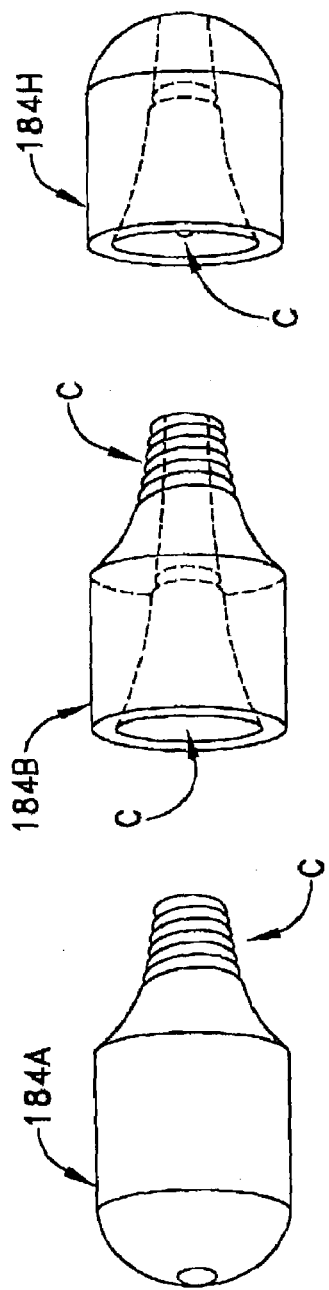
FIGS. 33 and 34 illustrate another form of the present invention.
Figure 34:
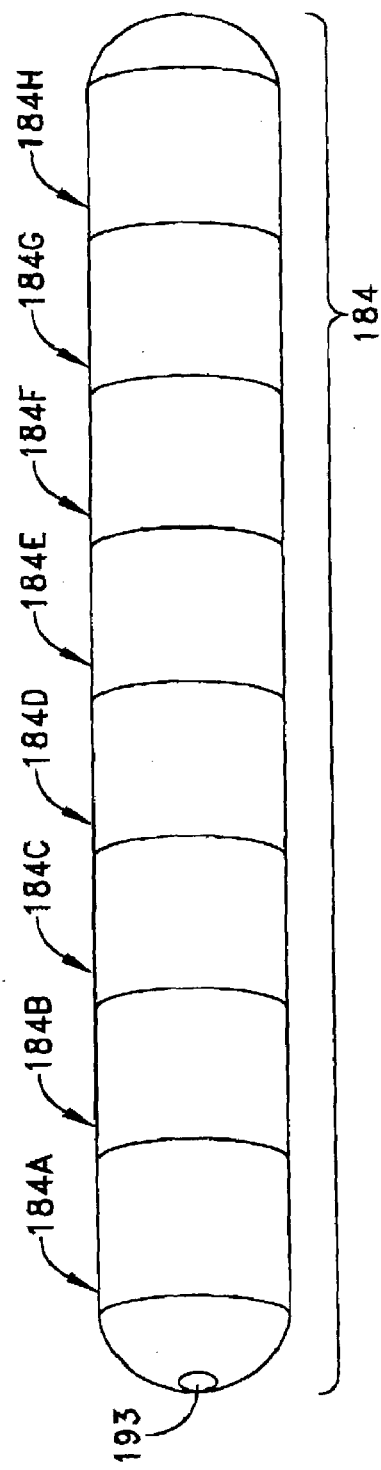

Thus, for example, in FIGS. 33 and 34 there is shown an alternative form of elongated body 184 which comprises a plurality of substantially rigid elongated elements 184A, 184B, 184C, etc. which collectively form the complete elongated body 184. In addition, elongated elements 184A, 184B, 184C, etc. preferably include connectors C for permitting one elongated element to be secured to a neighboring elongated element. The connectors C shown in FIGS. 25 and 33 comprise male and female screw type connectors; however, other types of connectors may also be used.

By assembling the elongated body 184 in situ using a plurality of elongated elements 184A, 184B, 184C, etc., it is possible to create an elongated body 184 which is perfectly sized to the needs of the patient.

Figure 35:
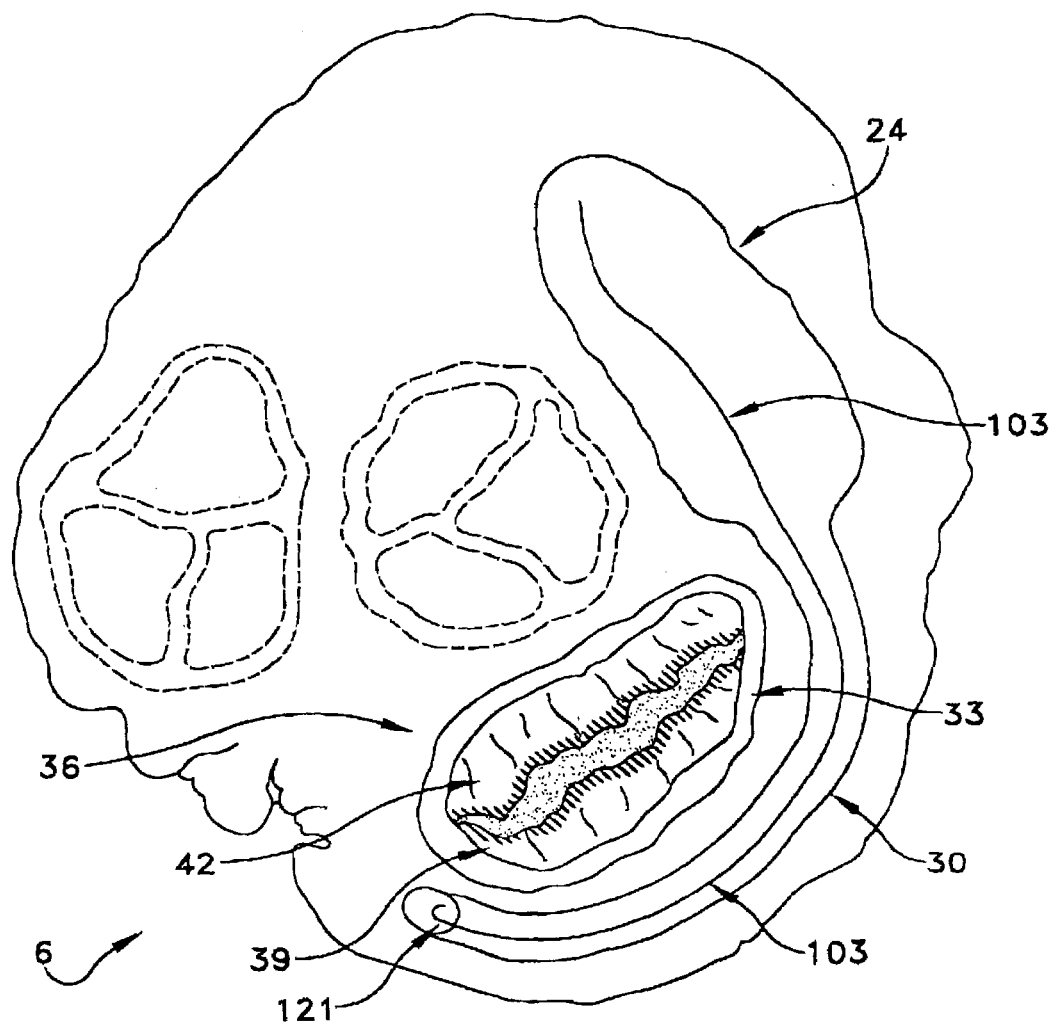
FIGS. 35–37 illustrate the embodiment of FIGS. 33 and 34 in use.
Figure 36:
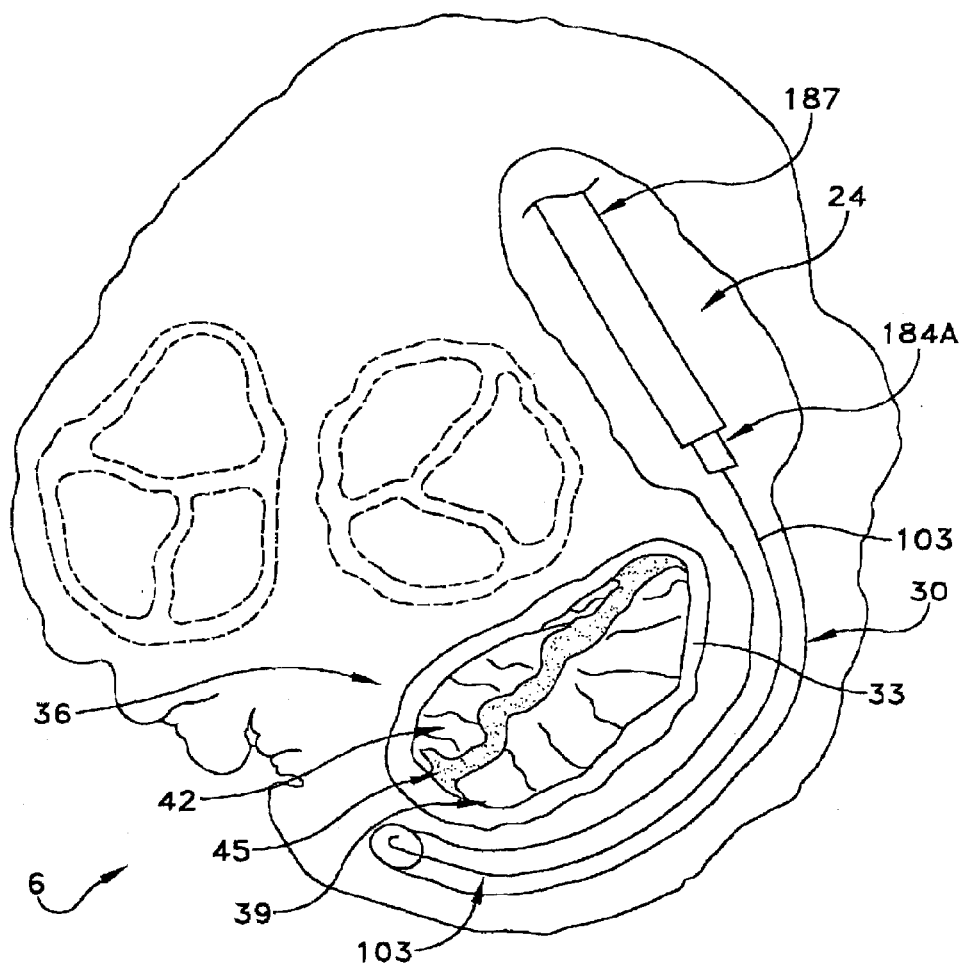
Figure 37:
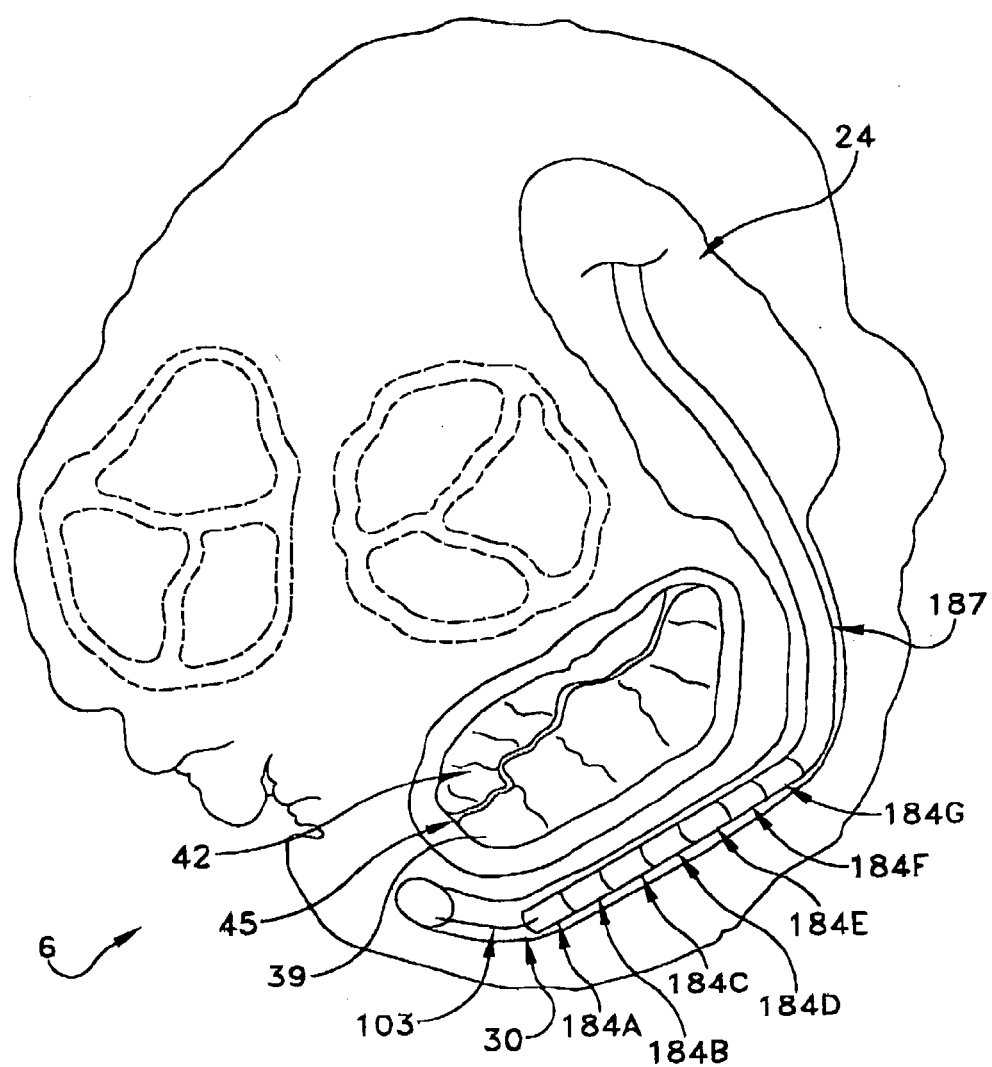

The elongated body 184 shown in FIGS. 33 and 34 may be used as follows. First, guidewire 103 is passed down coronary sinus 30 (FIG. 35). Then push cannula 187 is used to push a plurality of elongated elements 184A, 184B, 184C, etc. down guidewire 103 and into the coronary sinus (FIGS. 36 and 37). As many elongated elements 184A, 184B, 184C, etc. are used as is necessary to effect the desired leaflet coaptation (FIG. 37).

In FIGS. 37A–37C, there is shown another form of elongated body 184. More particularly, with this form of elongated body, the elongated body 184 is formed by a plurality of elongated elements 184A, 184B, 184C, etc. which collectively form the complete elongated body 184. Preferably, all of the elongated elements 184A, 184B, 184C, etc. are free to slide on guidewire 103. With this version of the invention, elongated body 184 may be formed in situ by moving elongated elements 184A, 184B, 184C, etc. distally and then drawing them tightly together, e.g., such as by using a cinching system such as that shown in FIG. 37C and comprising a distal member DM and a crimp CR.

Figure 37D:
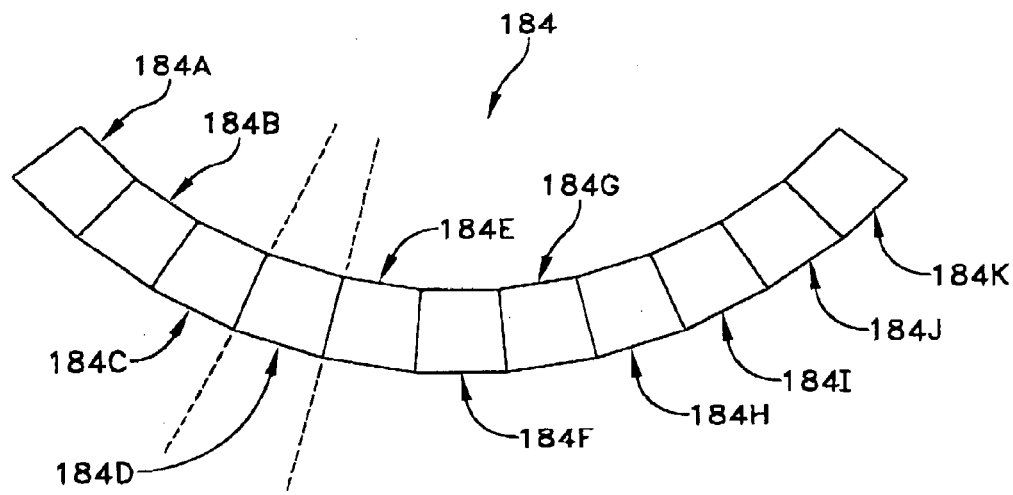
FIGS. 37D and 37E illustrate another aspect of the present invention.
Figure 37E:
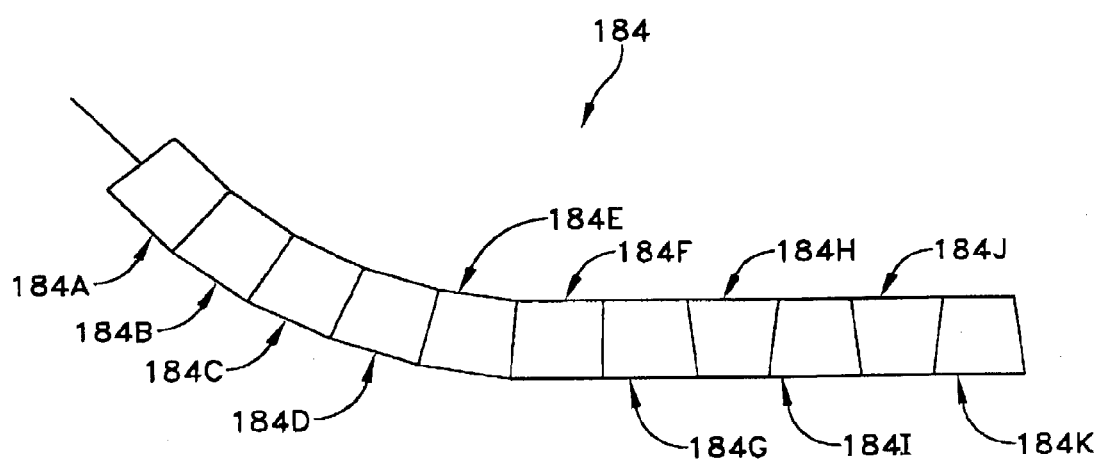

Again, in FIGS. 33–37, and in FIGS. 37A–37C, elongated elements 184A, 184B, 184C, etc. are shown configured so as to form a substantially straight elongated body 184. However, if desired, elongated elements 184A, 184B, 184C, etc. could have alternative configurations so as to form other body shapes. Thus, for example, in FIG. 37D elongated elements 184A, 184B, 184C, etc. are shown forming a curved elongated body 184, and in FIG. 37E elongated elements 184A, 184B, 184C, etc. are shown forming composite curved-and-straight elongated body 184. It will be appreciated that still other shapes may be formed by elongated elements 184A, 184B, 184C, etc. In this respect it will be appreciated that the shapes of elongated body 184 may be established either by (1) forming elongated elements 184A, 184B, 184C, etc. so that they have only one possible way of being assembled together, or (2) by forming elongated elements 184A, 184B, 184C, etc. so that they have multiple ways of being assembled together. In this latter situation, one possible way to vary the final configuration of elongated body 184 is by individually rotating various ones of elongated elements 184A, 184B, 184C, etc., e.g., such as is shown in FIGS. 37D and 37E.

Looking next at FIGS. 37F–37I, there is shown another form of push rod 109 having an elongated body 157 formed by a plurality of elongated elements 157A, 157B, 157C, etc. Each of the elongated elements 157A, 157B, 157C, etc. is attached to flexible body 148 and is separated from adjacent elongated elements by a gap G. By orienting gaps G radially away from mitral valve 36 (FIG. 37H), push rod 109 will be able to curve as required so as to follow the natural curvature of the coronary sinus, e.g., during insertion of push rod 109 into coronary sinus 30. However, by rotating flexible body 148 about its axis so that gaps G are oriented 180 degrees opposite to that shown in FIG. 37H (i.e., as shown in FIG. 37I), gaps G will be closed and push rod 109 will be straightened, whereby to apply an anteriorly-directed force to the posterior annulus of mitral valve 36 and reduce mitral regurgitation.

Figure 37J:
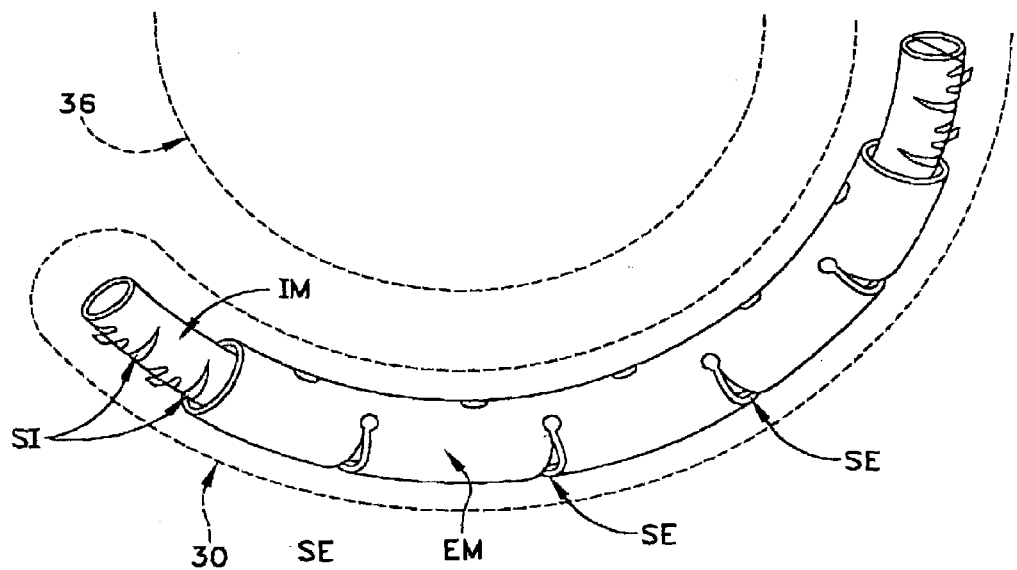
FIGS. 37J and 37K illustrate yet another aspect of the present invention.
Figure 37K:
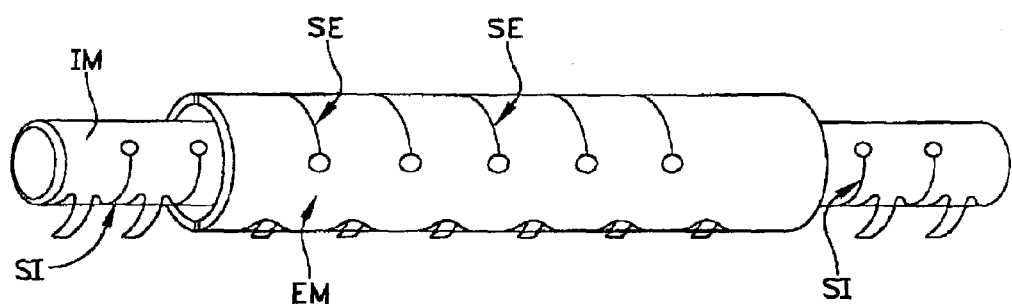

Looking next at FIGS. 37J and 37K, there is shown another form of the invention. In this construction, an internal member IM has a plurality of slots SI and an external member EM has a plurality of slots SE. Internal member IM is concentrically received within external member EM. By orienting internal member IM and external member EM so that slots SI are aligned with slots SE (FIG. 37J), internal member IM and external member EM may be curved as required so as to follow the natural curvature of the coronary sinus, e.g. during insertion of the members into the coronary sinus. However, by orienting internal member IM and external member EM so that slots SI are oriented away from slots SE (FIG. 37K), internal member IM and external member EM will be straightened, whereby to apply an anteriorly-directed force to the posterior annulus of the mitral valve and reduce mitral regurgitation.

In FIGS. 37L and 37M, there is shown a body assembly comprising two rigid tubes 262, 264 with an internal rod 266 comprised of three sections. The first and third sections 268, 270 of the internal rod 266 are made from a generally flexible material, while the middle section 272 is made from inflexible material. When the flexible sections 268, 270 span the gap between the outer, rigid tubes 262, 264, the assembly can flex at the central point (FIG. 37L). Once the assembly is in place, the rigid rod portion 272 is pulled into place to span the gap between the outer tubes, generating a rigid, straight assembly (FIG. 37M). When removal of the assembly is desired, the rod is pulled by a pull wire 274 until the flexible segment 268 spans the gap, and the body 157 can once again flex in the middle.

It is also possible to form elongated body 157 of push rod 109 (FIG. 3) with an inflatable construction. More particularly, and looking next at FIG. 38, there is shown a push rod 109 having an inflatable elongated body 157 in the form of a balloon B. The push rod's flexible body 148 includes an inflation lumen L which communicates with the interior of balloon B, whereby fluid may be supplied to the interior of the balloon so as to inflate the balloon. The balloon B is constructed so that it has a flexible configuration when it is in a deflated condition and an elongated, straight configuration when it is in an inflated condition.

Figure 38:
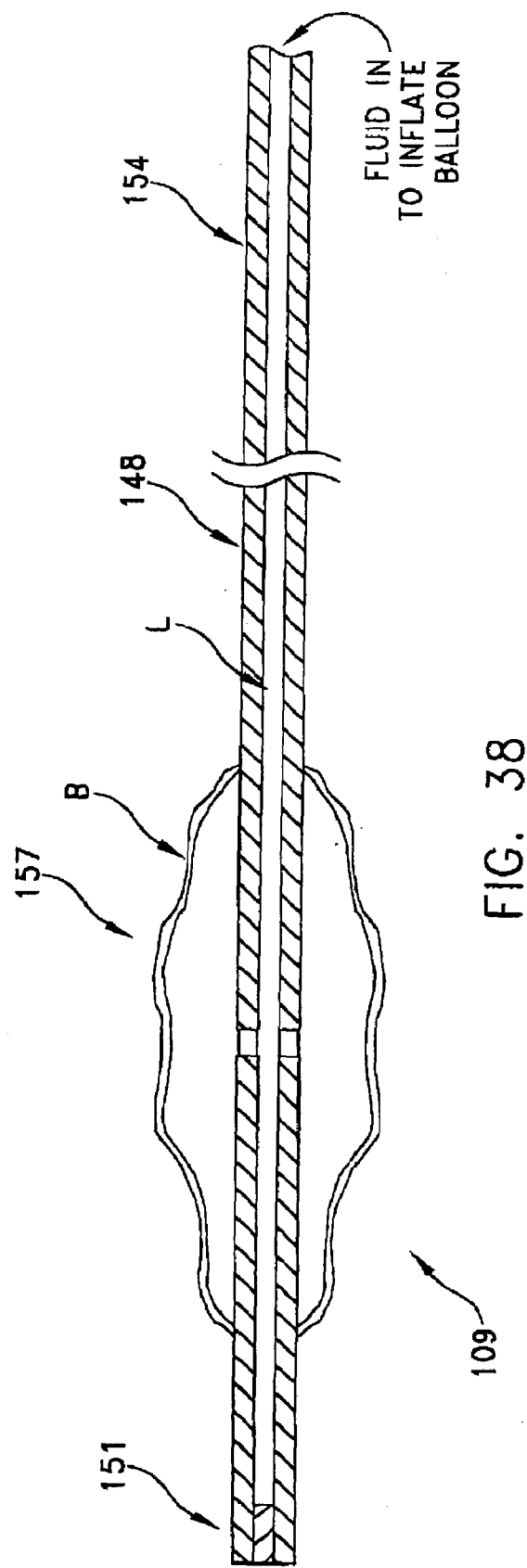
FIG. 38 illustrates another form of the present invention.
Figure 39:
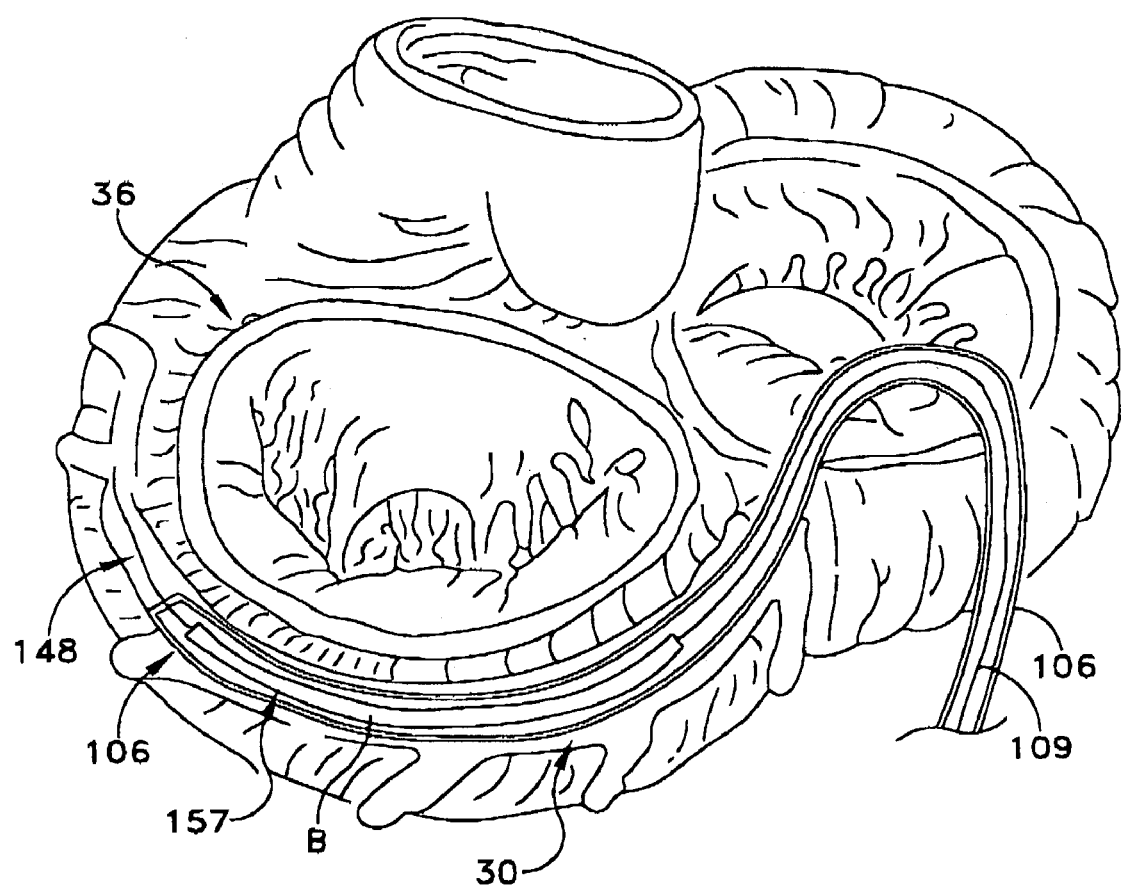
FIGS. 39 and 40 illustrate the embodiment of FIG. 38 in use.
Figure 40:
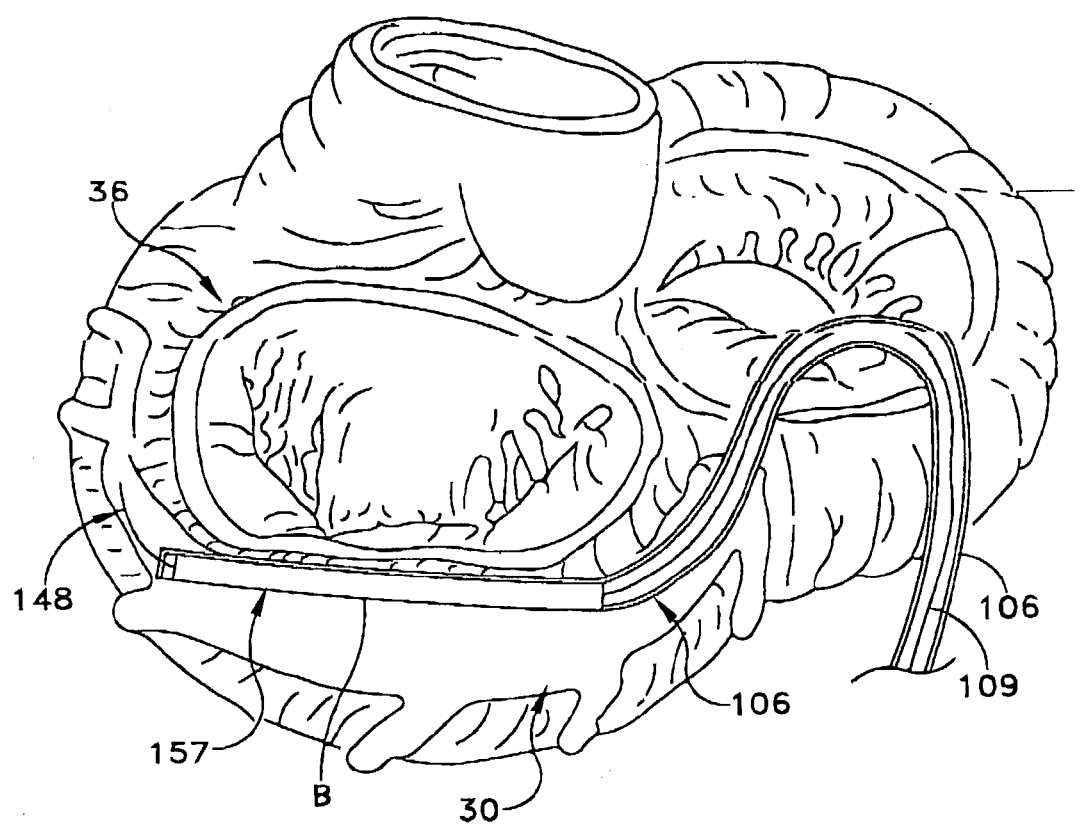

The push rod 109 of FIG. 38 may be used as follows. First, guidewire 103 is advanced into the coronary sinus 30 (FIG. 4). Then delivery catheter 106 is advanced over guidewire 103 until the distal end of the delivery catheter is in coronary sinus 30 (FIG. 5). Next, guidewire 103 is withdrawn (FIG. 6). Then push rod 109, with elongated body 157 in a deflated condition, is advanced along the interior of delivery catheter 106 so that balloon B is adjacent to the mitral valve (FIG. 39). Then balloon B is inflated, using inflation lumen L (FIG. 38), so that elongated body 157 assumes its elongated, straightening configuration (FIG. 40). As this occurs, the posterior annulus of the mitral valve is compressed anteriorly, so as to reduce mitral regurgitation.

It is also possible to form an inflatable elongated body 157 of push rod 109 with other configurations. By way of example, it is possible to form an inflatable body 157 with a piston-type configuration, whereby the body may be elongated or shortened as desired. More particularly, and looking now at FIGS. 41 and 42, inflatable body 157 may comprise a distal portion 157' and a proximal portion 157", with the distal and proximal portions being in a sliding, piston-like relationship. As a result, fluid may be supplied to the combined interiors of the distal and proximal portions, so as to force the two elements apart relative to one another.

In use, the push rod 109 of FIGS. 41 and 42 is positioned in its "compressed" state (FIG. 41), passed down the interior of delivery cannula 106 until inflatable elongated body 157 is positioned adjacent to the mitral valve, and then inflated (using inflation lumen L) into its "expanded" state (FIG. 42). As this occurs, the naturally curved coronary sinus is straightened, thereby pushing the posterior annulus of the mitral valve anteriorly, whereby to reduce mitral regurgitation.

In addition to the foregoing, it should also be appreciated that with respect to push rod 109, the flexible body 148 may comprise an electrical lead for an implantable bi-ventricular pacing device and/or an electrical lead for an implantable cardio defibrillator device, etc. In this case, the distal end of flexible body 148 would be elongated somewhat and would not reside within the coronary sinus; rather, it would be positioned within the tissue which is to receive the electrical stimulus while elongated body 157 is positioned adjacent to the mitral valve. Such a construction would allow the bi-ventricular pacing device and/or the implantable cardio defibrillator device to work in conjunction with elongated body 157 to reduce mitral regurgitation.

It should also be appreciated that the function of hydraulic energy employed to enlarge inflatable body 157 may be substituted by a mechanical energy transformer such as a lead screw mechanism or an electromechanical solenoid.

In a corresponding fashion, the guidewire 103 over which elongated body 184 is deployed may also be in the form of an electrical lead for an implantable bi-ventricular pacing device and/or an electrical lead for an implantable cardio defibrillator device, etc. Again, in this case the distal end of the wire will be positioned within the tissue which is to receive the electrical stimulus while elongated body 184 is positioned adjacent to the mitral valve. Such a construction would allow the implantable bi-ventricular pacing device and/or the implantable cardio defibrillator device to work in conjunction with elongated body 157 to reduce mitral regurgitation.

Figure 43:
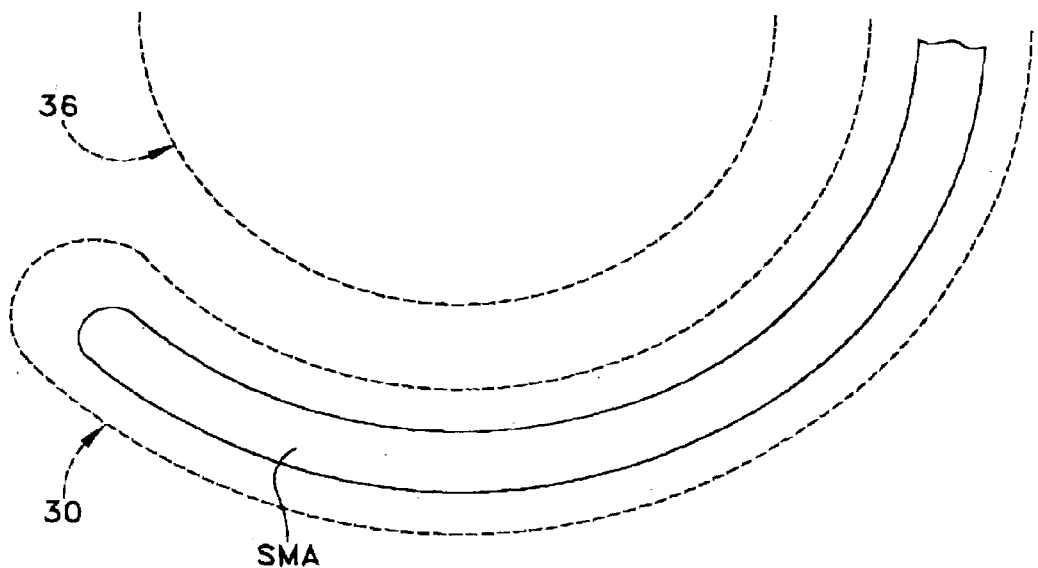
FIGS. 43 and 44 illustrate still another aspect of the present invention.
Figure 44:
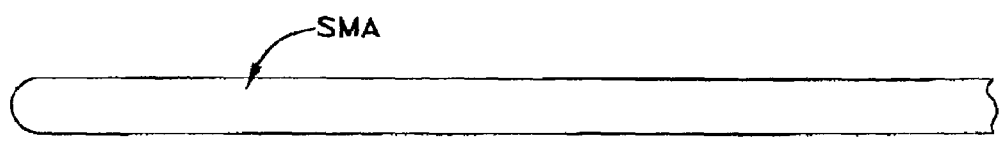

Looking next at FIGS. 43 and 44, there is shown yet another form of the present invention. In this form of the invention, there is provided an elongated shape memory alloy body SMA which is configured to be substantially flexible at a temperature $T_1$ and substantially rigid and in a straight configuration at another temperature $T_2$, where temperature $T_2$ is normal body temperature. In this situation, body SMA is brought to temperature $T_1$, so that it may be inserted more easily into the natural curvature of the coronary sinus, e.g., during insertion of body SMA into the coronary sinus (FIG. 43). However, when body SMA thereafter transitions to temperature $T_2$, body SMA will assume its straight configuration (FIG. 44), whereby to apply an anteriorly-directed force to the posterior annulus of the mitral valve and reduce mitral regurgitation. It will be appreciated that the configuration of body SMA may be other than straight (i.e., "w" shape, etc.) to best displace the posterior annulus anteriorly.

In other alternative embodiments, the elongated body may be flexible along at least a portion of its length. Regional flexibility and regional stiffness may allow for straightening of select locations of the coronary sinus and corresponding locations of the posterior mitral annulus. This can cause regions of the mitral annulus to move anteriorly, thus causing regional improvements in leaflet coaptation. In addition, the elongated body may be formed by two end segments connected together by a filament: by anchoring the two end segments relative to the anatomy and pulling the filament taught, the naturally curved wall of the coronary sinus can be straightened, whereby to move the posterior mitral annulus anteriorly and thereby reduce mitral regurgitation.

As noted above, anchoring structures can be used to ensure that the body 157 (or 184) and delivery catheter 106 do not migrate over the life of a long-term implant. A proximal termination allows the body 157 to be permanently implanted in the vascular system. The proximal termination also allows convenient removal or replacement of the body 157. The proximal termination may also provide additional anchoring of the entire system.

Figure 45:
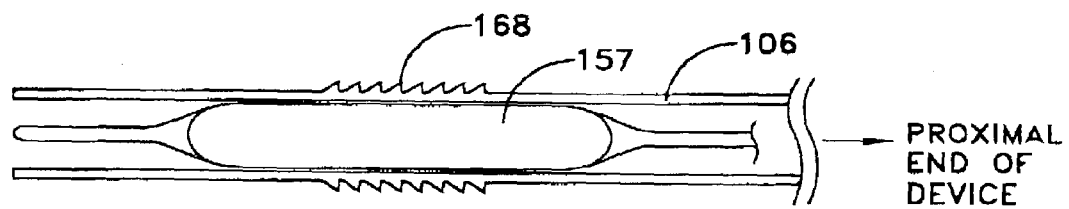
Figure 46:
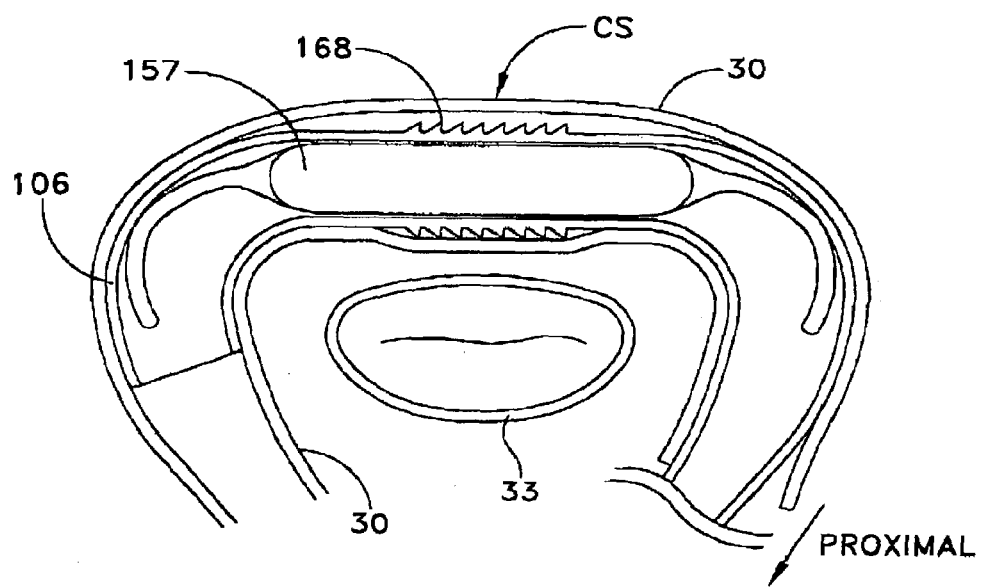
Figure 47:
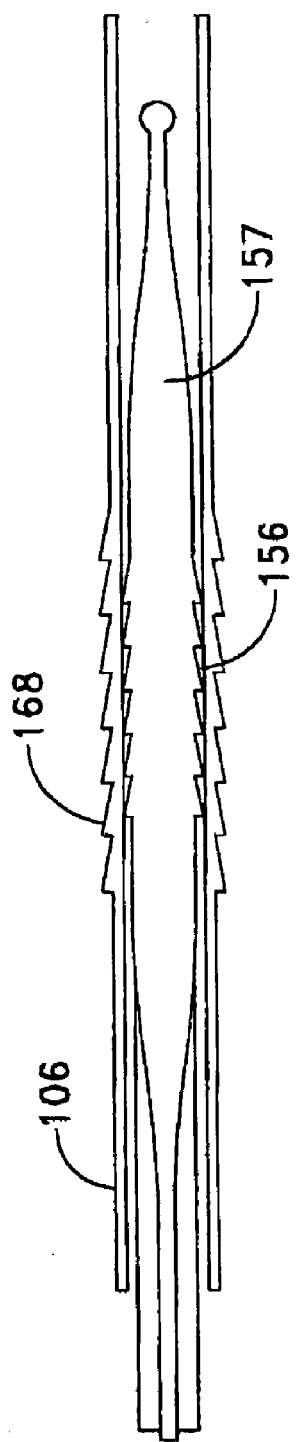

It is desirable to provide an anchor to retain the body and/or delivery catheter securely in place without causing trauma or dissection to the coronary sinus. A series of antimigration barbs 168 may be fabricated into the outside diameter of the delivery catheter 106, as shown in FIG. 45. When the body is in place, a large load is placed onto the midsection of the body 157. As can be seen in FIG. 46, the anti-withdrawal barbs 168 load only into the wall of the coronary sinus 30 where that wall is supported by the underlying heart muscle between the body 157 and the mitral annulus 33. The barbs 168 do not load into the unsupported outer wall of the coronary sinus. There are no barb features at either end of the body 157 that might cause damage to the coronary sinus. Without the rod 109 in place, the delivery catheter 106 can flex as it negotiates corners. This ability allows the delivery catheter to withdraw through the vascular system without causing trauma to the intima of the vessels.

The straight, substantially rigid elongated body 157 (or 184) may be provided with barbs 156 to stabilize the portion thereof within the delivery catheter 106. The barbs 156 are arranged such that the catheter 106 may be withdrawn from the body 157 (or 184). Barb anchoring can be unidirectional or bi-directional. The barbs 168 engage the inner wall of the coronary sinus and the underlying heart muscle when the device is used without an indwelling delivery catheter in a drop-off configuration. The barbs 168 will engage the internal wall of the delivery catheter 106 when a delivery catheter is used in a non-drop off configuration.

Figure 48:
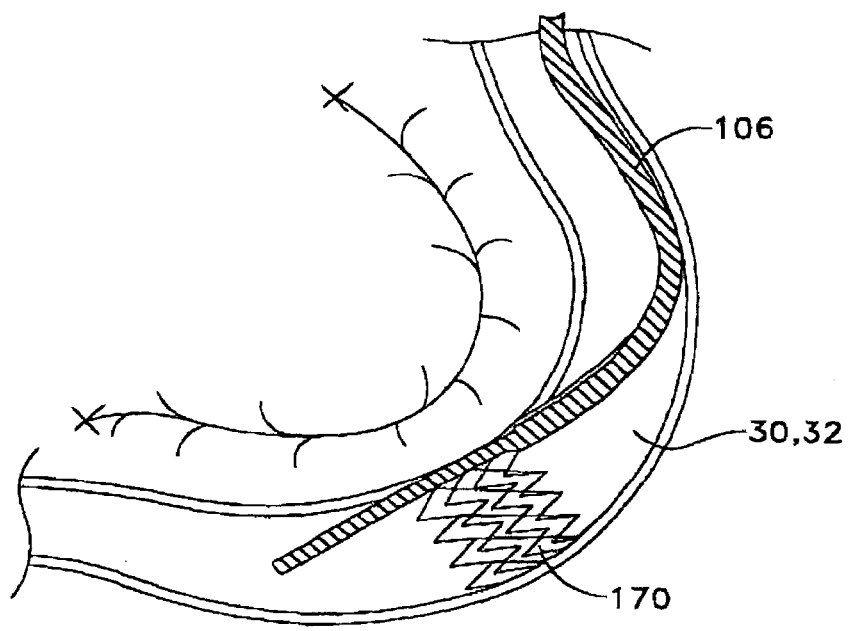
Figure 49:
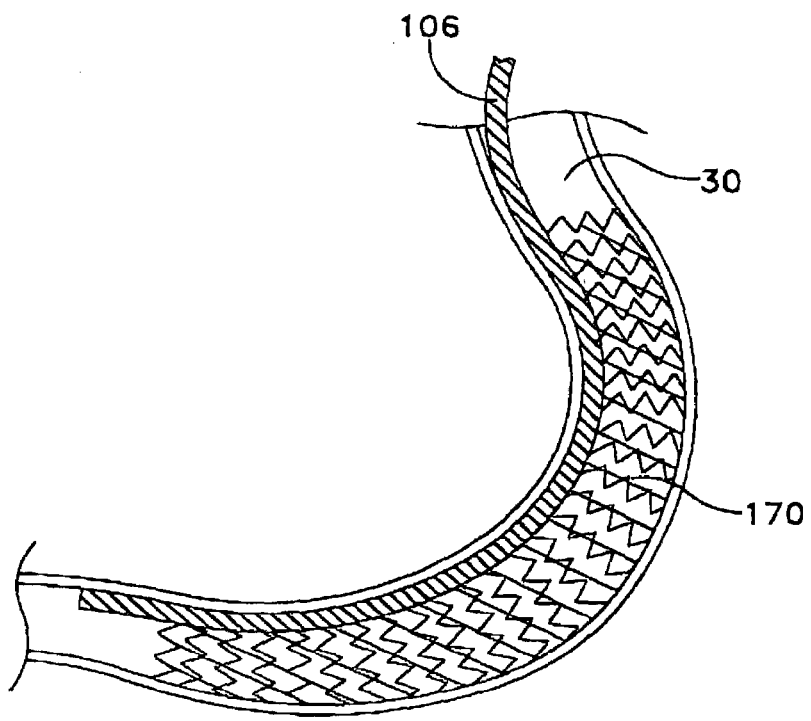

An alternative anchoring structure is a stent 170 (FIGS. 48 and 49) comprising a generally open metallic or bioabsorbable structure that can be collapsed for insertion and then expanded in place. The expansion mechanism may be active (e.g., an inflatable balloon) or passive (e.g., pre-formed shapes in a nickel titanium structure). A stent is generally used to expand the vessel in which it is placed, but in this case it is used in its expanded condition as an anchor for the body 157 and/or the delivery catheter 106. Typical locations for an anchoring stent include the anterior interventricular vein, the great cardiac vein 32, or the coronary sinus 30. FIG. 48 shows a distally located stent 170 in the anterior interventricular vein 32 or coronary sinus 30. FIG. 49 shows a stent 170 that runs the entire length of the coronary sinus 30.

Figure 50:
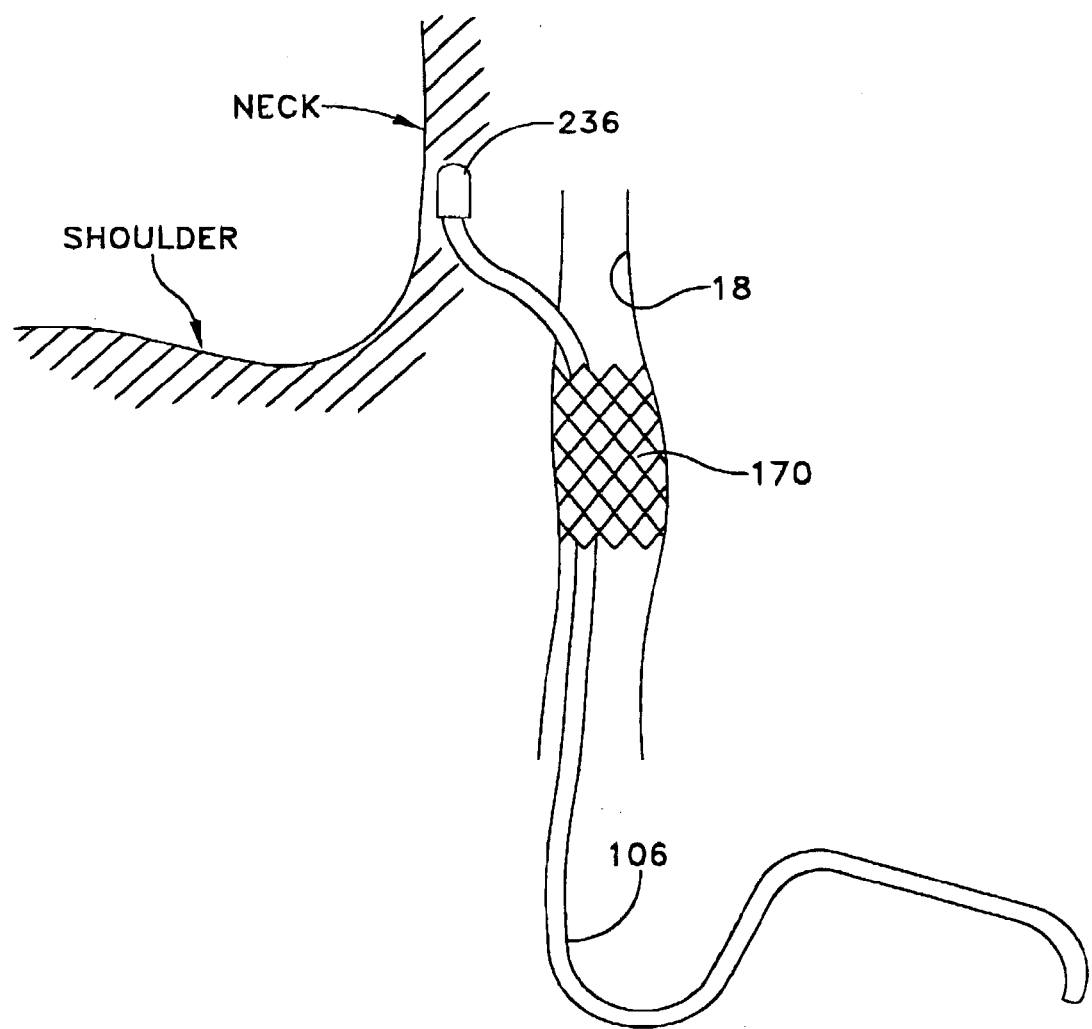

Stents may also be used at the proximal termination site (in the internal jugular vein 18, subclavian vein or femoral vein) to provide improved fixation and/or anchoring at that location, as shown in FIG. 50.

Distal hooks 174 (FIG. 51) can be provided for reliable anchoring in the anterior interventricular vein 32 or great cardiac vein. Release of the hooks 174 may require a surgical procedure or a custom release device.

Figure 51:
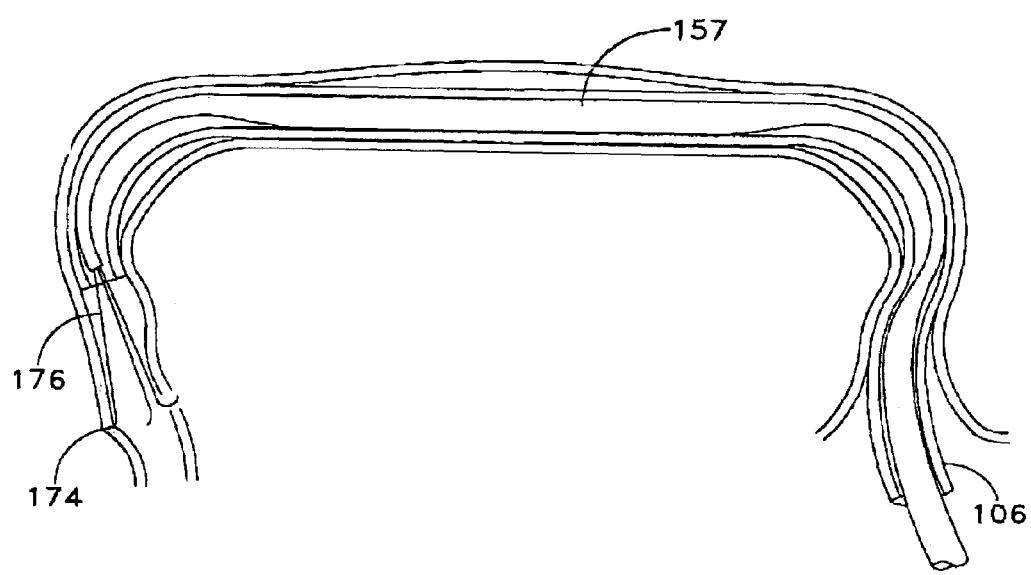
Figure 52:
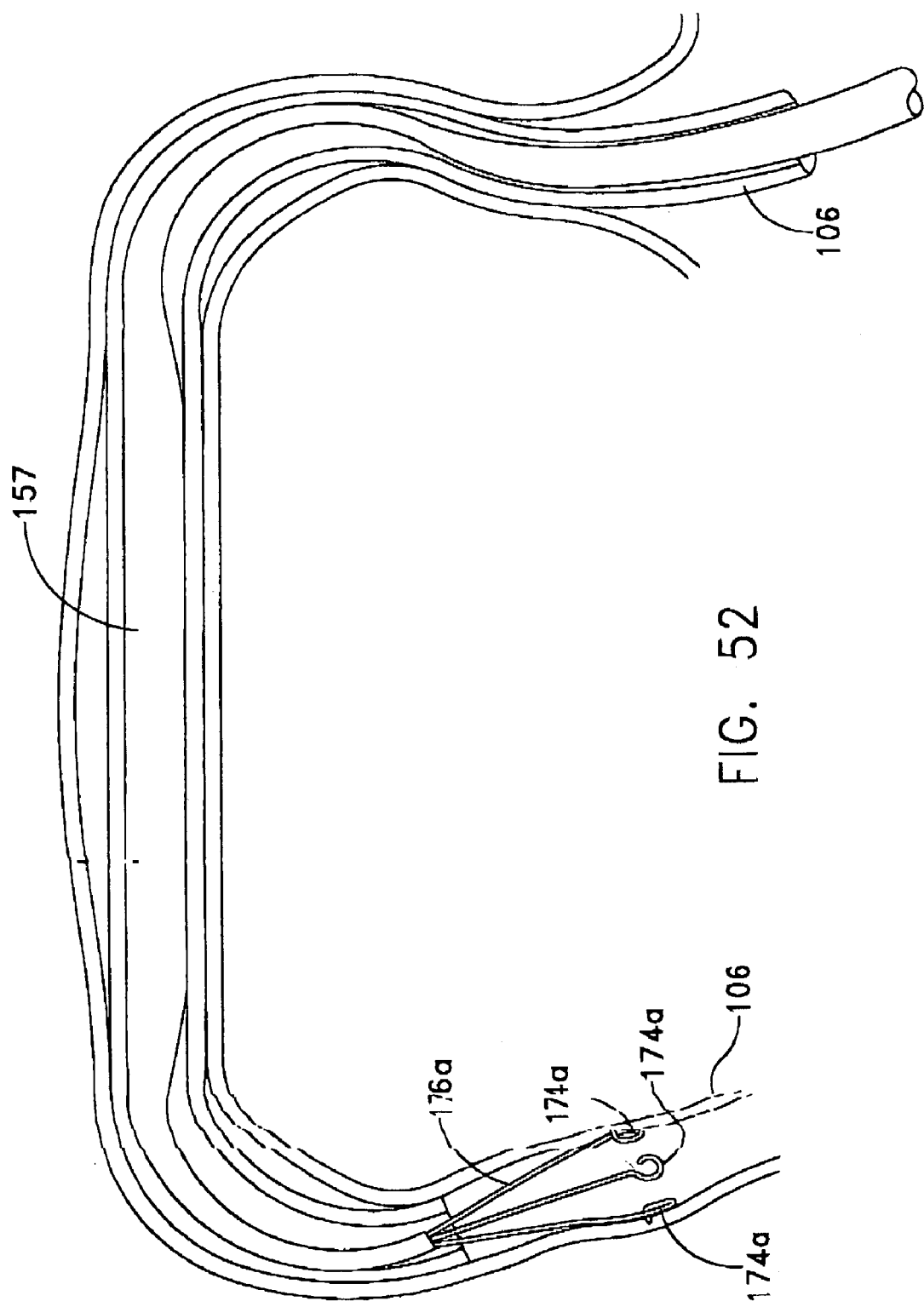

FIG. 51 shows a set of perforating hooks 174 on an expanding three-legged structure 176 connected to the body 157. FIG. 52 shows a set of non-perforating hooks 174a on an expanding three-legged structure 176a.

Figure 53:
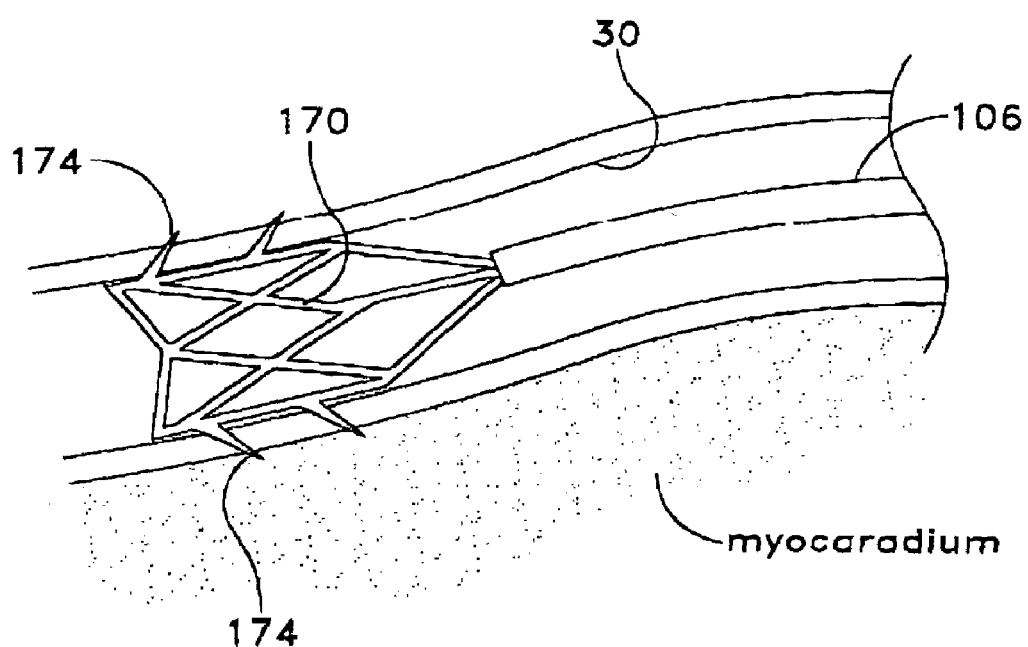
Figure 54:
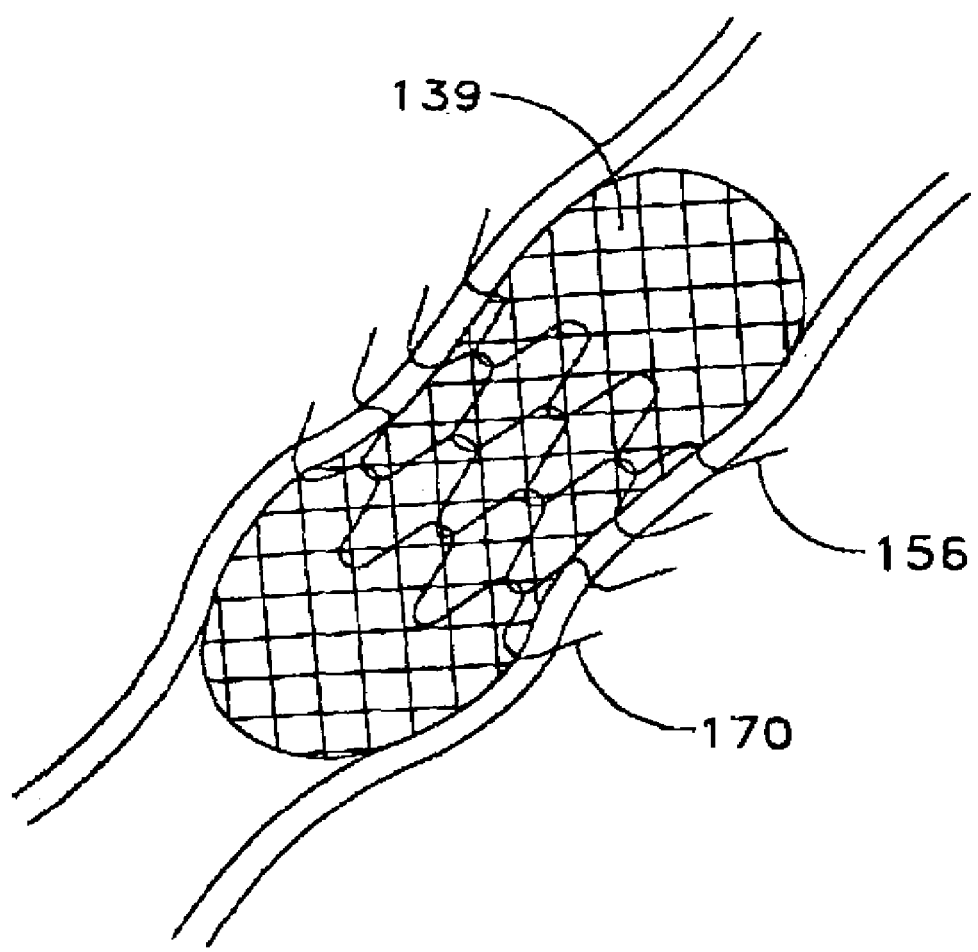

Stents 170 and hooks 174 are well suited to be used in combination to allow anchoring and vessel patency, as shown in FIG. 53. Stents 170 may also be used in combination with expansion devices (e.g., balloons) 139, and further in combination with hooks 174 or barbs 156 (FIG. 54). If a hook is designed to be perforating, expanding foam or other blockers may be used in the anterior interventricular (AIV) to provide hemostasis. Since this expanding foam is occlusive to the vessel in which it is placed, it will not be incorporated in perforating designs for anchors in the proximal portion of the coronary sinus.

Hooks 174 may be self-deploying, released by removing a protective sleeve, or other such method. Alternatively, hooks 174 may be deployed by an active mechanism, such as a balloon, mechanical wedge, etc.

Figure 55:
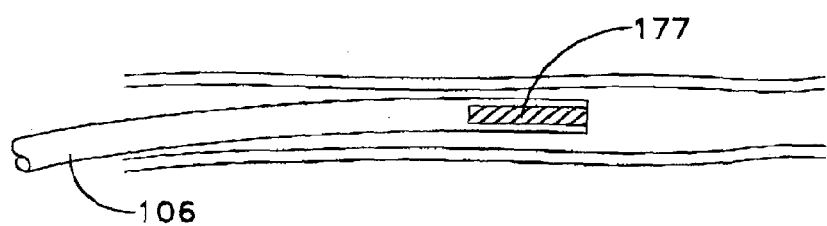
Figure 56:
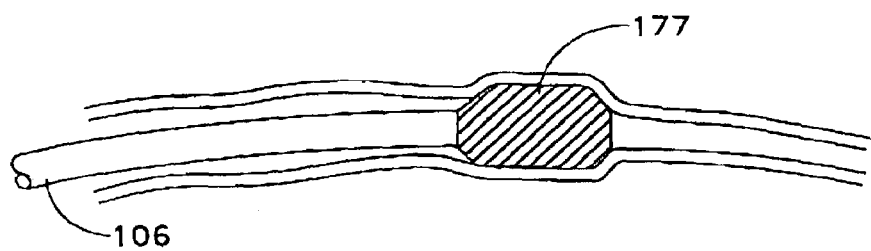
Figure 57:
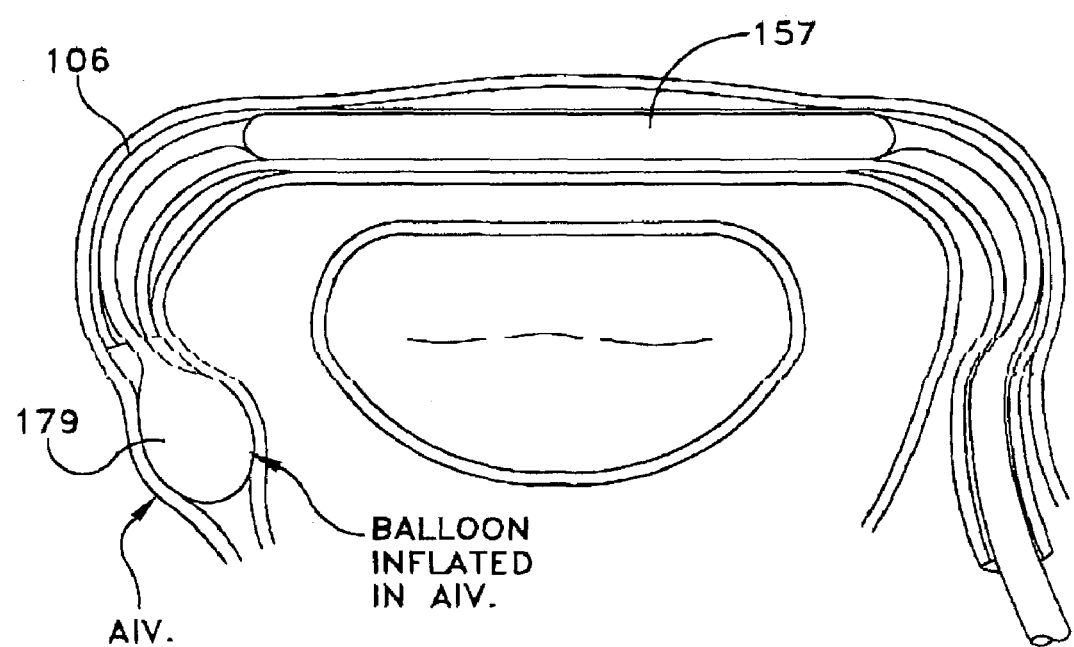

Expanding anchors for the bodies 157, 184, or delivery catheters 106, include expandable devices 139 which may be attached to either the delivery catheter or the body itself. FIGS. 55 and 56 show an expandable foam structure 177 attached to the body 157 that is inflated in the AIV or great cardiac vein. By virtue of its shape, it lodges in that vessel and resists any tendency of the body to migrate out of the coronary sinus. FIG. 57 shows a balloon 179 attached to the body 157 that provides anchoring of the distal end of the rigid body 157 and the guiding catheter during placement of the body 157 and/or long term anchoring of the body.

Rigid (PET, urethane) or complaint (silicone, and the like) balloons can be used with and without textured surfaces, inflatable ridges, or other grip enhancing features. Configurations of more than one balloon (fenestration) may be used to allow blood flow by the inflated balloon or to increase anchor force, as shown in FIGS. 58 and 59.

Expanding foam, such as polyvinylalcohol (PVA), expands significantly from its compressed shape when hydrated. During introduction, the foam is compressed and protected from hydration within a capsule or covering tube. Once the foam has been advanced to the desired position, it is exposed to the hydrating effects of the blood by removing the covering. Once expanded, the foam lodges in the vessel by virtue of the deformation imposed on the vessel in which it expands.

Figure 60:
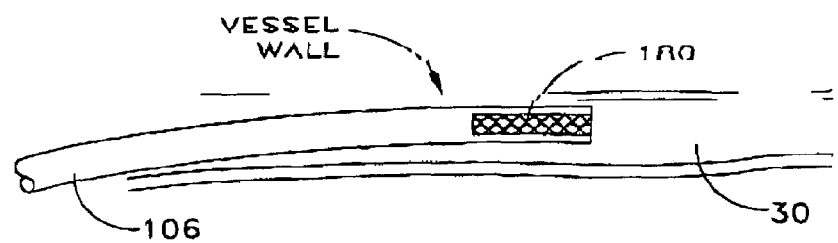
Figure 61:
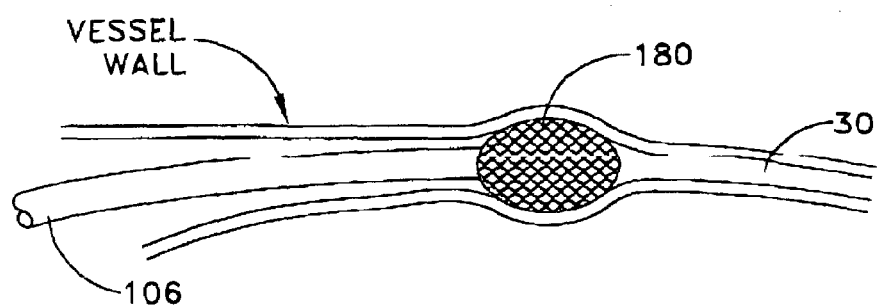

Wire balls 180 (FIGS. 60 and 61) behave in a manner similar to the expanding foams 177. The wire balls 180 may be compressed while introduced through the delivery catheter 106, and then expand when released out of the end of the catheter. The wire balls also anchor by virtue of the deformation imposed on the vessel in which it expands, as shown in FIG. 61.

Figure 62:
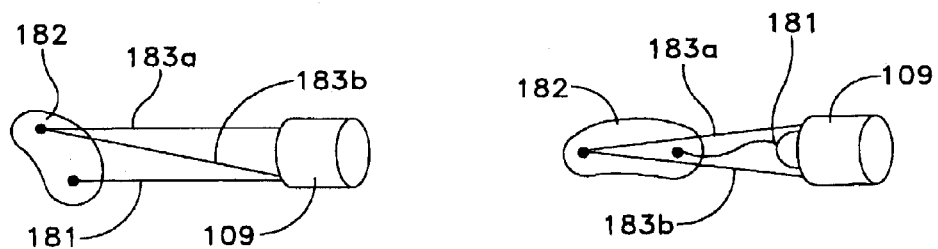
Figure 63:
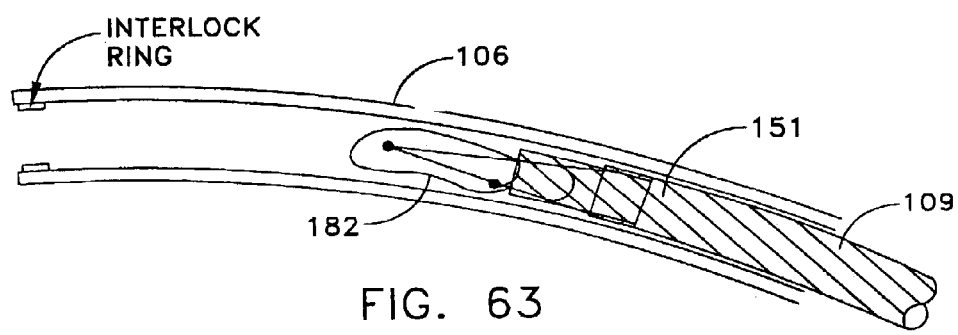
Figure 63A:
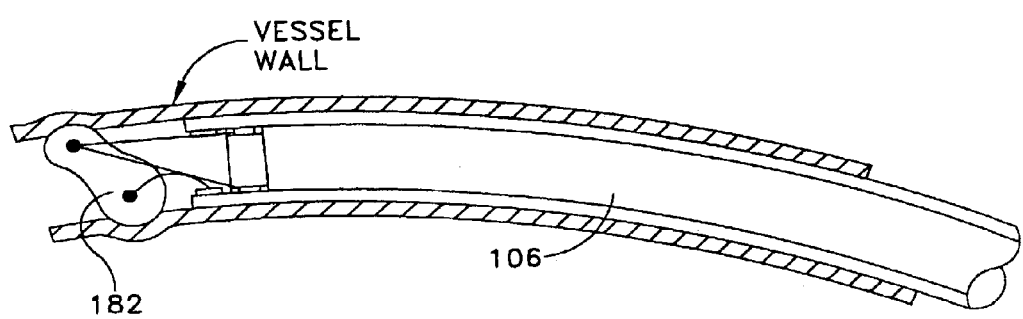

In FIGS. 62, 63 and 63A, there is shown a cam 182 that anchors the delivery catheter 106. This cam 182 functions by distending the vessel into which it is placed. Due to the eccentic attachment of the anchor release wires 183a, 183b and a push wire 181, withdrawing motion of the delivery catheter causes the cam 182 to lock in place. The cam is released by pulling on the release wires, which causes the cam to align its long axis along the axis of the vessel, thereby allowing the entire device to be removed.

Figure 64:
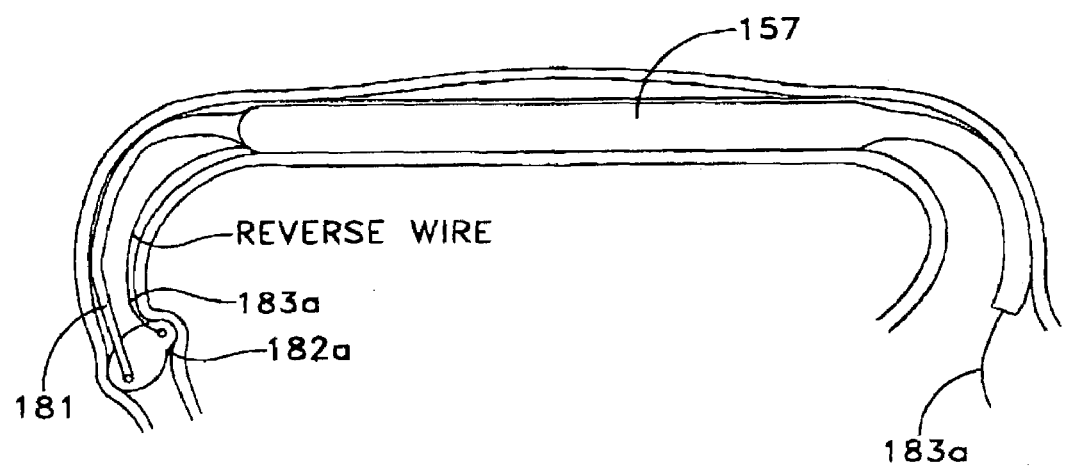

FIG. 64 shows a similar cam device 182a attached to the body 157. The aforementioned release wire 183a is shown in FIG. 64.

Several biocompatible adhesives are suitable for incorporation in the delivery catheter and serve to lock a catheter in place. Once the catheter tip is wedged into the desired position within the vessel, glue may be dispensed through one or more tip orifices 186a, 186b (FIGS. 65–68). Alternatively, glue may be dispensed through its own lumen 185 or may be contained in a distal sponge-like tip 186 (FIG. 68) that dispenses the glue when squeezed against the vessel wall, or when inflated from within by a balloon.

Distal and proximal blood flow blockers of balloons may be used to shut off blood flow in the vicinity of the glue bond. This prevents glue being washed away prior to setting up.

Figure 69:
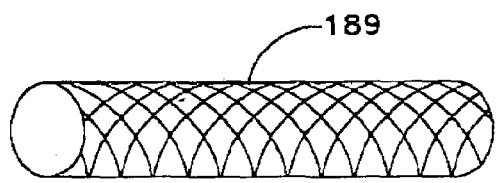

Enhanced in-growth surface treatments or coatings, applied to the outside wall of the delivery catheter 106 and/or the body 157 encourages ingestion of fibrous tissue and adherents that will help provide long-term anchoring of the assembly. One example is a mesh structure 189 (FIG. 69) made from Dacron or similar material. Its anchoring properties increase in strength over the first few days in place, and after that time in-growth provides a secure retention of the components.

Figure 70:
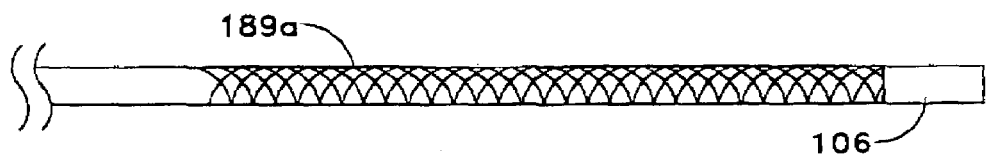
Figure 71:
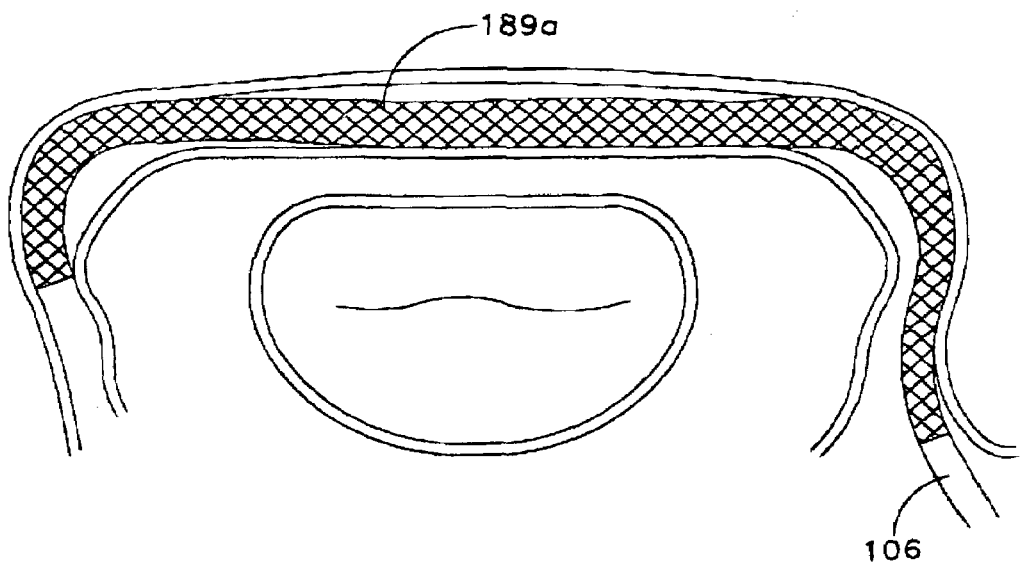

External mesh 189A (FIGS. 70 and 71) may also function as a textured surface, providing short or long term anchoring in a manner similar to external barbs 168, 156 on the catheter or body. Other surface treatments include surface texturing, the use of felted or hairy components, or the incorporation of structures resembling fish scales or shark's skin.

Figure 72:
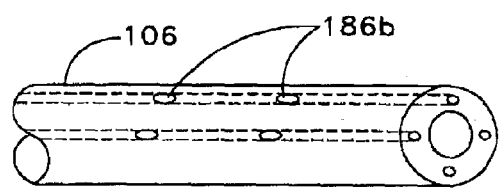
Figure 73:
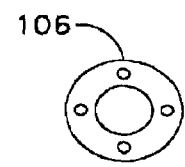

Referring to FIGS. 72 and 73, it will be seen that orifices 186b along the catheter 106 may be positioned such that when a vacuum is pulled on the catheter, tissue is sucked into the orifices, temporarily anchoring the catheter to the wall of the vessel.

Figure 74:
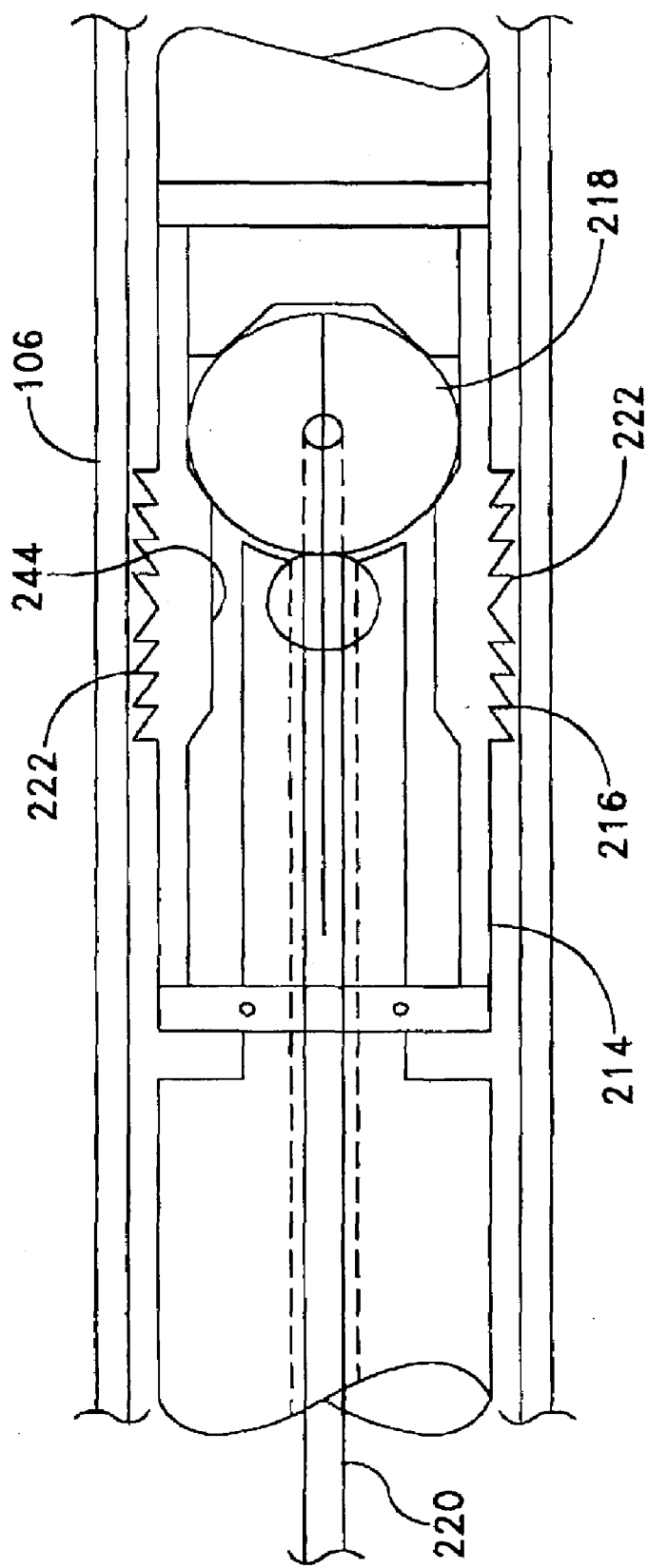
Figure 75:
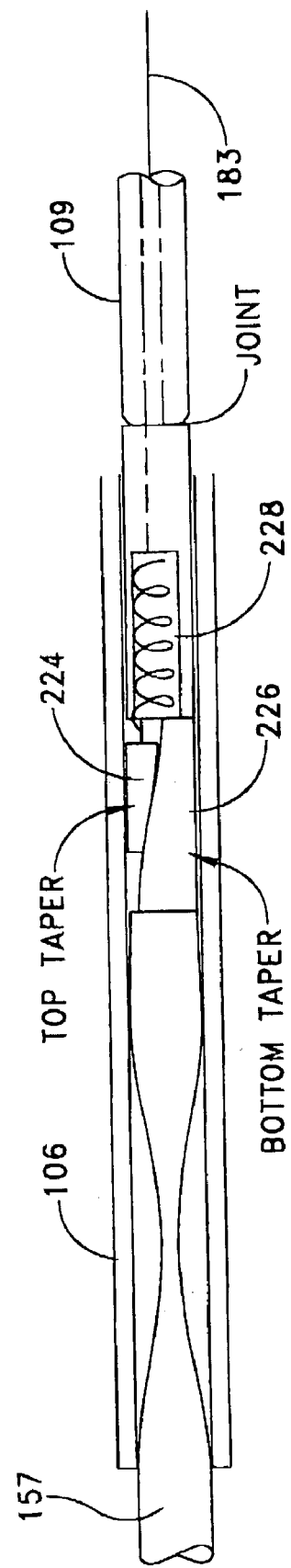

An assembly for locking the body 157 within the delivery catheter 106 is shown in FIG. 74. The assembly includes a slit tube 214 with variable inner wall diameters and an outer detent feature 216. A ball 218 with integral pull wire 220 rests within the slit tube 214. Once the body 157 is placed appropriately, the pull wire 220 is activated, pulling the ball 218 into the reduced internal diameter section 244 of the slit tube 214. This forces the barbed midsection 222 into an interference with the internal diameter of the delivery catheter 106, and thereby locking the tube 214, and its attached components, into place within the delivery catheter. When it is time to release the tube 214, and body 157, the ball 218 is pulled once again into the enlarged internal diameter section 244 of the slit tube 214, releasing the tube 214 and body 157 to slide once again within the delivery catheter 106.

An alternative assembly for locking the body within the catheter comprises a matched set of tapered cams 224, 226 that passively resist motion in one direction and yet can be slid in either direction. When advancing the body by pushing on the push rod 109, the force is transmitted through the bottom-tapered cam 226. This disengages the cam lock and allows the whole assembly to slide forward. When withdrawing the body by pulling on the pull wire 183, the tensile force is applied only to the top tapered cam 224. This action also disengages the cam lock. However, if local motions and forces attempt to push the body in the withdrawing direction, the cam lock aggressively engages the internal diameter of the delivery catheter 106, assisted by a cam spring 228. This prevents any withdrawing motion until the upper cam 224 is actively disengaged by once again pulling on the release wire 183. This mechanism may be made bi-directional by assembling two devices back-to-back.

Figure 76:
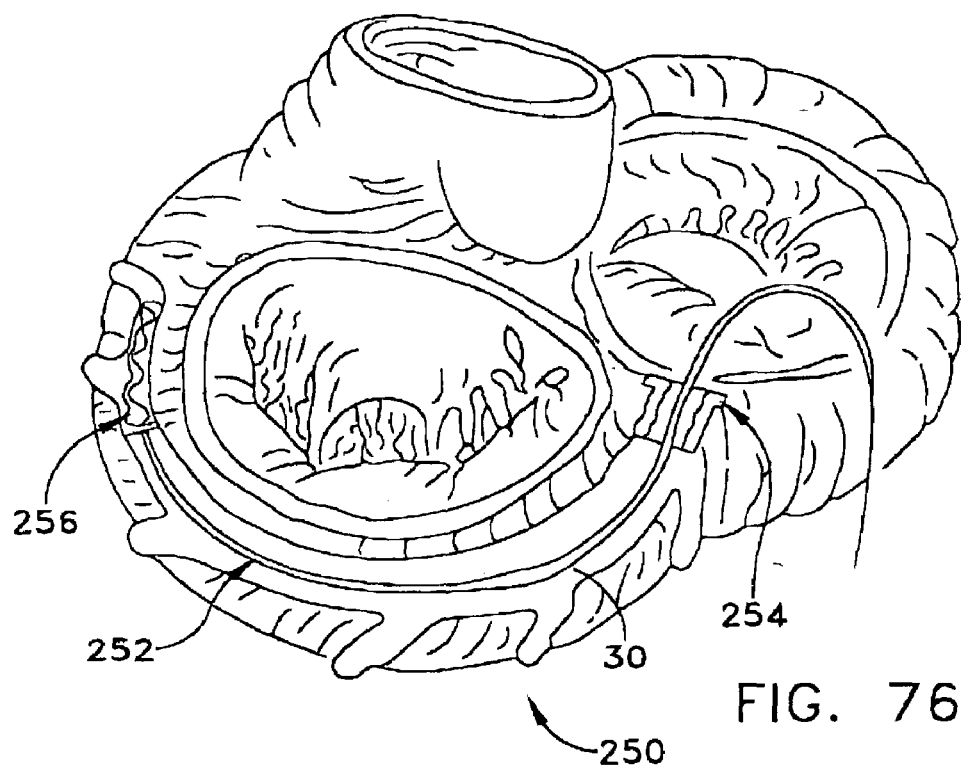
FIGS. 76 and 77 illustrate another alternative method and apparatus for reducing mitral regurgitation.
Figure 77:
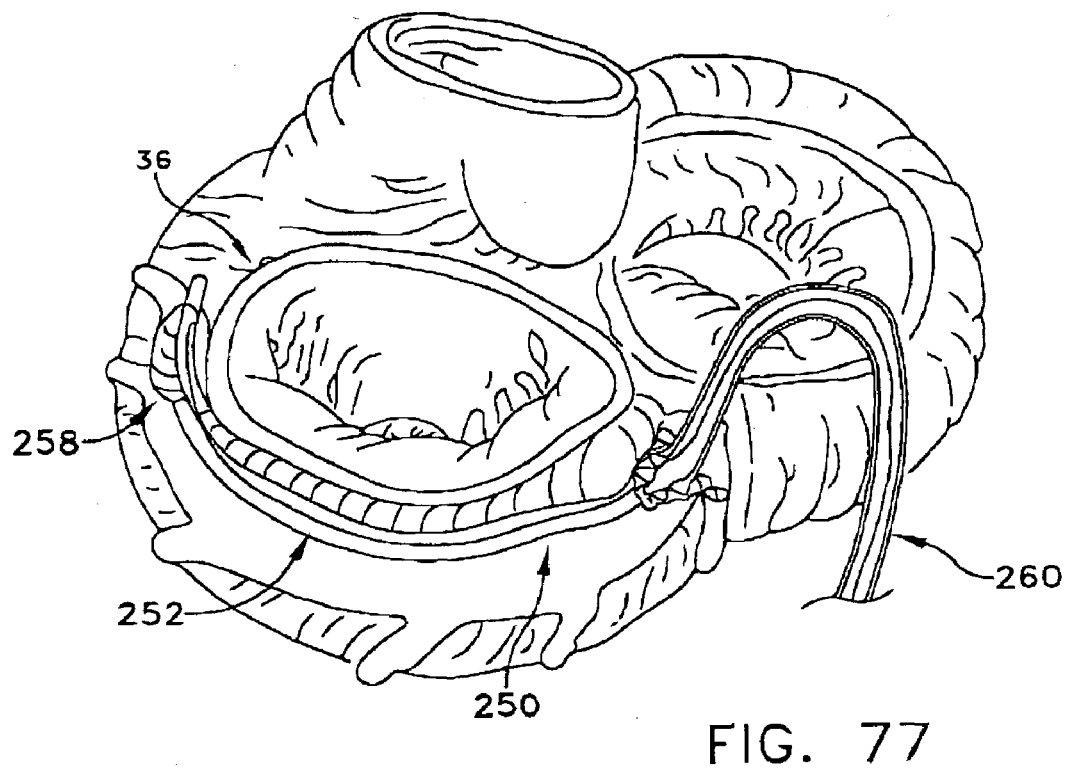

In FIGS. 76 and 77, there is illustrated an annulus cinching apparatus 250 which has been guided into the coronary sinus 30 by guidewire and/or catheter means described above. The apparatus 250 comprises a flexible cinching tether 252, distal anchoring means 256, and/or proximal anchoring means 254. In FIG. 77, a preferred embodiment of apparatus 250 employs an inflated balloon anchoring means 258 to anchor the distal end of tether 252. Cinching activation means 260, upon operation, exercises a movement force on proximal anchoring means 254, causing movement of flexible tether 252 so as to cinch the posterior wall of the mitral annulus which, in turn, pushes the posterior mitral valve leaflet anteriorly. Tension may be maintained in apparatus 250 by locking any relative motion of the tether 252 and cinch activation means 260, both outside the body.

In another preferred embodiment, the distal anchoring means 256 may be a stent, described hereinabove, that anchors to the circumference of the vein, or penetrates through the wall of the vein and into the myocardium. For this latter embodiment, distal anchor 256 may be permanently implanted into the patient, and the other components of the apparatus 250 may remain in the body, but the anterior movement of the posterior annulus may be temporary.

In yet another preferred embodiment, proximal anchor 254 may be a balloon, or simply a flange part of cinch activation means 260 that is too large to enter the ostium of the coronary sinus 30.

In the preceding discussion, elongated body 157 (or 184) is generally described as being straight and substantially rigid, with or without relatively flexible portions 175 (FIG. 10) and/or elongated relatively flexible portions 178 (FIG. 11) and/or extended strain relief tapers 200 (FIG. 11B). However, it should be appreciated that the terms "substantially rigid", "relatively flexible" and the like are meant to be interpreted in the context of the anatomical tissue involved and should not be interpreted in an absolute sense.

Fundamentally, elongated body 157 (or 184) is constructed so that (1) its intermediate portion imparts an anteriorly-directed force on the walls of the coronary sinus (e.g., as shown by the arrows A in FIG. 7), and (2) its distal and proximal ends impart a posteriorly-directed force on the walls of the coronary sinus (e.g., as shown by the arrows P in FIG. 7). Conversely, a high center load 140 (FIG. 11T) is imparted to the intermediate portion of elongated body 157 (or 184) by the mitral annulus, and smaller loads 141 (FIG. 11T) are directed to the distal and proximal ends of elongated body 157 (or 184) by the posterior portions of the coronary sinus.

In order to better distribute the loads on the proximal portions of the coronary sinus, the distal and proximal ends of elongated body 157 (or 184) may have relatively flexible portions 175 (FIG. 10) and/or elongated relatively flexible portions 178 (FIG. 11) and/or extended strain relief tapers 200 (FIG. 11B). Furthermore, the flexibility of these portions 175, 178 and/or 200 can vary along their lengths; thus, as shown in FIGS. 11R and 11S, the extended strain relief tapers 200 can become more flexible as they extend toward their outer ends.

Figure 78:
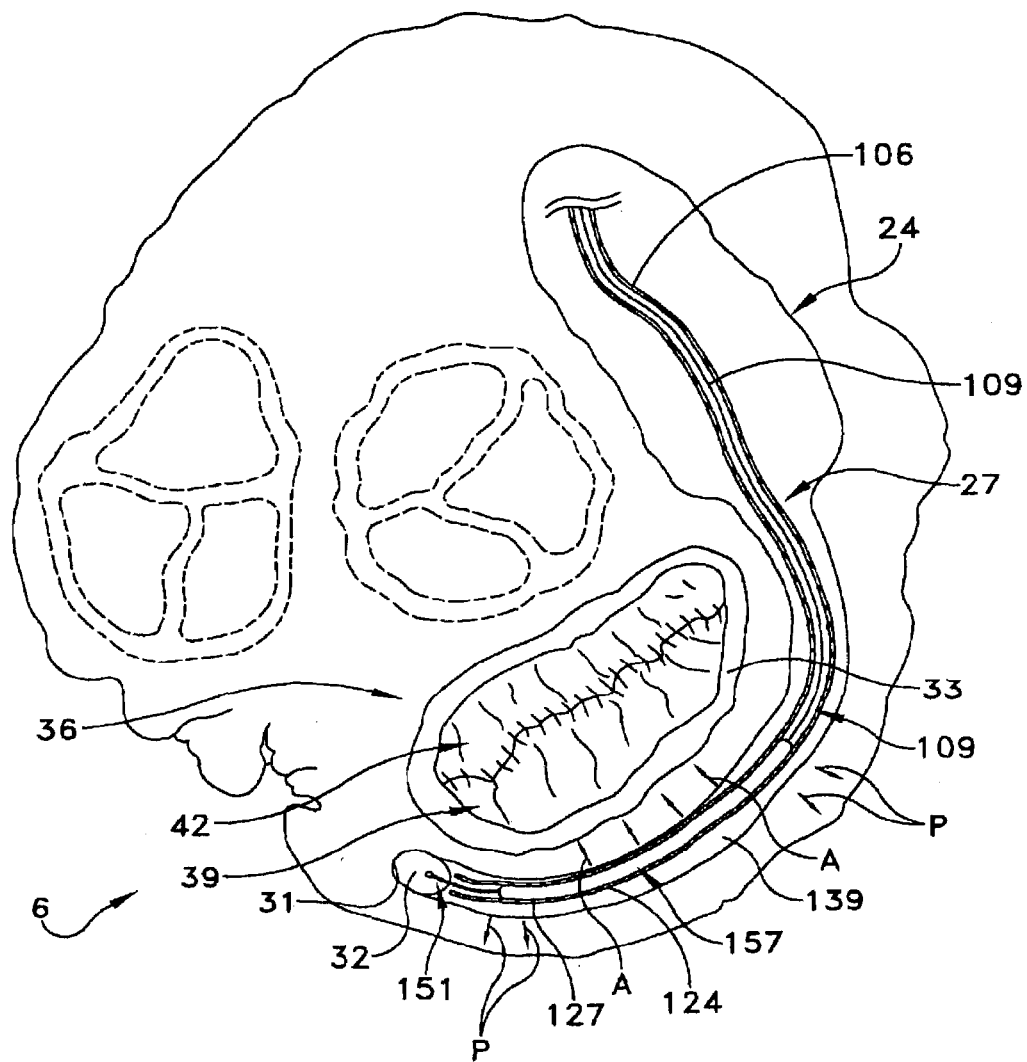
FIG. 78 illustrates another form of the present invention.

Indeed, there is nothing in the present invention which requires that the intermediate portion of elongated body 157 (or 184) be absolutely rigid; in fact, it will function satisfactorily so long as it is substantially resistive to the load 140 (FIG. 11T) imposed by the mitral annulus. The design is further enhanced by having the distal and proximal ends of elongated body 157 (or 184) be somewhat less resistive to the smaller loads 141 (FIG. 11T) directed by the posterior walls of the coronary sinus. Thus, a satisfactory design may be implemented with a device which has a flexibility gradient along its length, with a highest rigidity at or near the center and lower rigidity at or near its two ends. This may be accomplished by tapering the elongated body; and/or by varying its material properties; and/or by other techniques. Or a satisfactory design may be implemented with a device which has some degree of flexibility along its entire length; and this flexibility may vary with length or may be constant along the entire length of the body. See, for example, FIG. 78, which shows an elongated body 157 having a degree of curvature throughout its length.

It should be appreciated that the present invention may be used to alter the shape of other cardiac tissues, including but not limited to the left ventricle, for other uses, including the treatment of cardiac dysfunction.

It is to be understood that the present invention is by no means limited to the particular constructions herein disclosed and/or shown in the drawings, but also comprises any modifications or equivalents within the scope of the claims.

What is claimed is:

1. An assembly for reducing mitral regurgitation, the assembly comprising:
   a flexible delivery catheter for insertion into a coronary sinus of a patient in a vicinity of a posterior leaflet portion of a mitral valve;
   structure for anchoring a distal end of said catheter in the coronary sinus;
   a generally flexible push rod adapted for passage through said delivery catheter; and
   an elongated substantially straight rod portion comprising a portion of said push rod and defining a more rigid portion of the length of said generally flexible push rod and disposed proximal to a distal end of said push rod and configured for moving through said catheter and into a position within said catheter and in the vicinity of the posterior leaflet portion of the mitral valve, said elongated substantially straight rod portion being of a metallic material more rigid than tissue proximate the posterior leaflet portion of the mitral valve, and being sized whereby to straighten a natural curvature of at least a portion of the coronary sinus in the vicinity of the posterior leaflet portion of the mitral valve, to move a posterior annulus portion of the mitral valve anteriorly and thereby improve coaptation between the posterior leaflet and an anterior leaflet portion of the mitral valve.

2. The assembly in accordance with claim 1 wherein said anchoring structure comprises barbs on said catheter for engaging with internal wall portions of the coronary sinus.

3. The assembly in accordance with claim 1 wherein said anchoring structure comprises a balloon attached to said catheter, the balloon engaging internal wall portions of the coronary sinus.

4. The assembly in accordance with claim 1 wherein said anchoring structure comprises a stent adjacent said catheter, said stent being adapted upon expansion thereof for engaging internal wall portions of the coronary sinus.

5. The assembly in accordance with claim 1 wherein said anchoring structure comprises hooks attached to said catheter and adapted to engage internal wall portions of the coronary sinus.

6. The assembly in accordance with claim 5 wherein said hooks are fixed on a stent and are adapted to engage the wall portions of the coronary sinus by expansion of the stent.

7. The assembly in accordance with claim 5 wherein said hooks are adapted for engaging with the internal wall and perforating the wall.

8. The assembly in accordance with claim 1 wherein said anchoring structure comprises an expandable foam body attached to said catheter, said foam body being adapted upon expansion for engaging internal wall portions of the coronary sinus.

9. The assembly in accordance with claim 1 wherein said anchoring structure comprises a plurality of selected ones of balloons and foam bodies disposed around the catheter and having gaps therebetween to facilitate blood flow therethrough.

10. The assembly in accordance with claim 1 wherein said anchoring structure comprises a compressed wire ball fixed to said catheter, said wire ball being expandable to engage internal wall portions of the catheter.

11. The assembly in accordance with claim 1 wherein said anchoring structure comprises a cam member mounted in said catheter and moveable into a position for engaging internal wall portions of said catheter and expanding a diameter of said catheter to engage the coronary sinus.

12. The assembly in accordance with claim 1 wherein said anchoring structure comprises lumens in said catheter and extending lengthwise thereof, and side ports in communication with the lumens, the lumens and ports being adapted to flow adhesive therethrough, to bond the catheter distal end to wall portions of the coronary sinus.

13. The assembly in accordance with claim 1 wherein said anchoring structure comprises a mesh fixed to the exterior wall of said catheter for encouraging in-growth of patient body materials.

14. The assembly in accordance with claim 1 wherein said anchoring structure comprises lumens in said catheter and extending lengthwise thereof, and side ports in communication with the lumens, the lumens and the ports being adapted to convey a vacuum therethrough to draw wall portions of the coronary sinus into engagement with catheter wall portions.

15. The assembly in accordance with claim 1 and comprising second anchor structure for anchoring a proximal end of said catheter, said second anchor structure comprising a sewing cuff fixed to the proximal end of said catheter, for suturing to a patient's outer skin.

16. The assembly in accordance with claim 1 and further comprising a cap for sealing closed a proximal end of said catheter, said cap being adapted to plug into the catheter proximal end.

17. The assembly in accordance with claim 1 and further comprising a cap for sealing closed a proximal end of said catheter, the cap comprising a wire mesh crimpable upon the catheter proximal end to seal the proximal end.

18. The assembly in accordance with claim 1 wherein said catheter is provided with at least one prolapse resistant portion comprising a reinforced portion which is less flexible than a remainder of said catheter.

19. The assembly in accordance with claim 1, wherein said elongated body is provided at one end thereof with a rounded non-traumatic tip, and strain relief taper, and in width-wise cross-section, a selected one of round and generally rectangular cross-section.

20. The assembly in accordance with claim 1 wherein said elongated body comprises an elastomeric outer portion disposed upon a core member.

21. The assembly in accordance with claim 20 wherein the core member comprises a selected one of a substantially rigid rod and a substantially rigid tube.

22. The assembly in accordance with claim 21 wherein the core member is a tube comprising a selected one of (i) empty and (ii) filled with a substantially rigid material.

23. The assembly in accordance with claim 20 wherein said outer portion is formed with barbs thereon.

24. The assembly in accordance with claim 1 wherein said elongated body is provided with strain relief steps at either end thereof.

25. The assembly in accordance with claim 1 wherein said elongated body is provided with strain relief segments mounted on a central rod.

26. The assembly in accordance with claim 1 wherein said elongated rod portion is comprised of a selected one of (i) nickel titanium and (ii) an alloy thereof.

27. The assembly is accordance with claim 1 wherein said body is anchored in said catheter by a selected one of barbs on said body, stents adjacent said body, and hooks attached to said body.

28. The assembly in accordance with claim 1 wherein said body is anchored in said catheter by an expansion member.

29. The assembly in accordance with claim 28 wherein the expansion member comprises a selected one of a balloon and an expandable foam.

30. The assembly in accordance with claim 1 wherein said body is anchored in said catheter by a selected one of an adhesive, a vacuum, an annular lock, a wedge lock, and a cam.

31. The assembly in accordance with claim 1 wherein said elongated body comprises:
   an inner tubular member having a plurality of slots extending widthwise of said inner tubular member; and
   an outer tubular member rotatably disposed on said inner tubular member, said outer tubular member having a plurality of slots extending widthwise of said outer tubular member;
   the slots of said inner and outer tubular members being alignable with each other to permit bending of said elongated body; and
   the slots of said inner and outer tubular members being movable to unaligned positions such that said elongated body resists bending.

32. The assembly in accordance with claim 1, the assembly further comprising:
   a guidewire for insertion into the coronary sinus;
   said delivery catheter being adapted for insertion into the coronary sinus overriding said guidewire; and
   a push rod for moving the elongated body within said catheter to the position in the vicinity of the posterior leaflet.

33. The assembly in accordance with claim 1 wherein said elongated rod portion is of a shape memory alloy material.

* * * * *